United States Patent
Pasricha et al.

(10) Patent No.: US 8,142,448 B2
(45) Date of Patent: Mar. 27, 2012

(54) ENDOSCOPIC INSTRUMENTS FOR SUTURING TISSUES IN A BODY CAVITY

(75) Inventors: Pankaj Jay Pasricha, Houston, TX (US); Keiichi Arai, Hachioji (JP); Koichi Kawashima, Hachioji (JP); Keita Suzuki, Kokubunji (JP); Koh Kimura, Hachioji (JP); Tsukasa Kobayashi, Hachioji (JP); Yoshihiko Sugi, Hachioji (JP); Tetsuya Yamamoto, Hidaka (JP); Yoshio Onuki, Hino (JP)

(73) Assignees: Olympus Corporation, Tokyo (JP); Apollo Endosurgery, Inc., Austin, TX (US)

( * ) Notice: Subject to any disclaimer, the term of this patent is extended or adjusted under 35 U.S.C. 154(b) by 1069 days.

(21) Appl. No.: 10/303,265

(22) Filed: Nov. 25, 2002

(65) Prior Publication Data

US 2003/0139752 A1    Jul. 24, 2003

Related U.S. Application Data

(60) Provisional application No. 60/333,380, filed on Nov. 26, 2001.

(51) Int. Cl.
A61B 17/10    (2006.01)
(52) U.S. Cl. ........................................ 606/139; 606/144
(58) Field of Classification Search .................. 604/158, 604/264; 606/139, 142, 144, 148, 145, 158, 606/159; 600/121, 156, 565, 564, 562, 566, 600/567
See application file for complete search history.

(56) References Cited

U.S. PATENT DOCUMENTS

| | | | | | |
|---|---|---|---|---|---|
| 4,240,411 | A | * | 12/1980 | Hosono | 600/154 |
| 4,655,752 | A | * | 4/1987 | Honkanen et al. | 604/256 |
| 4,841,888 | A | * | 6/1989 | Mills et al. | 112/169 |
| 5,041,129 | A | * | 8/1991 | Hayhurst et al. | 606/232 |
| 5,080,663 | A | * | 1/1992 | Mills et al. | 606/144 |
| 5,336,229 | A | * | 8/1994 | Noda | 606/144 |
| 5,722,981 | A | * | 3/1998 | Stevens | 606/148 |
| 5,792,153 | A | | 8/1998 | Swain et al. | |
| 5,797,888 | A | * | 8/1998 | Yoon | 604/530 |
| 5,865,726 | A | * | 2/1999 | Katsurada et al. | 600/127 |
| 6,142,931 | A | * | 11/2000 | Kaji | 600/114 |
| 6,293,927 | B1 | * | 9/2001 | McGuckin, Jr. | 604/266 |
| 6,358,197 | B1 | * | 3/2002 | Silverman et al. | 600/29 |
| 6,368,334 | B1 | * | 4/2002 | Sauer | 606/139 |
| 6,464,707 | B1 | * | 10/2002 | Bjerken | 606/139 |
| 6,551,330 | B1 | * | 4/2003 | Bain et al. | 606/144 |
| 6,656,132 | B1 | * | 12/2003 | Ouchi | 600/564 |
| 6,997,931 | B2 | * | 2/2006 | Sauer et al. | 606/139 |
| 2003/0004544 | A1 | * | 1/2003 | Kawashima et al. | 606/222 |

* cited by examiner

*Primary Examiner* — Tuan Nguyen
(74) *Attorney, Agent, or Firm* — Scully, Scott, Murphy & Presser, P.C.

(57) ABSTRACT

A tissue puncturing system used to suture tissues in a body cavity including: an endoscope; a flexible sheath having a distal portion provided with at least a side opening and a lumen, through which an endoscope may pass; at least one mechanism for puncturing tissue disposed in the flexible sheath, and having a pointed end, which is movable from a first position to a second position; and an operation mechanism for moving the mechanism for puncturing between the first and second positions.

7 Claims, 37 Drawing Sheets

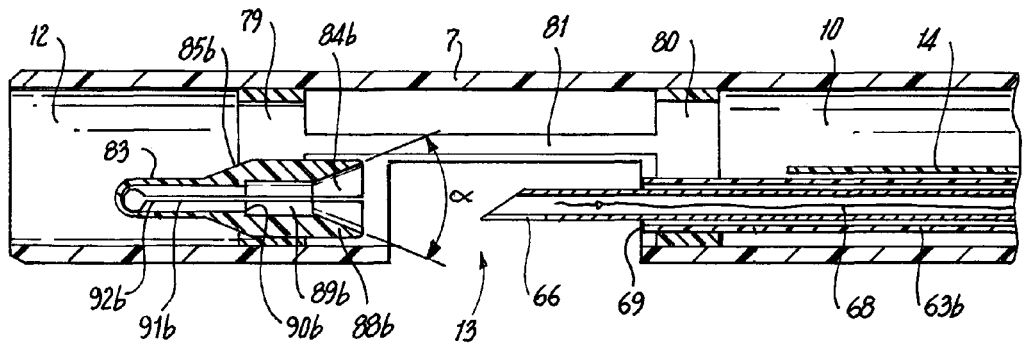
Fig. 13
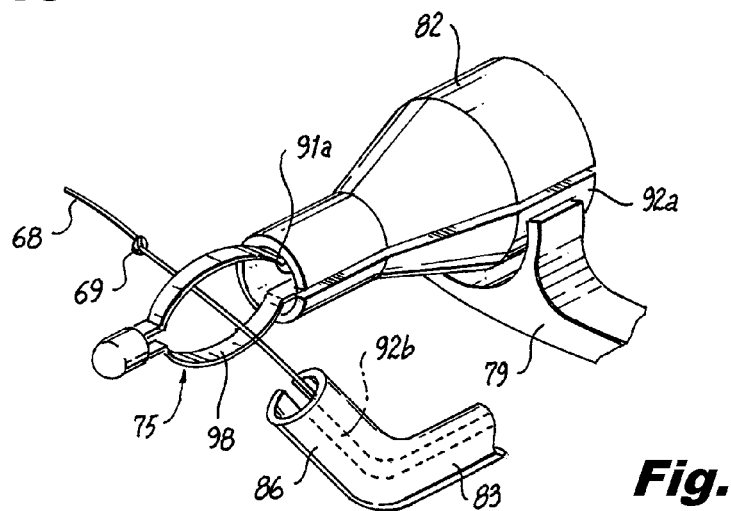
Fig. 14
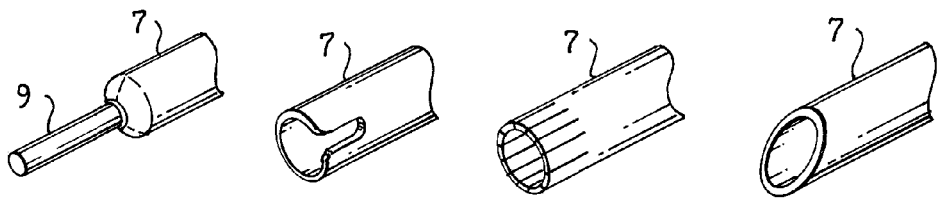
Fig. 15a   Fig. 15b   Fig. 15c   Fig. 15d

Fig. 16
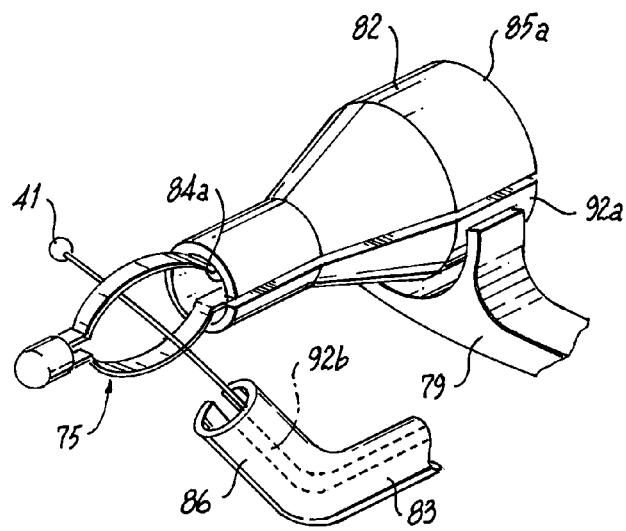
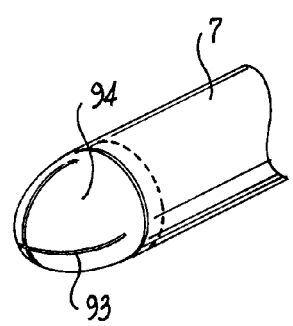
Fig. 17a
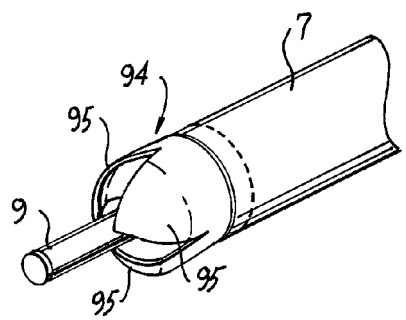
Fig. 17b

Fig. 45
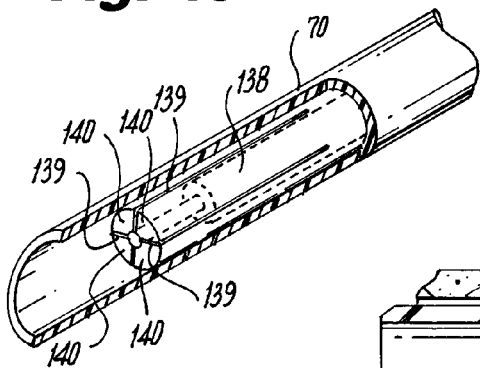
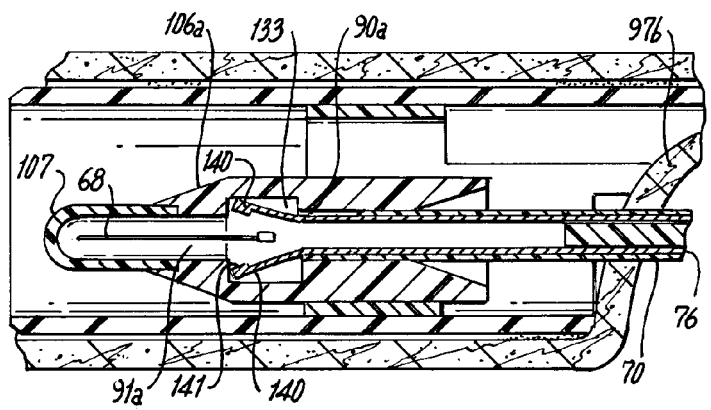
Fig. 46a
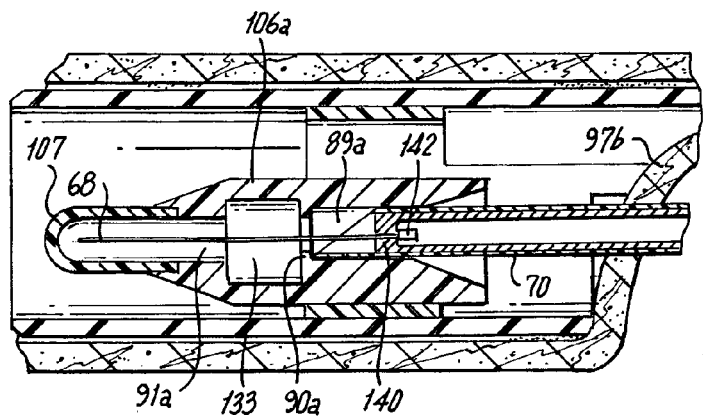
Fig. 46b
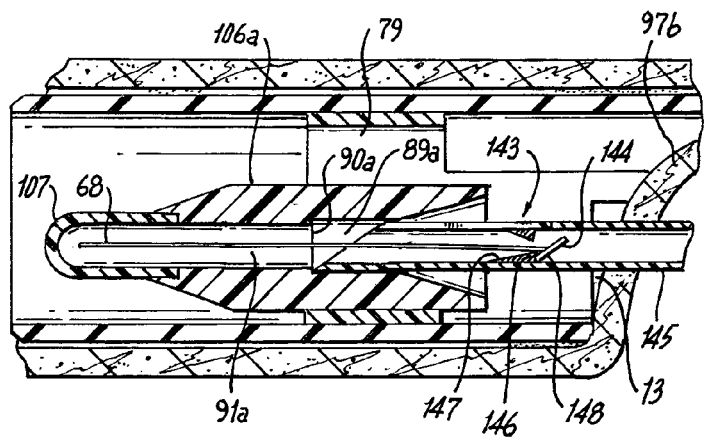
Fig. 47

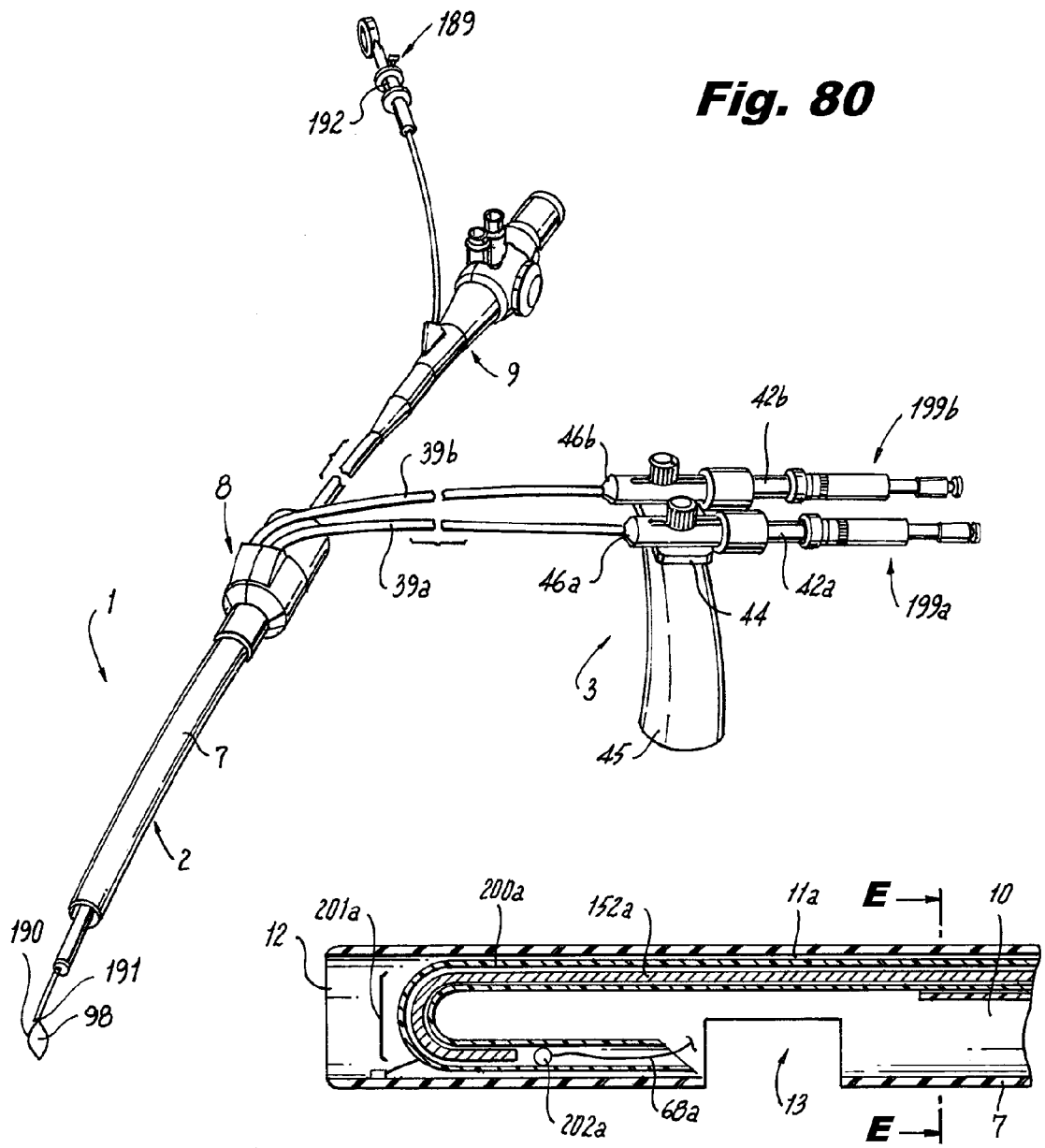
Fig. 80
Fig. 81
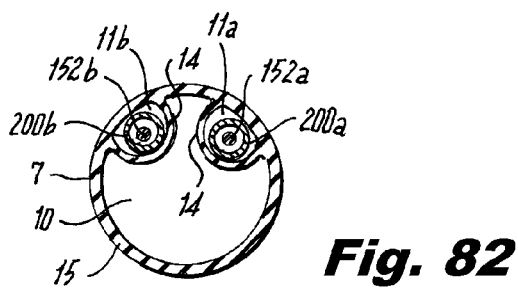
Fig. 82

ENDOSCOPIC INSTRUMENTS FOR SUTURING TISSUES IN A BODY CAVITY

CROSS REFERENCE TO RELATED APPLICATIONS

This application claims priority to U.S. Provisional Application Ser. No. 60/333,380 filed on Nov. 26, 2001, the entire contents of which is incorporated herein by its reference.

BACKGROUND OF THE INVENTION

1. Field of Invention

The present invention relates to a tissue suturing system for suturing tissues in the body by using an endoscope, and more specifically, to a tissue suturing system combined with a flexible endoscope for enabling the formation of an artificial valve to treat gastroesophageal reflux disease (GERD).

2. Description of the Related Art Statement

Currently, in many cases, in-vivo tissue of a patient is sutured through surgical operation. A surgical operation, however, is highly invasive because it naturally requires an incision to the patient's body. Furthermore, it requires post-operative hospitalization, the cost of which can be a heavy burden for the patient. In these circumstances., the development of a low-invasive oral endoscopic procedure that eliminates the need for open surgery is anticipated.

The incidence of GERD has increased recently. The main symptoms of GERD are heartburn and mucosal breaks in the esophagus. Although it is a benign disease, GERD is accompanied by serious pain and often requires treatment. The main cause of GERD is decreased function of the lower esophageal sphincter (LES) at the bottom of the esophagus followed by reflux of acid into the esophagus. GERD is usually treated by administration of acid secretion controlling agent such as proton-pump inhibitor. Moderate GERD will improve and may be treated completely by medication. If, however, the LES function is damaged seriously or if anatomic. problems such as hiatal hernias exist, treatment with medication is less effective, and becomes costly over an extended period of time Therefore, cases of serious GERD are often treated surgically. Effective surgical methods-including Nissen fundoplication or Toupet method are known and applied widely. With this method, the LES is wrapped by the stomach wall to improve its function. This method has been proven highly effective. Recently, laparoscopic surgery techniques were used with this method as a less invasive treatment. Because there are many patients, and GERD is a benign disease, these less invasive treatments are most desirable. One such technique involves the formation of an artificial valve to prevent the reflux of acid.

For example, there is an instrument for suturing in-vivo tissue through an oral endoscopic, the composition of which has been disclosed in the U.S. Pat. No. 5,792,153 as shown in FIG. 99 through FIG. 103. The instrument (a) which can be mounted on an endoscope, comprises a tube (b) that can be connected to the suction source, a cavity (c) to which the tube (b) is joined, a hollow needle (d) inserted in the forceps channel of the endoscope, a tag (g) provided with a lumen and side holes (e and f) that can be incorporated into the needle, a wire (i) with a valve (h) which can move back and forth in the needle (d) and can be mounted to the side hole (e) detachably by a thread (j) tied to the tag (g), and a grasping member (k) which is provided at the tip of the cavity (c) and is easily connected and disconnected to the side hole (f).

With the valve (h) joined to the side hole (e), the tag (g) is inserted into the needle (d). Then, an endoscope, with the instrument (a) mounted on it, is orally inserted into the patient's lumen to suck the tissue (l) to be sutured into the cavity (c). The tissue (l) is then penetrated with the needle (d) that has been thrust out through the endoscope tip. Next, the wire (i) is pushed forward to thrust out the tag (g) through the needle (d) so that the side hole (f) of the tag (g) can be joined to the grasping member (k). The valve (h) is then removed from the side hole (e) so as to pull the wire (i) and the needle (d) into the endoscope. After this, suction is released.

Again, the tissue (l) is sucked into the cavity (c) to be penetrated with the needle (d). Then the valve (h) is joined to the side hole (e) and the grasping member (k) is removed from the opening (f). The valve (h), the tag (g) and the needle (d) are withdrawn and the suction is released. The steps above are repeated as many times as are necessary and then the instrument (a) is removed from the lumen together with the endoscope. When both ends of the thread, which have been pulled out from the body, are tied together and fixed, the suture procedure is terminated. Since the distal end of the endoscope is attached above the instrument, and the cavity is fixed in the vicinity of the distal end of the endoscope in the construction disclosed in U.S. Pat. No. 5,792,153, it is difficult to observe the tissue sucked into the cavity. As the needle cannot be confirmed to have penetrated the desired puncture site before the needle actually punctures the tissue sucked into the cavity, accurate control of the puncture site is extremely difficult. As a result, accurate suturing cannot be achieved, or more stitches are required, thus increasing the treatment time.

Moreover, inability to control the intervals between the stitches will prevent the tissue from being securely sutured with less number of stitches.

In addition, each penetration requires joining the valve (h) and the side hole (e) and releasing the grasping member (k) and the opening (f) and vice versa.

These two operations, required per penetration, will make the treatment procedure very complicated, extending the treatment time as well.

Although the puncture range in a single puncture depends on the size of the cavity, the outer diameter of the entire instrument must inevitably be limited to ease the burden on the patient during insertion. Since the endoscope and the cavity are not aligned in this construction, the size of the cavity must inevitably be limited. If the suture range is larger than the range sucked into the cavity, suturing itself becomes impossible, thus limiting its applicability.

SUMMARY OF THE INVENTION

The first objective of the present invention is to provide a suturing instrument that can accurately suture in-vivo tissue.

The second objective of the present invention is to provide a suturing instrument that enables easy access to the suture area and delicate control of the location of the penetration needle.

The third objective of the present invention is to provide a suturing instrument that enables easy operation and ensures a short treatment time.

The fourth objective of the present invention is to provide a suturing instrument that provides the maximum range for the suturing of tissue in the body.

The fifth objective of the present invention is to provide a suturing instrument that causes the minimum of pain to the patient when inserted into the body.

BRIEF DESCRIPTION OF THE DRAWINGS

FIG. 13 is a vertical cross-sectional view taken along line D-D of FIG. 12.

FIG. 14 is a view illustrating the suture being fed into the needle guide portion at the front end of the overtube.

FIG. 15(a) to FIG. 15(d) and FIG. 17 are external overviews of modification examples of the front end of the overtube.

FIG. 16 is a view illustrating the suture being fed in the modification example of the grip, which is put through one needle.

FIG. 45 is a cross-sectional view illustrating a front end of the needlepoint of another modification example according to the fourth embodiment.

FIGS. 46(a) and 46(b) are views illustrating receiving the suture according to the modification shown in FIG. 45.

FIG. 47 illustrates a partial sectional view of a tissue puncturing system according to a fifth embodiment.

FIG. 80 is an external overview of a tissue puncturing system according to an eleventh embodiment.

FIG. 81 is a vertical cross-sectional view of the front end of the overtube of FIG. 80, which is sectioned on the centerline of the needle.

FIG. 82 is a horizontal cross sectional view taken along the line E-E in FIG. 81.

DESCRIPTION OF THE PREFERRED EMBODIMENTS

Figure 1:
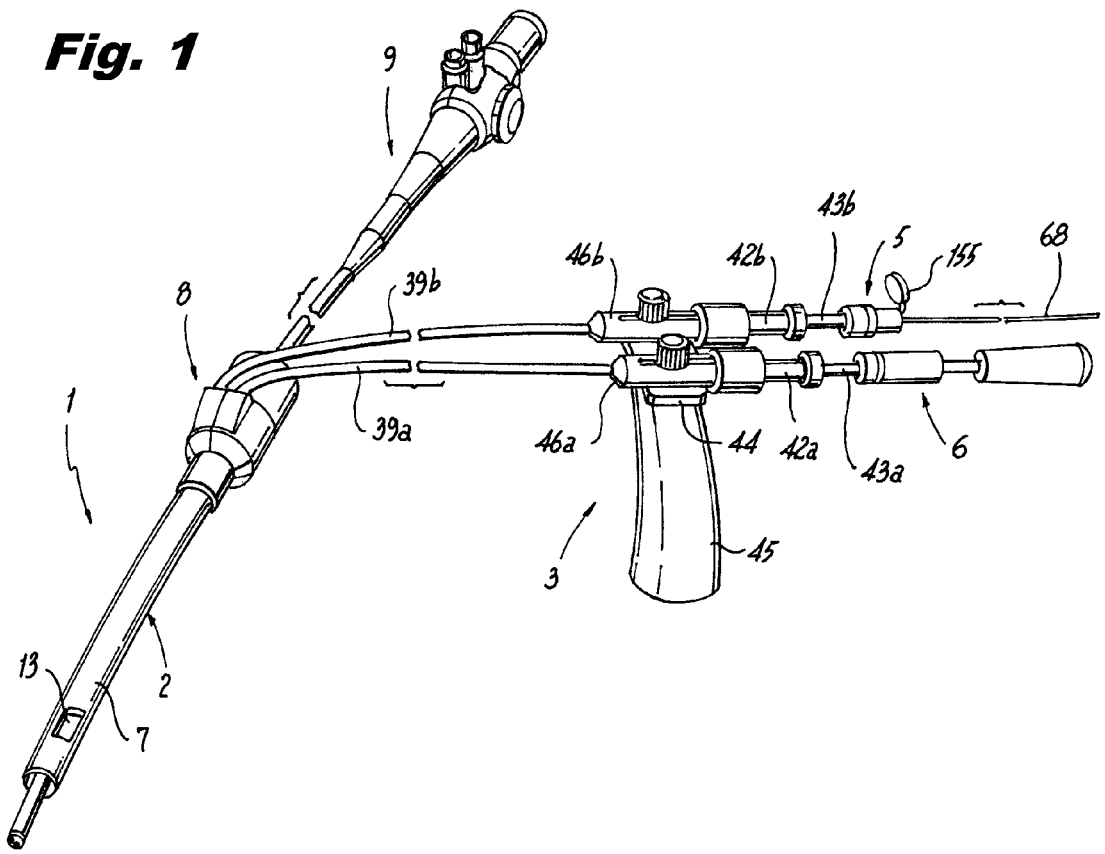
FIG. 1 is an external overview of a tissue puncturing system according to a first embodiment.
Figure 2:
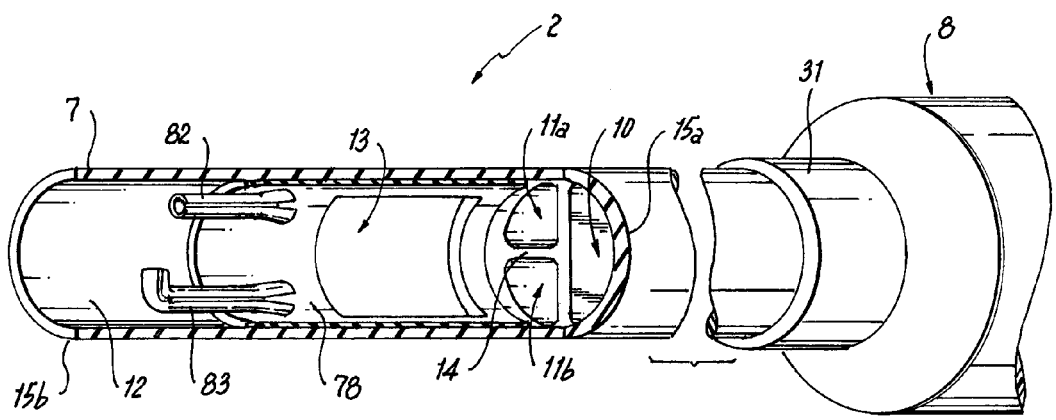
FIG. 2 is a partial cross-sectional view of the overtube of the tissue puncturing system of FIG. 1.
Figure 3:
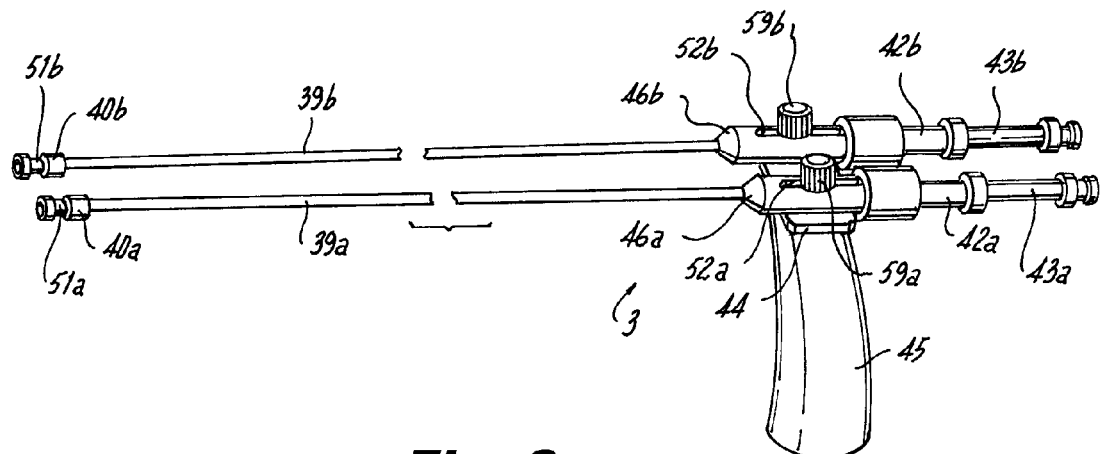
FIG. 3 is an external overview illustrating the operation unit of the tissue puncturing system of FIG. 1.
Figure 4:
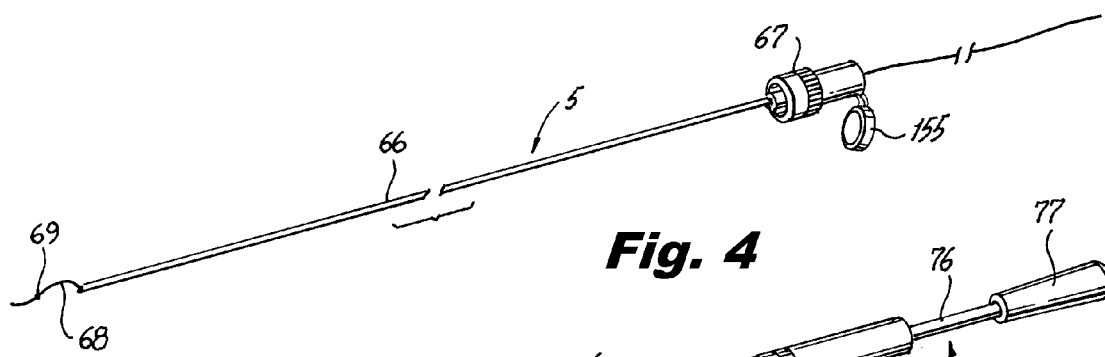
FIG. 4 is an external overview illustrating one of the needles of the tissue puncturing system of FIG. 1.
Figure 5:
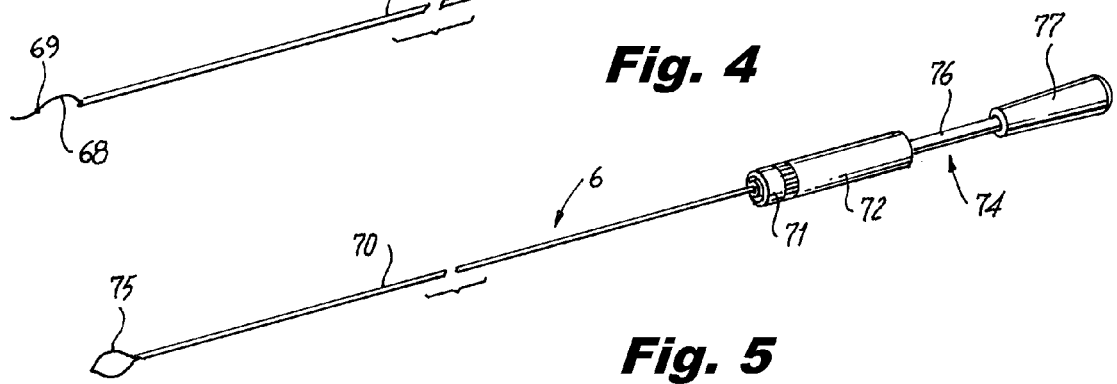
FIG. 5 is an external overview for illustrating another of the needles of the tissue puncturing system of FIG. 1.
Figure 6:
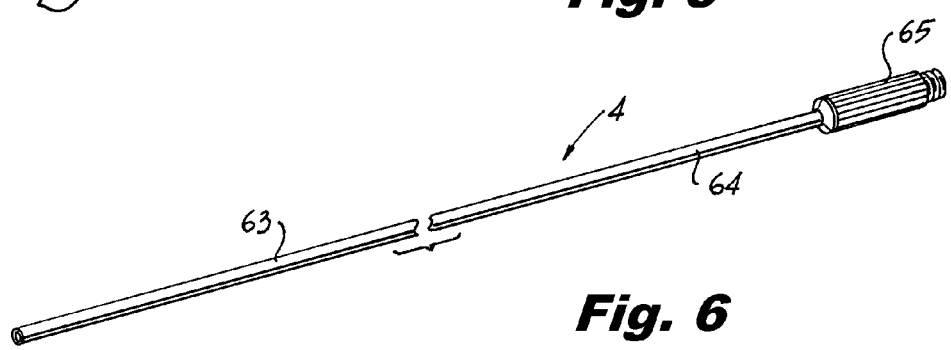
FIG. 6 is an external overview for illustrating the inner sheath of the tissue puncturing system of FIG. 1.
Figure 7:
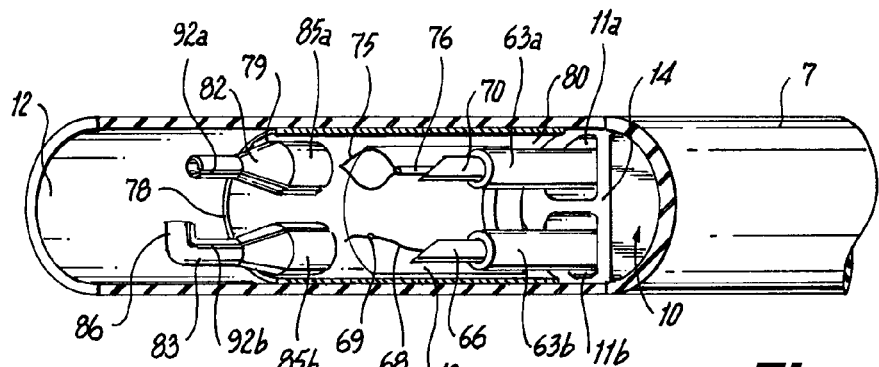
FIG. 7 is a partial cross-sectional view of the overtube of the tissue puncturing system of FIG. 1.
Figure 8:
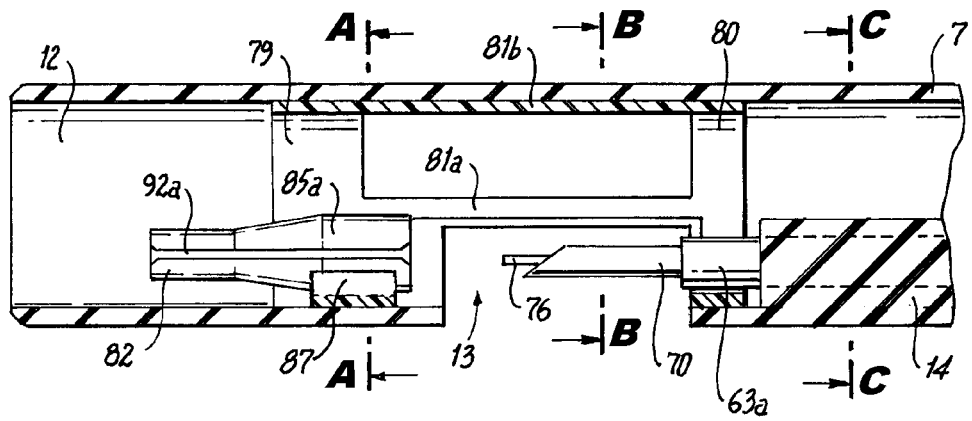
FIG. 8 is a vertical cross-sectional view of the overtube of FIG. 7.
Figure 9:
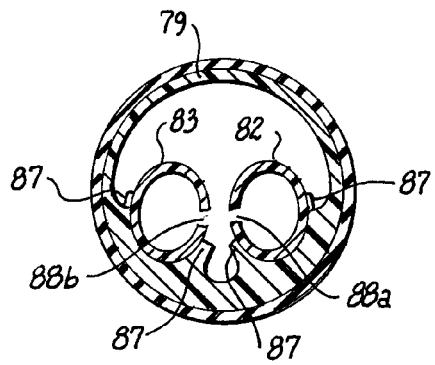
FIGS. 9, 10, and 11 are cross-sectional views taken along lines A-A, B-B, and C-C, respectively, of FIG. 8.
Figure 10:
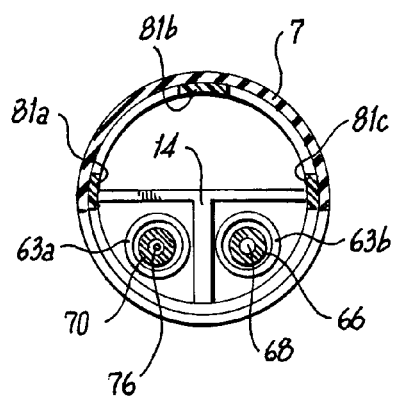
Figure 11:
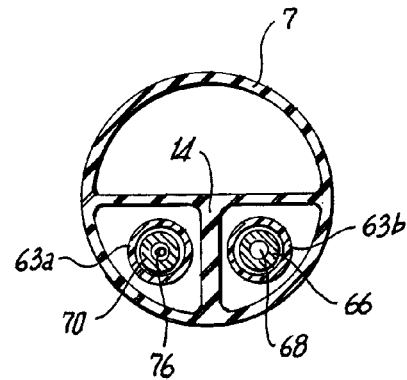
Figure 12:
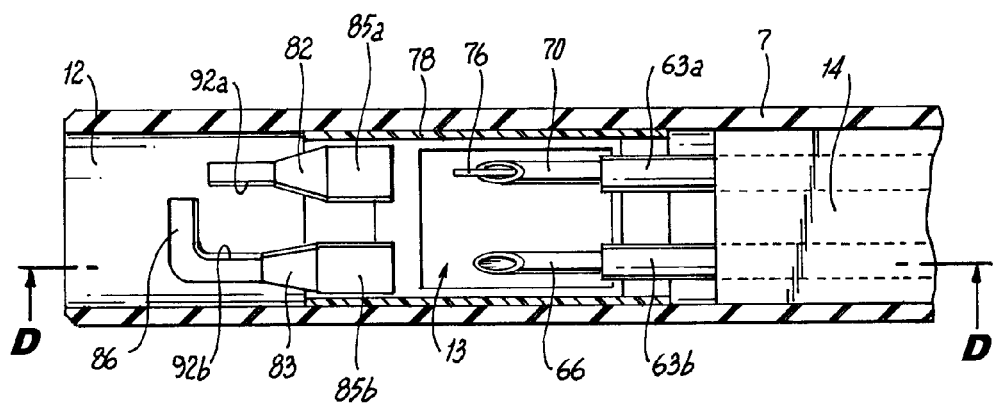
FIG. 12 is a vertical cross-sectional view of the overtube of FIG. 7 that is orthogonal to the view shown in FIG. 8.
Figure 18:
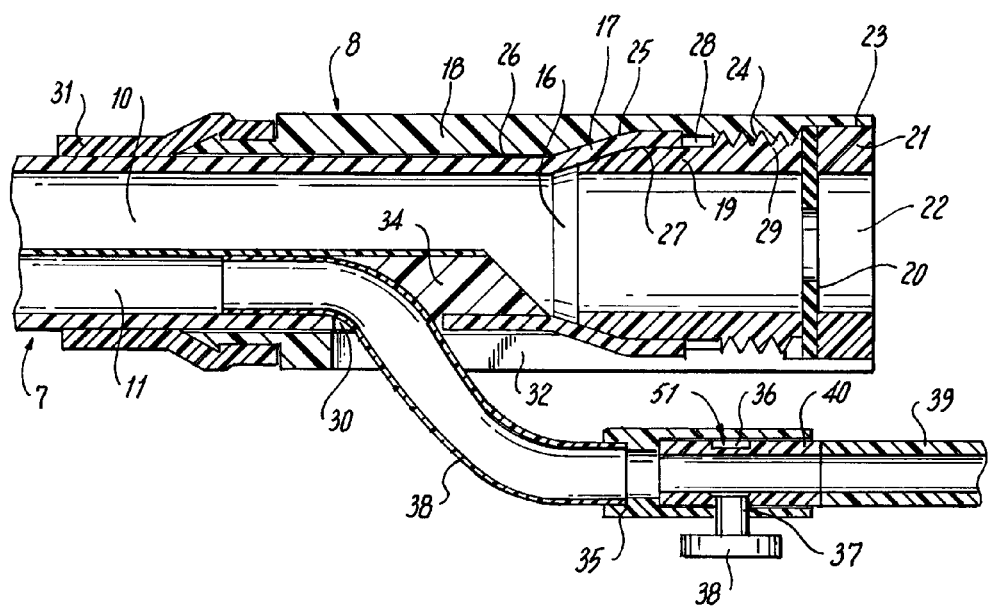
FIG. 18 is a vertical cross-sectional view of the proximal side of the overtube.
Figure 19:
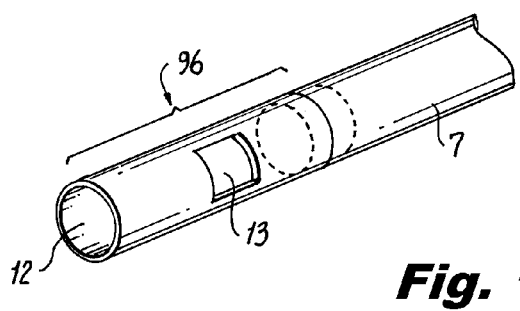
FIG. 19 is an external overview of a modification example, in which the front end of the overtube is detachable.
Figure 20:
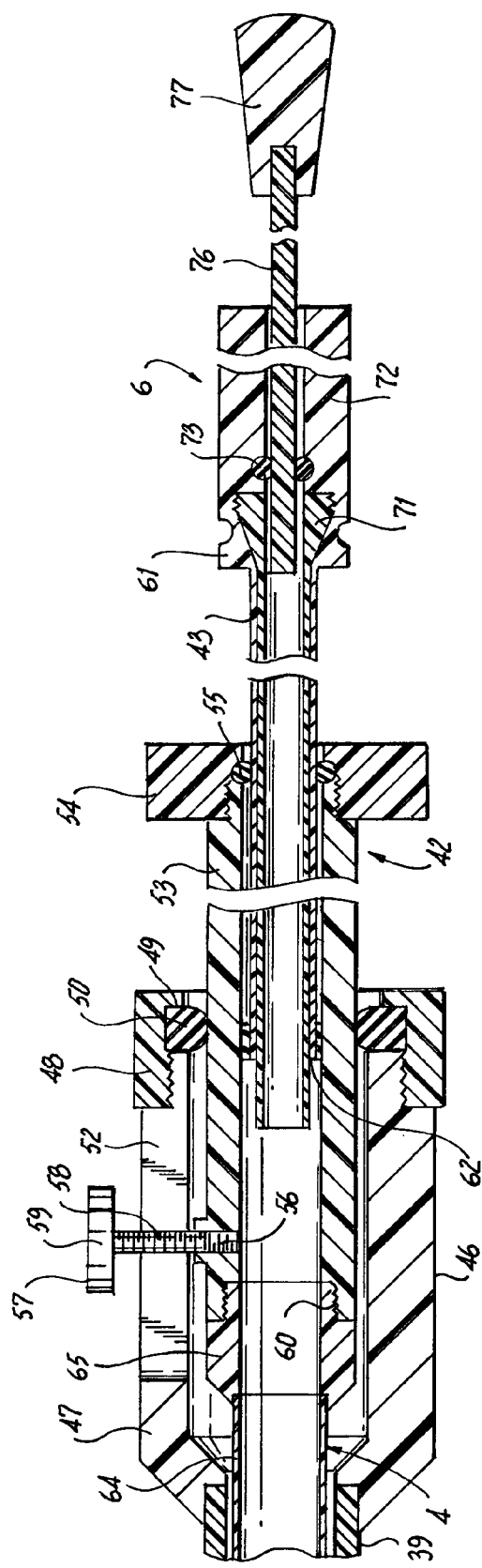
FIG. 20 is a vertical cross-sectional view of the slider on the operation unit.
Figure 21:
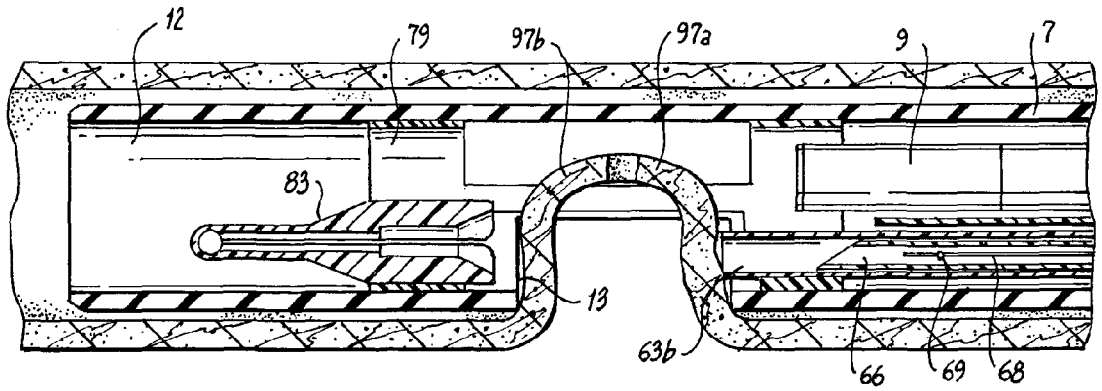
FIG. 21 is an operational view illustrating the inner sheath being struck against the tissue to be put in a suture.
Figure 22:
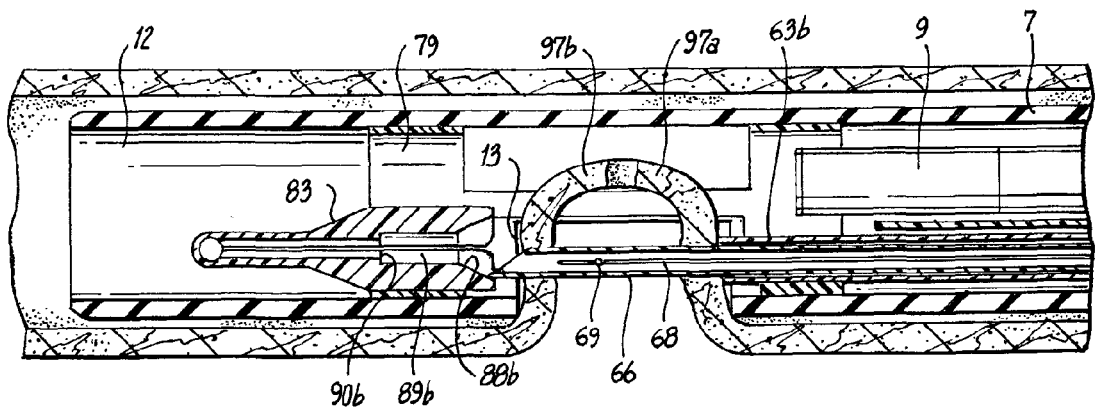
FIG. 22 is an operational view illustrating the tissue to be put in a suture being punctured by the needle.
Figure 23:
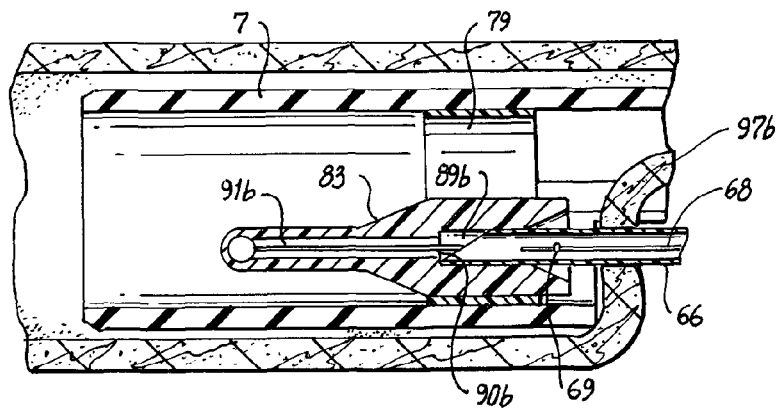
FIG. 23 is an operational view illustrating the needle being struck against the needle guide.
Figure 26:
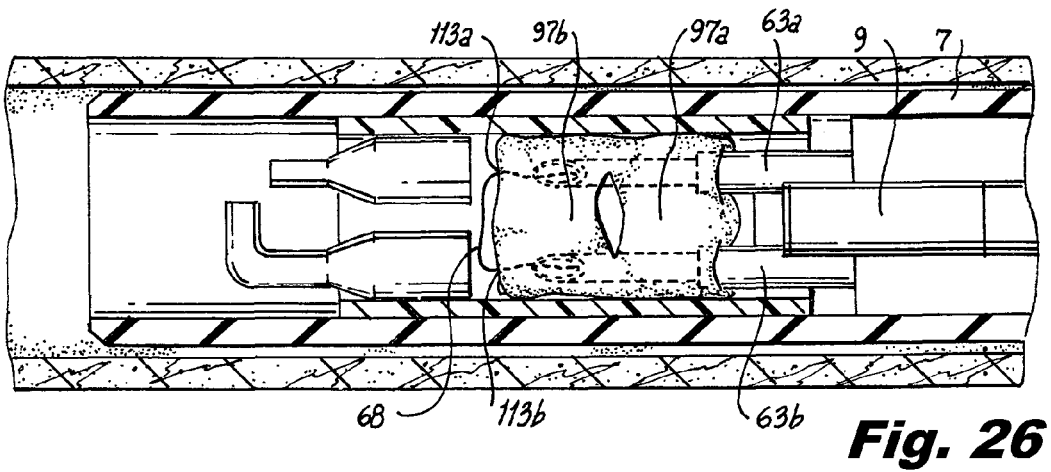
Figure 27:
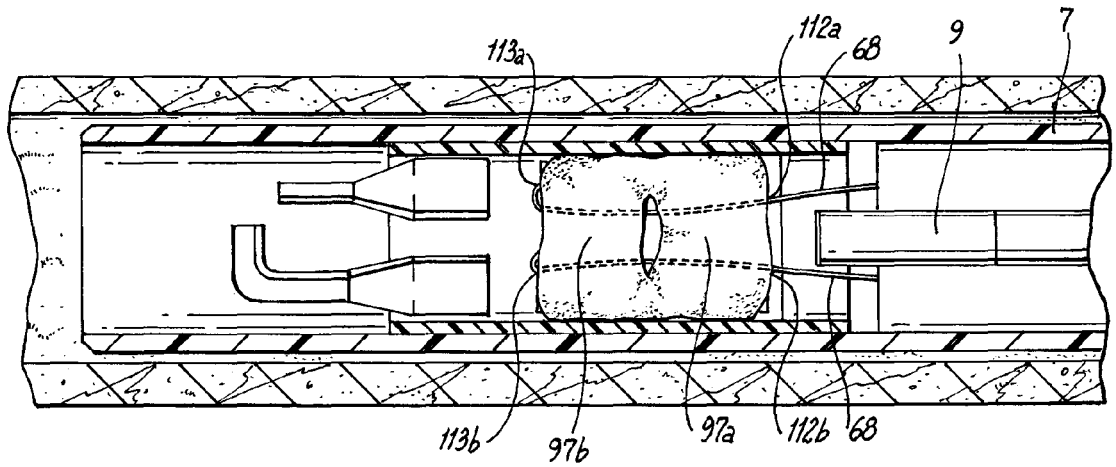
Figure 28:
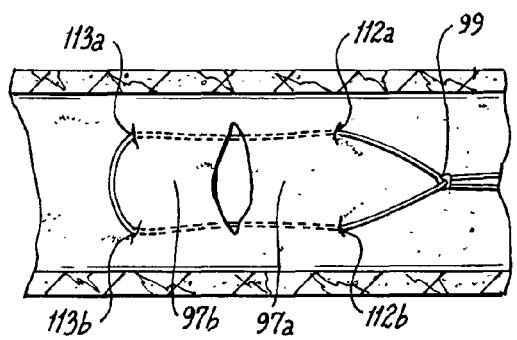
FIG. 28 is an operational view illustrating the knot of the suture being pushed forward.
Figure 29:
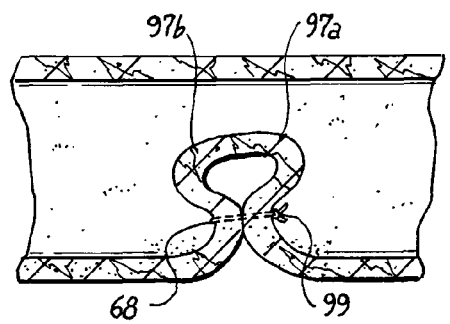
FIG. 29 is a view illustrating the tissue being put in a suture.
Figure 95:
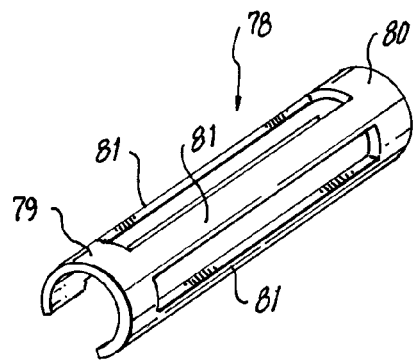
FIG. 95 is an external overview of the modification example of the reinforcement member that is located at the front end of the overtube.
Figure 96:
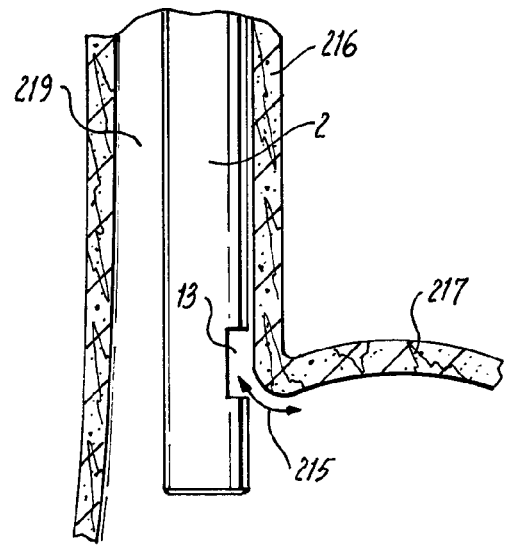
FIGS. 96 to 98 are operational views illustrating the artificial valve being formed at a stomach cardia of a patient of a gastroesophageal reflux disease by using the tissue puncturing system.
Figure 97:
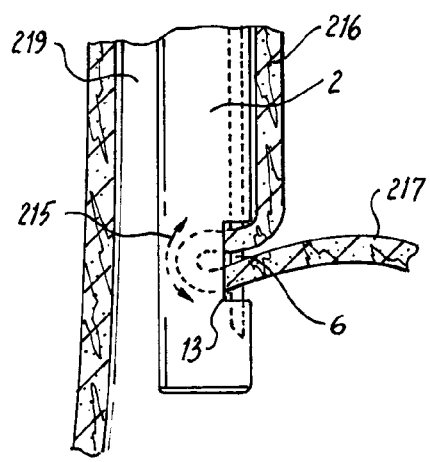
Figure 98:
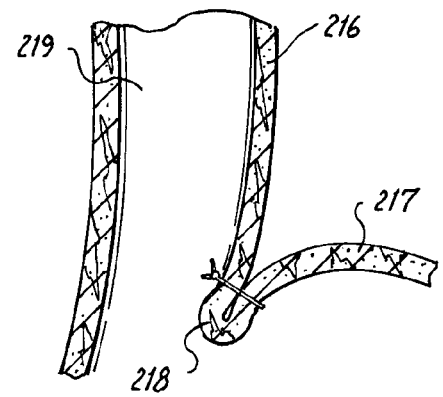
Figure 99:
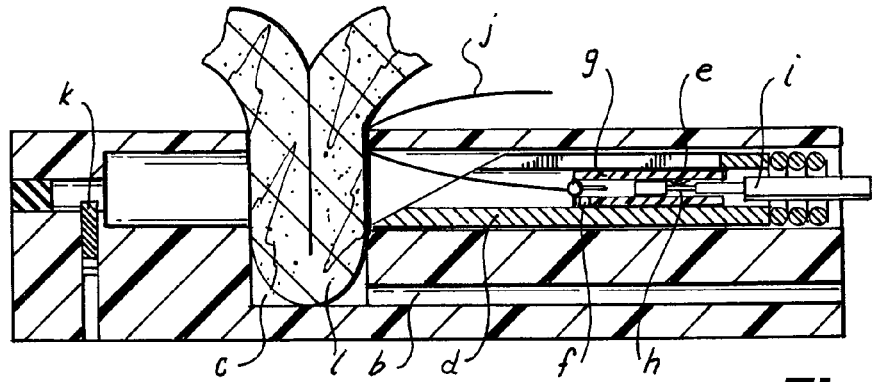
FIGS. 99 through 103 illustrate a prior art instrument for suturing in-vivo tissue through an oral endoscopic.
Figure 100:
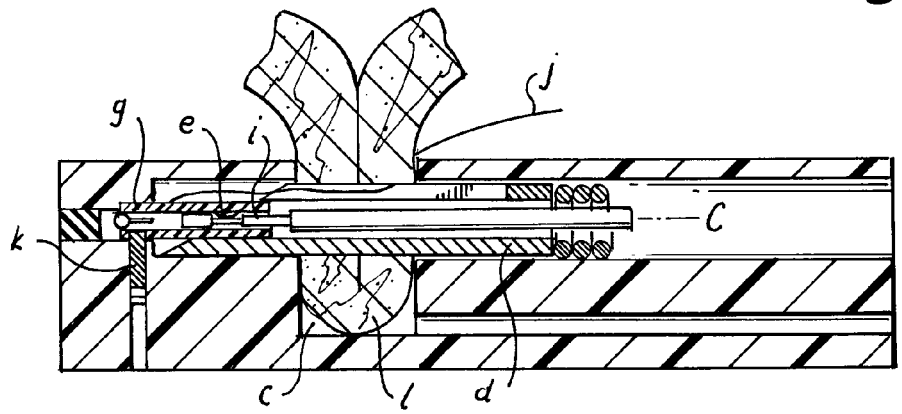
Figure 101:
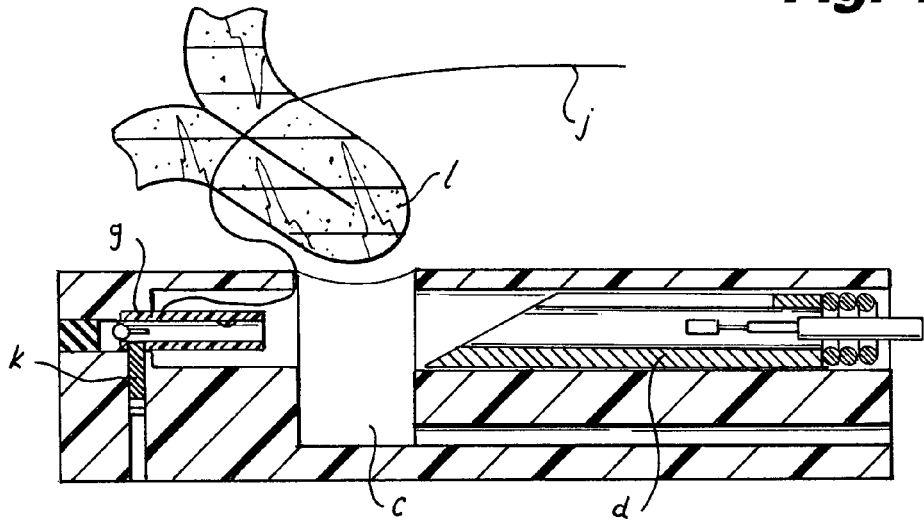
Figure 102:
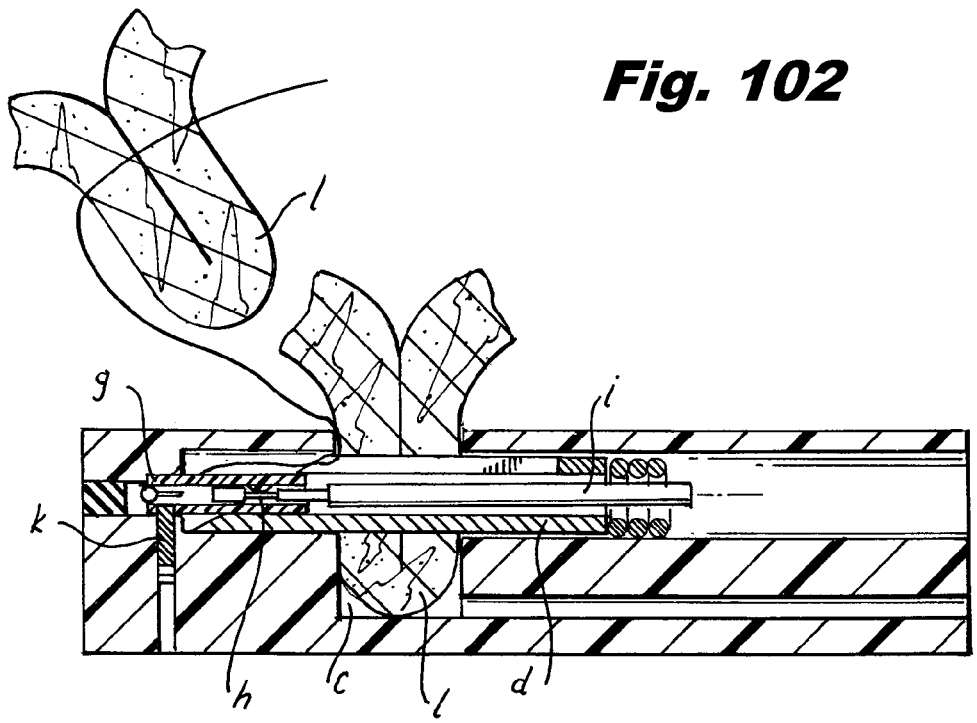
Figure 103:
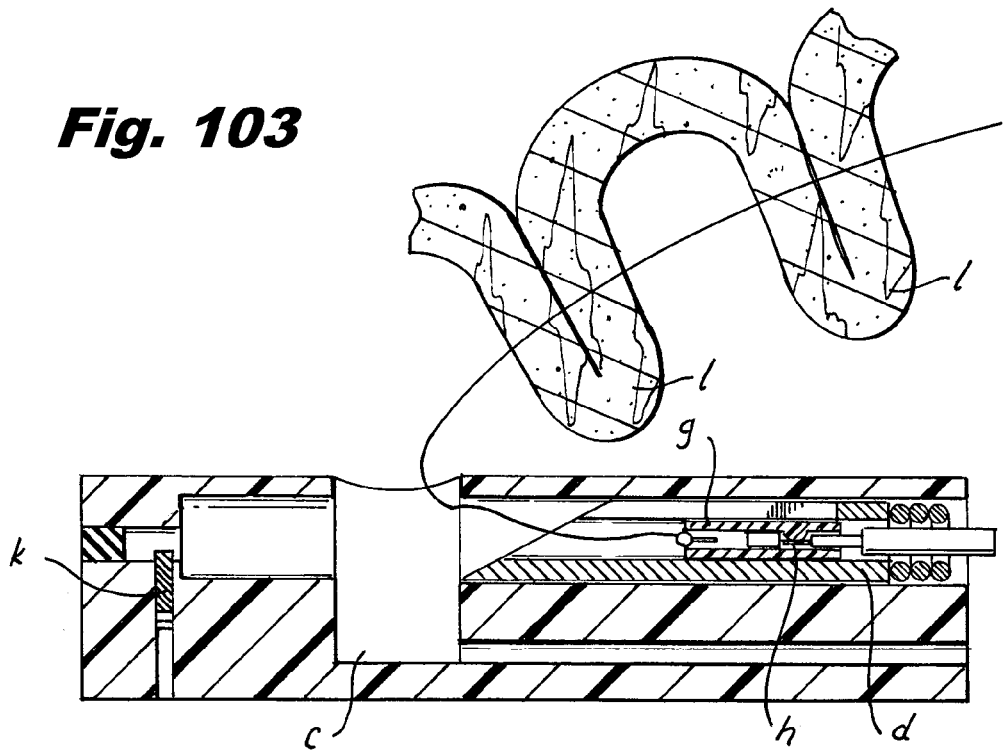

A first embodiment of the tissue puncturing system will now be described with reference to FIGS. 1 through 29, 82, and 95 through 98. FIG. 1 is an external overview of the tissue puncturing system. FIGS. 2 and 7 are partial cross-sectional views of the overtube. FIG. 3 is an external overview for showing only the operation unit. FIG. 4 is an external overview for showing only one of the needles. FIG. 5 is an external overview for showing only other one of the needles. FIG. 6 is an external overview for showing only the inner sheath. FIG. 8 is a vertical cross-sectional view of the overtube in FIG. 7. FIGS. 9, 10, and 11 are cross-sectional views taken along lines A-A, B-B, and C-C in FIG. 8 respectively. FIG. 12 is a vertical cross-sectional view that is orthogonal to FIG. 8. FIG. 13 is a vertical cross-sectional view taken along line D-D in FIG. 12. FIG. 14 is a view for showing a state such that the suture is fed into the needle guide portion at the front end of the overtube. FIG. 15 (a) to FIG. 15 (d) and FIG. 17 are external overviews of the modification examples of the front end of the overtube. FIG. 16 is a view for showing a state such that the suture is fed in the modification example of the grip, which is put through one needle. FIG. 18 is a vertical cross-sectional view of the proximal side of the overtube. FIG. 19 is an external overview of the modification example, in which the front end of the overtube is detachable. FIG. 20 is a vertical cross-sectional view of the slider on the operation unit. FIG. 21 is an operational view for showing a state such that the inner sheath is struck against the tissue to be put in a suture. FIG. 22 is an operational view for showing a state such that the tissue to be put in a suture is punctured by the needle. FIG. 23 is an operational view for showing a state such that the needle is struck against within the needle guide. FIG. 24 to FIG. 27 are operational views for showing a state such that the suture is fed between two needles. FIG. 28 is an operational view for showing a state such that the knot of the suture is pushed forward. FIG. 29 is a view for showing a state such that the tissue is put in a suture. FIG. 82 is a cross-sectional view, which shows the embodiment, however, which is also the modification example of the first embodiment with respect to the arrangement of the endoscope lumen and the needle lumen within the overtube. FIG. 95 is an external overview of the modification example of the reinforcement member that is located at the front end of the overtube. FIG. 96 to FIG. 98 are operational views for showing a state such that the artificial valve is formed at a stomach cardia of a patient of a gastroesophageal reflux disease by using the tissue puncturing system.

The tissue puncturing system 1 comprises an overtube 2, operation unit 3, inner sheaths 4a and 4b (which is not shown in FIG. 1), needles 5 and 6, and endoscope 9. As shown in FIG. 2, the overtube 2 comprises a sheath section 7 and endoscope insertion section 8. The sheath section 7 comprises an endoscope lumen 10 through which the endoscope may be inserted by sliding, and two needle lumens 11a and 11b through which the inner sheaths 4a and 4b are inserted, and has the flexibility to follow the curvature of the endoscope 9. The endoscope lumen 10 and the needle lumens 11a and 11b are formed in an outer wall 15a and bulkhead 14. The endoscope lumen 10 and the needle lumens 11a and 11b merge at a position a constant distance L (which is not shown in FIGS.) from the distal end of the sheath section 7 toward the proximal side and become single treatment lumen 12 onward from said position toward the distal end. The distance L is desirably between 30 and 100 mm. The treatment lumen 12 is surrounded by the outer wall 15b.

The sheath section 7 is formed of relatively flexible plastic material with a high transparency such as polyurethane, vinyl chloride, polyurethane elastomer, polystyrene elastomer, or polyolefine elastomer, and the outside of the sheath section 7 may be observed through the sheath section 7 via the endoscope 9 inserted into the endoscope lumen 10. While the entire sheath section 7 is preferably transparent, it need not be transparent except for the portion 5 cm from the distal side and the portions cm from the proximal side of the side opening 13. The outer diameter of the sheath section 7 is of a size that can be inserted into the body of the patient and is approximately 10 to 25 mm and preferably approximately 15 to 18 mm.

The inner diameters of the endoscope lumen 10 and needle lumens 11a and 11b may be of any size which enables passage of the endoscope 9 and inner sheaths 4a and 4b respectively, and they may take any shape as shown in FIGS. 11 and 82. The thickness of the bulkhead 14 and outer walls 15a and 15b can be approximately 0.2 to 3 mm and preferably approximately 0.5 to 1.5 mm. The distal end of the sheath section 7 is desirably flexible for ease of insertion into the patient's body and may be made flexible by making the thickness of the outer wall 15b thinner than the outer wall 15a. The needle lumens 11a and 11 b extend in the sheath section 7 in a substantially parallel fashion. The center distance between the needle lumens 11a and 11b is set constant, and as described hereinafter, the distal ends of the needles 5 and 6 inserted through the needle lumens 11a and 11b are set to a constant distance in the range of 5 to 20 mm. A side opening 13 is provided on the outer wall 15b toward the distal side from the distal openings of the endoscope lumen 10, and needle lumens 11a and 11b. The distance between the distal openings of the endoscope lumen 10, and needle lumens 11a and 11b and the proximal end of the side opening 13 is desirably approximately 5 mm. The side opening 13 is disposed so that its center axis in a longitudinal direction is positioned in the middle between the needle lumens 11a and 11b. Although the side opening 13 is desirably rectangular in shape extending in a longitudinal direction as shown in FIG. 2, it may be ellipsoid or circular. When the side opening 13 is rectangular, the corners may be rounded. The length of the side opening 13 may be 5 to 30 mm and desirably approximately 10 to 20 mm. The width of the side opening 13 may be 3 to 23 mm and desirably approximately 13 to 16 mm.

It is preferable that markings are provided around the periphery of the side opening 13 using a color such as blue or green that can readily identified when in the body, so that the side opening 13 may be readily recognized in endoscopic images. The distal end of the sheath section 7 desirably has a shape that facilitates insertion into the body. It may be tapered as shown in FIG. 15 (a). It may have a cutout on part of the distal periphery as shown in FIG. 15 (b). It may have strip-like cuts all around the distal periphery as shown in FIG. 15 (c). The end may be diagonally cut off as shown in FIG. 15 (d).

The proximal side of the endoscope lumen 10 and needle lumens 11a and 11b are situated approximately 5 to 30 mm from the proximal end of the sheath section 7 toward the distal end and form the sheath connecting part 17 having a connecting lumen 16. Sheath slits 30a and 30b that are connected to the needle lumens 11a and 11b are provided in the vicinity of the proximal sides of the needle lumens 11a and 11b. The endoscope insertion section 8 is connected to the proximal end of the sheath section 7. As shown in FIG. 18, the endoscope insertion section 8 comprises a retainer member 18, sheath fixing member 19, valve 20, and valve fixing member 21, and an endoscope insertion port 22 is formed on its proximal side. The retainer member 18 is an annular member having an internal channel through it, and a larger diameter part 23, female screw thread 24, tapered part 25, and smaller diameter part 26 are provided on the internal surface of the retainer member 18. The inner diameter of the smaller diameter part 26 is slightly larger than the outer diameter of the sheath section 7 as to allow the sheath section 7 to pass through. Longitudinally extending slits 32a and 32b are provided on the retainer member 18.

The slits 32a and 32b are sized and positioned to open toward the sheath slits 30a and 30b when the retainer member 18 is mounted on the sheath section 7. The distance between and the width of the slits 32a and 32b are desirably equal to or larger than those of sheath slits 30a and 30b. The sheath fixing member 19 is. cylindrical in shape, having an internal channel through which the endoscope 9 may be inserted. Distal tapered part 27, straight part 28, and proximal male screw thread 29 are provided on the outer surface of the sheath fixing member 19. The taper angle of the distal tapered part 27 is substantially the same as for the tapered part 25. The distal tapered part 27 and straight part 28 of the retainer member 18 are pushed into the connecting lumen 16, and in this state, the proximal male screw thread 29 is engaged with and tightened into the female screw thread 24. The retainer member 18 is pushed into the sheath connecting part 17 so that the slits 32a and 32b align with the sheath slits 30a and 30b.

As a result, the sheath connecting part 17 is held between the tapered part 25 and the distal tapered part 27 and fixed on the retainer member 18. The valve 20 is fitted on the larger diameter part 23 on the proximal side of the sheath fixing member 19. A valve fixing member 21 is fitted on the proximal side of the valve 20 and fixed to the larger diameter part 23 using an adhesive or the equivalent. The valve 20 is held between the sheath fixing member 19 and the valve fixing member 21 and fixed to the retainer member 18. The valve 20 has an annular shape and is formed from rubber such as silicone rubber or fluoro-rubber or a thermoplastic elastomer. The inner diameter of the valve 20 is smaller than the outer diameter of the endoscope 9 so that air tightness is maintained between the valve 20 and the endoscope 9 when the endoscope 9 is inserted through the valve 20. The thickness of the valve 20 is approximately 0.5 to 5 mm and desirably approximately 1 mm. The valve fixing member 21 has an internal channel larger than the outer diameter of the endoscope 9, which is slightly smaller than the inner diameter of the larger diameter part 23. The valve fixing member 21 and the larger diameter part 23 may be threaded and screwed together. Although the retainer member 18, sheath fixing member 19, and valve fixing member 21 are formed of various metal materials such as stainless steel or aluminum, or various plastic materials such as polypropylene, ABS polycarbonate, polyacetal, or polysulfone, they are desirably to be made of a lightweight and rigid plastic material.

A protective tube 31 is fixed on the distal end of the retainer member 18. The protective tube 31 extends to the distal end of the retainer member 18, covering the sheath section 7 to prevent the sheath section 7 from kinking at the distal end of the retainer member 18. The protective tube 31 may be formed of various plastic materials such as polyurethane, PVC, silicone, fluorocarbon resin, or polyolefine resin. The protective tube 31 may be a heat-shrinking tube. The length from the distal end of the sheath section 7 to the distal end of the protective tube 31 is approximately 0.3 to 2 meters and desirably 1 meter. In addition, respective connecting pipes 33a and 33b are fixed via the sheath slits 30a and 30b, and slits 32a and 32b into the needle lumens 11a and 11b using adhesive or the like. The connecting pipes 33a and 33b are curved in an S-shape as shown in FIG. 18 or bent into an L-shape. The connecting pipes 33a and 33b may be formed of metal such as stainless steel. The inner diameters are larger than the outer diameters of inner sheaths 4a and 4b described hereafter so that inner sheaths 4a and 4b may be smoothly inserted through them.

The portion between the distal ends of the sheath slits 30a and 30b, and the proximal end of the needle lumens 11a and 11b is a sealed part 34, which is filled with adhesive agent or filler to maintain air-tightness in the sheath section 7 at the sheath slits 30a and 30b. Desirably, the proximal end of the sealed part 34 is tapered so that the distal end of the endoscope 9 may be inserted in the overtube 2 without becoming hooked by the sealed part 34. Connecting ports 35a and 35b are connected to the proximal end of the connecting pipes 33a and 33b. The connecting ports 35a and 35b have internal channels 36a and 36b so as to allow the inner sheaths 4a and 4b to pass through smoothly. Screw holes 37a and 37b are provided in the sidewalls of the connecting ports 35a and 35b to accept fixing screws 38a and 38b. The distal plugs 40a and 40b of the connecting sheaths 39a and 39b of the operation unit 3 described hereafter are detachable, being fixed to internal channels 36a and 36b with the fixing screws 38a and 38b.

As shown in FIG. 3, the operation unit 3 comprises connecting sheaths 39a and 39b, inner sheath sliders 42a and 42b, needle sliders 43a and 43b, base 44, grip 45, and slider receivers 46a and 46b. The grip 45 is fixed on the bottom side of the base 44. The grip 45 is situated on the central (longitudinal) axis of the base 44. The grip 45 may be of any shape which is easily grasped by the operator, but is preferably moderately curved towards the proximal end. Two slider receivers 46a and 46b are fixed at suitable spacings on the upper side of the base 44. The slider receivers 46a and 46b are fixed at equal distances from the central (longitudinal), axis. The slider receivers 46a and 46b are preferably disposed in parallel or in a position in which the distance between the proximal ends is greater than the distance between the distal ends. As shown in FIG. 20, the slider receivers 46a and 46b have annular housings 47a and 47b, to the proximal end of which annular rings 48a and 48b are connected.

The outer surfaces of the housings 47a and 47b at their proximal ends and the inner surfaces of the distal ends of the rings 48a and 48b are provided with male and female screw threads respectively which mate with each other. The inner surfaces of the rings 48a and 48b are provided with O-ring seats 49a and 49b. O-rings 50a and 50b are held between the proximal ends of the housings 47a and 47b, and the O-ring seats 49a and 49b. The housings 47a and 47b have distal ends connected to the connecting sheaths 39a and 39b. The connection between the housings 47a and 47b, and the connecting sheaths 39a and 39b may or may not be detachable. The connecting sheaths 39a and 39b are hollow and flexible.

The connecting sheaths 39a and 39b may be formed of various plastic tubes such as fluorocarbon resin, polyethylene, polyamide, polyimide, polyurethane, various thermoplastic elastomers or metal coils. The connecting sheaths 39a and 39b may be made of metal coils covered by plastic tubes. Plastic tubes containing metal mesh may be used to prevent kinking. The connecting sheaths 39a and 39b desirably have inner diameter of approximately 1 to 2.5 mm, outer diameter of approximately 1.5 to 3 mm, and length of approximately 0.3 to 1 meter. Distal plugs 40a and 40b are fixed on the distal ends of the connecting sheaths 39a and 39b. The inner diameters of the distal plugs 40a and 40b are generally the same as for connecting sheaths 39a and 39b. As shown in FIG. 18, annular grooves 51a and 51b are provided on the periphery of the distal plugs 40a and 40b. When the distal plugs 40a and 40b are fitted in the internal channels 36a and 36b of the connecting ports 35a and 35b and tightened with the fixing screws 38a and 38b, the distal ends of the fixing screws 38a and 38b come into the annular grooves 51a and 51b. Referring to the explanation of FIG. 20, slits 52a and 52b extend longitudinally from the proximal end to the vicinity of the distal end on the sidewalls of the housings 47a and 47b. Inner sheath sliders 42a and 42b are detachable from the internal channel of the housings 47a and 47b. The inner sheath sliders 42a and 42b comprise annular inner sheath housings 53a and 53b, inner sheath rings 54a and 54b connected to the proximal ends of the inner sheath housings 53a and 53b, and O-rings, 55a and 55b held between the proximal ends of the inner sheath housings 53a and 53b, and the inner sheath rings 54a and 54b. The inner sheath housings 53a and 53b and the inner sheath rings 54a and 54b are connected in the same manner as for the slider receivers 46a and 46b.

The outer diameters of the inner sheath housings 53a and 53b are slightly larger than the inner diameters of the O-rings 50a and 50b, and the outer surfaces of the inner sheath housings 53a and 53b come into close contact with the O-rings 50a and 50b and the inner sheath sliders 42a and 42b disposed in the housings 47a and 47b, thus maintaining air-tightness between them. Screw holes 56a and 56b are provided in the sidewalls of the inner sheath housings 53a and 53b to accept fixing screws 57a and 57b. The fixing screws 57a and 57b have threads 58a and 58b and screw knobs 59a and 59b. Part of the threads 58a and 58b respectively penetrates the slits 52a and 52b. When the screw knobs 59a and 59b are loosened, the bottom surfaces of the screw knobs 59a and 59b lie away from the outer surfaces of the housings 47a and 47b, thus allowing the threads 58a and 58b to slide in the slits 52a and 52b. In this state, the inner sheath housings 53a and 53b can also slide in the housings 47a and 47b.

When the threads 58a and 58b are tightened, the bottom surfaces of the screw knobs 59a and 59b contact the outer surfaces of the housings 47a and 47b to fix the inner sheath housings 53a and 53b against the housings 47a and 47b. The rings 48a and 48b, and O-rings 50a and 50b are previously mounted on the periphery between the fixing screws 57a and 57b of the inner sheath sliders 42a and 42b, and the inner sheath rings 54a and 54b. When the rings 48a and 48b are removed, the inner sheath sliders 42a and 42b become detachable from the housings 47a and 47b. The sliding stroke of the inner sheath sliders 42a and 42b is determined by the length of the slits 52a and 52b and is desirably approximately 10 to 30 mm. Connecting female screw threads 60a and 60b are cut on the inner surfaces at the distal end of the inner sheath housings 53a and 53b to accept inner sheaths 4a and 4b respectively. The needle sliders 43a and 43b slide in the internal channels of the inner sheath sliders 42a and 42b. The needle sliders 43a and 43b are provided with internal channels, and needle connecting ports 61a and 61b having outer diameters larger than other parts are formed at its proximal end. The inner surfaces of the needle connecting ports 61a and 61b are luer-tapered. Annular stoppers 62a and 62b are fixed on the proximal periphery of the needle sliders 43a and 43b. The outer diameter of the stoppers 62a and 62b is larger than the inner diameter of the O-rings 55a and 55b so that the stoppers 62a and 62b come into contact with and are stopped by the O-rings 55a and 55b when the needle sliders 43a and 43b are withdrawn toward the proximal end.

When the needle sliders 43a and 43b are advanced toward the distal end, the distal end surfaces of the needle connecting ports 61a and 6b butt up against the proximal surfaces of the inner sheath rings 54a and 54b and are stopped. The sliding stroke of the needle sliders 43a and 43b are desirably approximately 20 to 80 mm. The outer diameters of the needle sliders 43a and 43b are slightly larger than the inner diameters of the O-rings 55a and 55b except for the needle connecting ports 61a and 61b so as to maintain air-tightness between them. The O-rings 50a, 50b, 55a, and 55b may be formed from rubber such as silicone rubber or fluoro-rubber or a thermo plastic elastomer. While the members constituting the operation unit 3 except the connecting sheaths 39a and 39b and O-rings 50a, 50b, 55a, and 55Sb maybe formed from various metals such as stainless steel and aluminum or various plastic materials such as polypropylene, ABS, polycarbonate, polyacetal, or polysulfone, desirably they should be made of a lightweight and rigid plastic material.

As shown in FIGS. 6 and 20, the inner sheaths 4a and 4b comprise tubes 63a and 63b, inner sheath pipes 64a and 64b, and connecting male screws 65a and 65b. The tubes 63a and 63b are hollow and flexible and may be formed of various plastic tubes such as fluorocarbon resin, polyethylene, polyamide, polyimide, polyurethane, various thermoplastic elastomers or metal coils. The tubes 63a and 63b may be plastic tubes containing metal mesh to prevent kinking. The inner sheath pipes 64a and 64b are connected to the proximal ends of the tubes 63a and 63b. The connecting male screw threads 65a and 65b are connected to the proximal ends of the inner sheath pipes 64a and 64b. The connecting male screw threads 65a and 65b can be screwed into and out of the connecting female screw threads 60a and 60b on the inner sheath housings S3a and 53b.

The outer diameters of the tubes 63a and 63b, and inner sheath pipes 64a and 64b are smaller than the internal channels of the needle lumens 11a and 11b, connecting pipes 33a and 33b, connecting ports 3Sa and 3Sb, distal plugs 40a and 40b, connecting sheaths 39a and 39b, and slider receivers 46a and 46b. The outer diameters of the connecting male screws 65a and 65b are smaller than the internal channels of the slider receivers 46a and 46b. The inner diameters of the tubes 63a and 63b, inner sheath pipes 64a and 64b, and connecting male screws 65a and 65b are of a size that will allow the needles 5 and 6 to smoothly pass through them. The tubes 63a and 63b are desirably formed with an inner diameter of approximately 0.5 to 2 mm and an outer diameter of approximately 1 to 2.5 mm.

The length of the tubes 63a and 63b are fixed so that the distal ends of the tubes 63a and 63b are positioned toward the proximal ends from the distal openings of the needle lumens 11a and 11b when the inner sheath sliders 42a and 42b are completely retracted from the slider receivers 46a and 46b, and the distal ends of the tubes 63a and 63b come approximately 3 to 15 mm toward the distal end from the proximal end of the side opening 13 when the inner sheath sliders 42a ant 42b are completely projected until they hit the slider receivers 46a and 46b. The inner sheaths 4a and 4b and the inner sheath sliders 42a and 42b are preferable and may be omitted from the tissue puncturing system 1.

As shown in FIGS. 4 and 20, the needle 5 comprises a needle body 66 and needle grip 67. The needle 5 may be inserted into the inner sheath 4 via a needle connecting port 61 on either of the needle sliders 43a and 43b. The needle grip 67 is-connected to the proximal end of the needle body 66, and the needle body 66 and needle grip 67 both have internal channels. The needle body 66 is formed from a flexible metal pipe such as stainless steel or nitinol, which may withstand the pressure from the proximal end during puncturing and follow the curvature of the connecting sheath 39 and needle lumen 11. The distal end of the needle body 66 is pointed to enable it to puncture tissue in body cavities. The needle body 66 is formed with an inner diameter of approximately 0.5 to 1.5 mm and outer diameter of approximately 0.7 to 2 mm.

To allow the needle body 66 to protrude from the distal end of the inner sheath 4, the outer diameter of the needle body 66 is desirably close enough to the inner diameter of the inner sheath 4 to enable it to slide within the inner sheath 4. The periphery of the distal end of the needle grip 67 is luer-tapered so that it will fit into the luer-taper on the internal channel of the needle connecting port 61. The needle grip 67 is formed from a metal such as stainless steel or aluminum, or a elastic material such as polypropylene, ABS, polycarbonate, polyacetal, or polysulfone. The length of the needle 5 is set so that the distal end of the needle body 6 is positioned toward the proximal. end from the distal end of the tube 63b when the needle slider 43b with the needle 5 is completely retracted from the inner sheath slider 42b. In addition, the length of the needle 5 is also set so that the distal end of the needle body 66 comes approximately 5 to 25 mm toward the distal end from the distal end of the side opening 13 when the inner sheath slider 42 is completely retracted from the slider receiver 46b, and the needle slider 43b protrudes and comes exactly up against the inner sheath slider 42b.

A suture 68 is preset to feed into the needle 5. The distal end of the suture 68 is positioned behind the distal end of the needle body 66. The proximal end of the suture 68 is exposed toward the proximal side from the needle grip 67, and the exposed length is set to be approximately 50 cm longer than the total length of the needle 5. A cap 155 is provided in the vicinity of the proximal end of the grip 67. The cap 155 can be attached to the proximal opening of the grip 67 to seal the opening. The cap 155S is formed from rubber such as silicone rubber or fluoro-rubber or a plastic such as polypropylene, polyethylene, polystyrene, or a thermoplastic elastomer. With the suture 68 set in the needle 5, the cap 155 covers the proximal opening of the grip 67. In this construction, the suture 68 is held between the cap 155 and the proximal end of the grip 67 and is held detachably in the needle. Air-tightness is also maintained at the proximal opening of the grip 67.

A knot 69 is formed in the vicinity of the distal end of the suture 68. The suture 68 may be of any type generally used for surgery and may be made of nylon or silk. The suture 68 has a diameter of approximately 0.2 to 0.5 mm and desirably approximately 0.25 to 0.35 mm. The outer diameter of the knot 69 is preferably the largest size that may pass through the needle 5. The suture 68 is preferably of a color such as blue or green that is easy to identify in endoscopic images of body cavities. A larger diameter member 41 (which is not shown in FIG. 16) made of metal or plastic and in the shape of a ball may be fixed at the distal end of the suture 68 instead of the knot 69 in the vicinity of the distal end of the suture 68. The larger diameter member 41 may be of other shapes as long as it has an outer diameter that enables it to be inserted through the needle body 66. As shown in FIG. 5, the needle 6 comprises a needle body 70, needle grip distal part 51, needle grip proximal part 72, O-ring 73, and suture forceps 74.

The needle 6 may be inserted into the inner sheath 4 via a needle connecting port 61 which has no needle 5 inserted through it. The needle body 70 and needle grip distal part 71 have the same construction as the needle body 66 and the needle grip 67 of the needle 5. The needle grip distal part 71, the needle grip proximal part 72, and O-ring 73 have the same construction as the housing 47, ring 48, and O-ring 50 of the slider receiver 46, and the O-ring 73 is held between the needle grip distal part 71 and the needle grip proximal part 72. The suture forceps 74 are slid into the needle body 70, needle grip distal part 71, and needle grip proximal part 72 beforehand. A loop-shaped grasper 75 such as snare forceps is formed at the distal end of the suture forceps 74. The grasper 75 is formed from metal wire such as stainless steel or nitinol or various plastic wires. The wire may be stranded or a single wire. The wire diameter may be of any size as long as the grasper 75 may be inserted through the needle body 70. The grasper 75 when protruding from the needle body 50, opens to form a loop opening 98. The loop opening 98 has a diameter of approximately 10 to 20 mm. An operation member 76 extends from the proximal end of the grasper 75 to the proximal end of the needle grip proximal part 72, and an operation knob 77 is connected to the proximal end. The outer diameter of the operation member 76 is slightly larger than the inner diameter of the O-ring 73 to maintain air-tightness between them. The operation member 76 is formed from a thin metal pipe or wire such as stainless steel or nitinol, which has superior rotational trackability and flexibility. It is preferable that the grasper 75 be rotatable by rotating the operation knob 77.

The needle bodies 66 and 70 of the needles 5 and 6 may be constructed with a hollow flexible sheath made of a plastic tube such as fluorocarbon resin, polyethylene, polyamide, polyimide, polyurethane, or various thermo plastic elastomer or metal coils and a needle made of stainless steel, nitinol or the equivalent attached to the distal end of the hollow sheath. Plastic tubes containing metal mesh may be used for the hollow sheath to prevent kinking. Returning to the explanation of FIG. 2, a reinforcing member 78 is fixed in front of or behind the side opening 13 on the treatment lumen 12 of the sheath section 7. As shown in FIGS. 7-10, the reinforcing member 78 comprises a distal annular part 79, proximal annular part 80, and three beams 81a, 81b, and 81c connecting the annular parts 79 and 80. The reinforcing member 78 is formed from various metals such as stainless steel, aluminum, or brass, or various plastic materials such as ABS, polypropylene, polycarbonate, acrylic, polyacetal, polysulfone, polyimide, polyamide-imide, or materials with relatively high rigidity such as FRP or ceramics. Desirably it should be made of a transparent material such a polycarbonate, norbornene resin, or cycloolefin resin so as not to obstruct the field of view of the endoscope 9 and to enable observation of the outside of the sheath section 7.

The distal annular part 79 and the proximal annular part 80 are positioned axially, and the distance between them is equal to or more than the longitudinal length of the side opening 13. The outer diameters of the distal annular part 79 and the proximal annular part 80 are roughly equal to the inner diameter of the treatment lumen 12 and fixed to the treatment lumen 12 by adhesives or welding. The beams 81a, 81b, and 81c extend longitudinally from the proximal end of the distal annular part 79 to the distal end of the proximal annular part 80 along the sheath section 7. The distance between the beams 81a and 81c is made larger than the width of the side opening 13 so that they are not exposed in the side opening 13. The thickness of the distal annular part 79, the proximal annular part 80, and the beams 81a, 81b, and 81c is approximately 0.1 to 1 mm. The distal annular part 79, the proximal annular part 80, and the beams 81a, 81b, and 81c may be separately formed. The number of beams 81 is not limited to three and may be at least one as long as the beam 81 has sufficient bending strength to prevent the sheath section 7 from kinking. Desirably, the distal annular part 79 and proximal annular part 80 of the reinforcing member 78 is C-ring shape to prevent the needle tip from becoming hooked by the distal annular part 79 and proximal annular part 80 when the needles 5 and 6 protrude from the needle lumens 11a and 11b (FIG. 95).

Needle guides 82 and 83 are fixed to the distal annular part 79 of the reinforcing member 78. As shown in FIG. 13, the needle guide 82 is also an annular member having a guide channel 84a with both its ends open, and has a proximal guide part 85a at its proximal side. The needle guide 83 is also an annular member having an guide channel 84b with both its ends open, and has a proximal guide part 85b at its proximal side and a bending part 86 at its distal end. The bending part 86 is angled at approximately 90 degrees to the proximal guide part 85b. The needle guide 82, unlike the needle guide 83, has no bending part 86 and has the distal end port opening aligned coaxially with the proximal guide part 85a. A number of support walls 87 are provided in the distal annular part 79, and the proximal guide parts 85a and 85b are fixed to the distal annular part 79, being held between the support walls 87.

In this construction, the needle guide 83 is fixed to the distal annular part 79 with the bending part 86 facing the center of the sheath section 7 and the other needle guide 82. The needle guides 82 and 83 are fixed to the distal annular part 79 so that the proximal ends of the proximal guide parts 85a and 85b are situated proximal to the distal end of the side opening 13. The distance between the distal end of the side opening 13 and the proximal guide parts 85a and 85b is made equal. The needle guides 82 and 83 are coaxial with the center axes of the needles 5 and 6 inserted through the needle lumens 11a and 11b. The needle guides 82 and 83 are attached so that the distal ends of the needle bodies 66 and 70 enter the proximal openings of the proximal guide parts 85a and 85b when the needle sliders 43a and 43b protrude against the inner sheath sliders 42a and 42b.

The cross-sectional shape of the proximal guide parts 85a and 85b is preferably circular or ellipsoidal as shown in FIG. 9 but is not limited to these shapes. The guide channels 84a and 84b comprise conical tapered parts 88a and 88b, needle channels 89a and 89b, needle abutment surfaces 90a and 90b, and suture channels 91a and 91b. Tapered parts 88a and 88b are formed proximal to the proximal guide parts 85a and 85b, and the taper angle a is approximately 10 to 90 degrees. The needle channels 89a and 89b are provided distal to the tapered parts 88a and 88b and have inner diameters slightly larger than the needle bodies 66 and 70 so that the needle bodies fit the inner diameters. The length of the needle channels 89a and 89b is up to 10 mm.

The suture channels 91a and 9b are provided distal to the needle channels 89a and 89b and extend to the distal ends of the needle guides 82 and 83. The cross-sectional shape of the suture channel 91a of the needle guide 82 is a shortened cylinder as shown in FIG. 14. Both the shorter and longer diameters of the suture channel 91a are smaller than the inner diameter of the needle channel 89a. The needle guide 82 is fixed on the distal annular part 79 so that the longer diameter of the suture channel 91a extends perpendicular to the side opening 13. The inner diameter of the suture channel 91b of the needle guide 83 is smaller than that of the needle channel 89b and the same as that of the needle body 66. The steps between the needle channels 89a and 89b and the suture channels 91a and 92b serve as the needle abutment surfaces 90a and 90b. The distance between the distal end of the side opening 13 and the needle abutment surfaces 90a and 90b is set shorter than the distance between the distal end of the side opening 13 with the needle bodies 66 and 70 completely protruding and the distal ends of the needle bodies 66 and 70.

Guide slits 92a and 92b extend along the needle guides 82 and 83 respectively along their entire length. The guide slits 92a and 92b are provided on the inner sides (on the center axis side of the-sheath section 7) of the needle guides 82 and 83 fixed on the distal annular part 79 so that the guide slits face each other. The plane of the guide slit 92a is orthogonal to the plane of the longer diameter of the suture channel 91a (FIG. 9). The width of the guide slits 92a and 92b is set smaller than the thickness of the suture 68. The longitudinal length of the needle guide 83 is longer than the length of the needle guide 82 so that the distal opening of the guide channel 84b is situated approximately 5 to 10 mm distal to the distal opening of the guide channel 84a. The needle guides 82 and 83 are formed from metals such as stainless, aluminum, or brass, or relatively rigid plastic materials such a polyacetal or polysulfone.

The endoscope 9 inserted through the overtube 2 has a suction channel, whose proximal end is connected to a suction source (not shown). The endoscope 9 is preferably a flexible endoscope however a rigid endoscope may be used. The entire tissue puncturing system 1 is constructed to maintain air-tightness to the outside except the distal opening of the sheath section 7 and the side opening 13.

Those skilled in the art will appreciate that variations of the tissue puncturing system described above are possible. The loop of the grasper 75 of the needle 6 may assume any shape, and may be shaped as basket forceps as shown in FIG. 16. In this case, the cross-sectional shape of the suture channel 91a is not necessarily a shortened cylinder and may be circular with its inner diameter smaller than that of the needle channel 89a as in the suture channel 91b as shown in FIG. 16. As shown in FIG. 17 (a), a bullet-shaped distal tip 94 with cross slits 93 may be attached to the distal end of the sheath section 7. The distal tip 94 is formed from various rubbers such as silicone rubber or relatively soft plastic material such as various thermo plastic elastomers, polyurethane, vinyl chloride, polyethylene, polyamide, or polytetrafluoroethylene. Four flaps 95 are provided in slit 93 on the distal tip 94. When no endoscope 9 is inserted though the slit 93, the flaps 95 close as shown in FIG. 17(a) to allow the distal tip 94 to maintain a bullet shape and to maintain air-tightness between the sheath section 7 and the outside.

As the endoscope 9 advances thorough the slit 93, the flaps 95 open as shown in FIG. 17(b) to allow passage of the endoscope 9. The slits 93 are not limited to having a cross shape, and the number of the slits and flaps 95 are not limited to four as shown in FIGS. 17a and 17b. As shown in FIG. 19, the sheath distal unit 96 including the treatment lumen 12 and side opening 13 of the sheath section 7 may be separate from the sheath section 7 and may be connected to the distal end of the sheath section 7 and detachable from it. In this construction, the endoscope lumen 10 and needle lumens 11a and 11b extend to the vicinity of the distal end of the sheath section 7.

An assembly of the tissue puncturing system will now be described with reference to FIGS. 1, 18, and 20. The distal plugs 40a and 40b on the connecting sheaths 39a and 39b are inserted into the connecting ports 35a and 35b, the fixing screws 38a and 38b are tightened, and the overtube 2 is connected to the operation unit 3. The connecting male screws 65a and 65b on the inner sheaths 4a and 4b are screwed into the connecting female screw threads 60a and 60b on the inner sheath housings 53a and 53b to connect the inner sheaths 4a and 4b with the inner sheath sliders 42a and 42b. With the fixing screws 57a and 57b loosened, the inner sheath housings 53a and 53b are inserted into the housings 47a and 47b of the slider receivers 46a and 46b, and the rings 48a and 48b are tightened to the housings 47a and 47b to secure them. With the inner sheath sliders 42a and 42b completely retracted from the slider receivers 46a and 46b, the fixing screws 57a and 57b are tightened to secure them. The needles 5 and 6 are inserted from the proximal openings of the needle connecting ports 61a and 61b on the needle sliders 43a and 43b.

The luer tapers on the needle grip 67 and needle grip distal part 71 are inserted into the inner luer tapers on the needle connecting ports 61a and 61b to fix the needles 5 and 6 into the needle sliders 43a and 43b. The needle sliders 43a and 43b are completely retracted from the inner sheath sliders 42a and 42b. The operation knob 77 of the needle 6 is pulled fully out from the needle grip proximal part 72. At this stage, the grasper 75 is withdrawn into the needle body 70. The endoscope 9 is inserted via the endoscope insertion port 22 of the overtube 2 into the endoscope lumen 10 and treatment lumen 12. The endoscope 9 is further advanced until it protrudes from the distal end of the overtube 2.

The suction and puncturing of the sutured tissue will now be described with reference to FIGS. 21 through 23. The overtube 2 is inserted into the patient's body with the endoscope 9 inserted through it while observing the endoscopic image of the overtube 2 until it reaches the vicinity of the sutured tissues 97a and 97b. Since the side opening 13 is reinforced with the reinforcing member 78, the sheath section 7 is reliably prevented from kinking at the side opening 13. The distal end of the endoscope 9 is retracted to the proximal side of the side opening 13, and the overtube 2 is moved back and forth or rotated under endoscopic observation until the side opening 13 is situated above the sutured tissues 97a and 97b (FIG. 21). At this stage, the suction provided on the endoscope 9 is turned on to suck up the sutured tissues 97a and 97b via the side opening 13 into the treatment lumen 12. Since the reinforcing member 78 is provided, the sheath section 7 is reliably prevented from collapsing at the side opening 13 under the suction. The sutured tissue 97a is checked to confirm that the puncture site is situated on the extension of the needles 5 and 6. If the puncture side is dislocated, turn off the suction, the side opening 13 is repositioned, and the sutured tissues 97a and 97b are sucked up again. In repositioning, the overtube 2 may be replaced with a second overtube 2 with a side opening 13 of different size.

To facilitate confirmation of the puncture site on the sucked tissue 97a, the site may be marked with the endoscope 9, a standard endoscope needle, and ink before inserting the overtube 2. The fixing screws 57a and 57b of the inner sheath sliders 42a and 42b of the operation unit 3 are loosened to advance the inner sheath sliders 42a and 42b toward the distal ends against the slider receivers 46a and 46b. Since the operation unit 3 is positioned away from the endoscope insertion section 8 owing to the connecting sheaths 39a and 39b, the operator may operate the endoscope 9 at a distance from the assistant operating the operation unit 3, thus preventing interference between the two. When the inner sheath sliders 42a and 42b are advanced, the distal ends of the tubes 63a and 63b are pressed against the sutured tissues 97a. Then the needle sliders 43a and 43b are advanced toward the distal ends of the inner sheath sliders 42a and 42b until the needle connecting ports 61a and 61b butt up against the inner sheath rings 54a and 54b and the needle bodies 66 and 70 protrude from the distal ends of the tubes 63a and 63b. The needle bodies 66 and 70 protrude almost in parallel. Protrusion of the needle sliders 43a and 43b may be performed simultaneously or individually. The needle bodies 66 and 70 then penetrate the sutured tissues 97a and 97b (FIG. 22).

The needle bodies 66 and 70 are further advanced, and the distal ends of the needle bodies 66 and 70 are inserted into the guide channels 84a and 84b of the needle guides 82 and 83 and butt up against the needle abutment surfaces 90a and 90b on the needle channels 89a and 89b (FIG. 23). Even when the distal ends of the needle bodies 66 and 70 are dislocated from the center axes of the guide channels 84a and 84b as the needle bodies 66 and 70 penetrate the sutured tissues 97a and 97b, the distal ends of the needle bodies 66 and 70 may be smoothly guided by the tapered parts 88a and 88b into the needle channels 89a and 89b. The suction of the sutured tissues 97a and 97b for the endoscope 9 is then turned off.

Figure 24:
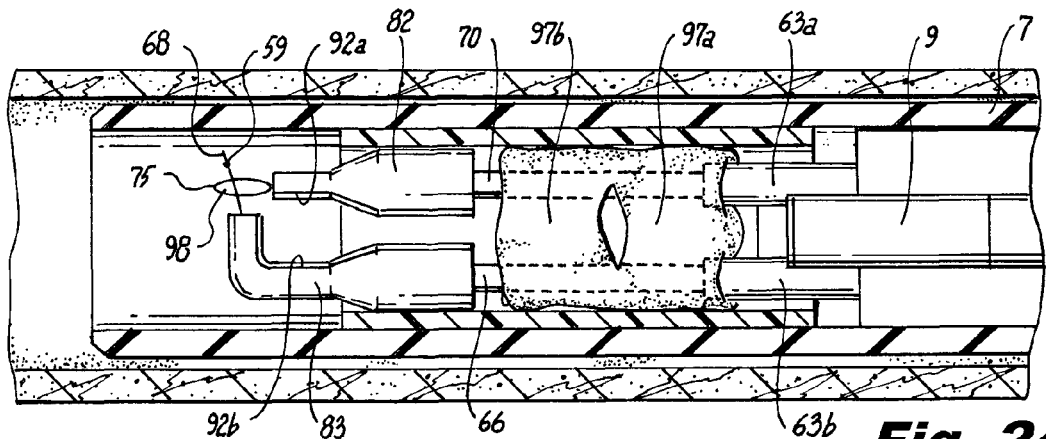
FIGS. 24 to 27 are operational views illustrating the suture being fed between two needles.
Figure 25:
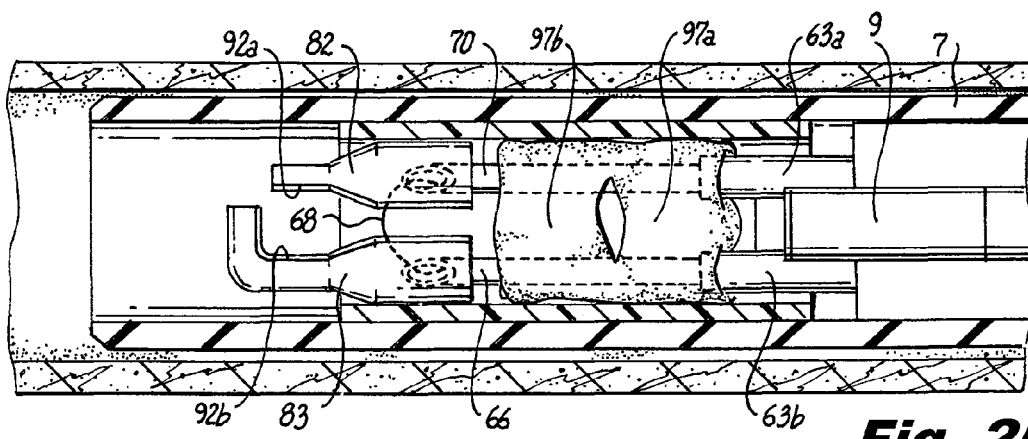

The insertion of the suture into tissue will now be described with reference to FIGS. 14, and 24 through 27. The operation knob 77 of the needle 6 is pressed toward the distal end until the grasper 75 of the suture forceps 74 protrudes from the distal end of the needle body 70. The grasper 75 passes through the suture channel 91a and protrudes from the distal end of the needle guide 82. Since the grasper 75 opens in the direction of the longer diameter of the suture channel 91*a* as shown in FIG. 14, the loop opening 90 of the grasper 75 is positioned in a plane substantially perpendicular to the center axis of the bending part 86 of the needle guide 83. The cap 155 is removed from the needle grip 67 of the needle 5 and the suture 68 exposed from the grip 67 via the suture channel 91*b* is advanced until the distal end of the suture 68 protrudes from the distal end of the bending part 86 of the needle guide 83. When the suture 68 is further advanced, the distal end of the suture 68 is inserted through the loop opening 98. Under endoscopic observation, the suture 68 is advanced until the knot 69 in the suture 68 passes through the loop opening 98 (FIG. 24). The suture 68 extending from the proximal end of the needle grip 67 is then released and the operation knob 77 is pulled back to the proximal side. The grasper 75 is withdrawn into the needle body 70 to grasp the distal end of the suture 68. At this stage, the knot 69 serves as a stopper to prevent the suture 68 from being readily released from the grasper 75.

The needle sliders 43*a* and 43*b* are then pulled back toward the proximal side. The needle sliders 43*a* and 43*b* may be pulled back simultaneously (FIG. 25) or individually (not shown). A part of the suture 68 that has passed between the needle bodies 66 and 70 passes through the guide slits 92*a* and 92*b* in the corresponding needle guides 82 and 83. and is removed from the needle guides 82 and 83. Said part of the suture 68 extends between exiting points 113*a* and 113*b* penetrated by the needle bodies 66 and 70 and comes into contact with the sutured tissue 97*b* (FIG. 26). The needle sliders 43*a* and 43*b* are then completely retracted from the inner sheath sliders 42*a* and 42*b* to withdraw the distal ends of the needle bodies 66 and 70 into the tubes 63*a* and 63*b*. The fixing screws 57*a* and 57*b* on the inner sheath sliders 42*a* and 42*b* to completely retract the inner sheath sliders 42*a* and 42*b* are loosened to the proximal end of the slider receivers 46*a* and 46*b*. This retracts the distal ends of the tubes 63*a* and 63*b* via the distal openings of the needle lumens 11*a* and 11*b* to the proximal side (FIG. 27). The suture 68 extending from the proximal end of the needle grip 67 is released and the overtube 2 and endoscope 9 are removed from the patient's body. At this stage, the suture 68 passes through the sutured tissues 97*a* and 97*b* from the entering point 112*b* to the exiting point 113*b*, to the exiting point 113*a*, and to entering point 112*a*. The operation knob 77 is pushed toward the distal end against the needle grip proximal unit 72 again until the grasper 75 protrudes and the suture 68 is removed from the grasper 75 (not shown).

The tying off of the suture will now be described with reference to FIGS. 28 and 29. Both ends of the suture 68 coming out of the patient's body are tied to form a knot 99. The knot 99 may be of any type commonly used in surgery. The knot 99 is advanced into the patient's body using an ordinary knot pusher inserted in the forceps channel of the endoscope 9 while observing the knot 99 with the endoscope 9 (FIG. 28). When the knot 99 reaches the vicinity of the sutured tissue 97*a*, the knot pusher is pressed against the sutured tissue 97*a* and both ends of the suture 68 are simultaneously pulled to fix the knot 99 (FIG. 29).

This step is repeated once or several times and the knot 99 is checked to determined if it is securely formed. Then the endoscope 9 and knot pusher are removed out of the patient's body. To complete the procedure, the endoscopic scissors forceps, not shown in the figure, are used to cut the suture 68 in the vicinity proximal to the knot 99, and the cut suture 68 is removed out of the body. The sutured tissues 97*a* and 97*b* may be completely sutured by repeating the above procedure according to the length and range required. For patients with gastroesophageal reflux disease, the overtube 2 is inserted into the esophagus as shown in FIGS. 96 through 98, the port 13 is positioned on the esophageal wall 216 immediately above the cardiac part of the stomach 215, and the above procedure is performed to enable suturing of the esophageal wall 216 with the stomach wall 217 and formation of an artificial valve 218.

In the present first embodiment, the overtube 2 is provided with an endoscope lumen 10 for accepting the endoscope 9 and allows the endoscope 9 to be inserted into the treatment lumen 12, into which the sutured tissues 97*a* and 97*b* are sucked. In this construction, the sutured tissues 97*a* and 97*b* are sucked in the treatment lumen 12 located at a position substantially coaxial with and in front of the endoscope 9. Therefore, the needles 5 and 6 may satisfactorily puncture the target puncture site on the sutured tissue 97*a* or a satisfactory puncture may be readily and reliably confirmed before the actual puncture is made by the needles 5 and 6. In addition, the distal end of the endoscope 9 may be moved back and forth against the side opening 13 or curved for adjustment to obtain the optimum state for observation of the sutured tissues 97*a* and 97*b*. Thus, the puncture site may be minutely controlled to achieve reliable suturing. The treatment itself is simplified, and the treatment time is significantly shortened. Since the needles 5 and 6 are positioned in parallel and at constant intervals by the parallel and uniformly-spaced needle lumens 11*a* and 11*b*, the entering points 112*a* and 112*b*, and the exiting points 113*a* and 113*b* have a uniform interval as is required. Thus a uniform stitch interval is ensured and may be reliably controlled, thus simplifying the treatment procedure and drastically reducing the treatment time. Even when multiple stitches are required, the distance between single stitches may be uniformly controlled so as to achieve reliable suturing with the least number of stitches.

Since the endoscope 9 lies substantially coaxial with the treatment lumen 12, a large space may be used to suck in the sutured tissues 97*a* and 97*b* without increasing the outer diameter of the overtube, thus easing any pain in the patient during insertion of the overtube 2. Since the endoscope 9 can slide in the overtube 2, the endoscope and overtube 2 may be inserted into the body cavity of the patient with the bending section of the endoscope 9 protruding from the distal opening of the overtube 2, thus improving the insertability of the endoscope 9 and overtube 2, and easing any pain on the patient during insertion.

Since two needles 5 and 6 are pre-positioned, those two needles 5 and 6 may puncture the tissues immediately after the sutured tissues 97*a* and 97*b* are sucked in via the side opening 13, thus simplifying the treatment procedure and drastically reducing the treatment time. Since the needles 5 and 6 puncture after the inner sheaths 4*a* and 4*b* butt up against the target puncture site, the target puncture site may be readily confirmed and the correct positioning readily achieved, thus achieving reliable suturing, simplifying the treatment procedure and drastically reducing the treatment time. Since at least a part of sheath section 7 in the vicinity of the side opening 13 is transparent, the outside of the sheath 7 maybe observed with the endoscope 9, making it easy to position the side opening 13, thus improving operability and reducing the treatment time. When the-distal end of the sheath section 7 is independent of the sheath distal unit 96, the components other than the sheath distal unit 96 may be used in common when overtubes 2 are manufactured with side openings 13 of different sizes, thus reducing manufacturing costs. The tissue puncturing system 1 is constructed to maintain air-tightness with the outside except for the distal opening and the side opening 13 of the sheath section 7, allowing efficient suction of the sutured tissues 97a and 97b via the side opening 13.

Figure 30:
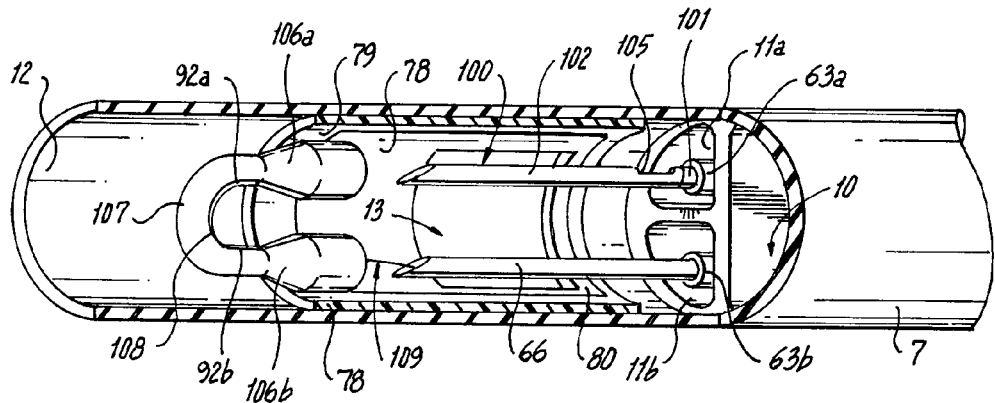
FIG. 30 is a partial cross-sectional view of an overtube according to .a second embodiment.
Figure 31A:
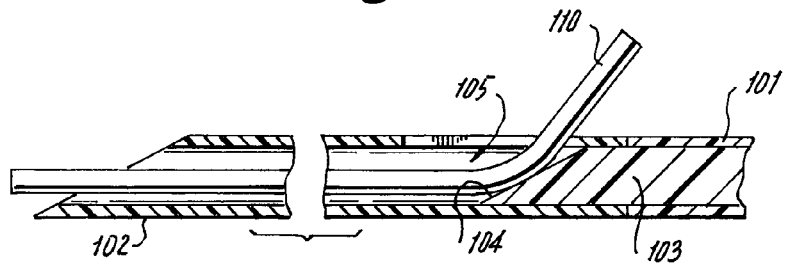
FIG. 31(a) is a vertical cross-sectional view of the front end of the needle Of FIG. 30 at the side for receiving the suture.
Figure 31B:
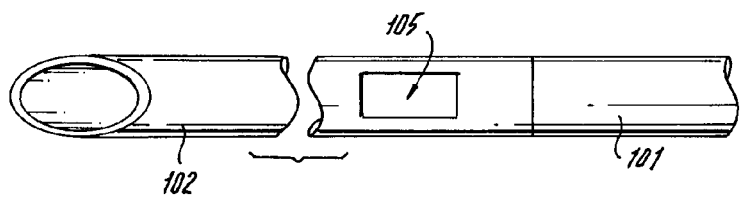
FIG. 31(b) is a front view as seen from the side hole of the needle of FIG. 31(a).
Figure 32:
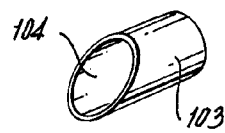
FIG. 32 is an external overview showing the guide member within the needle of FIG. 31(a).
Figure 33:
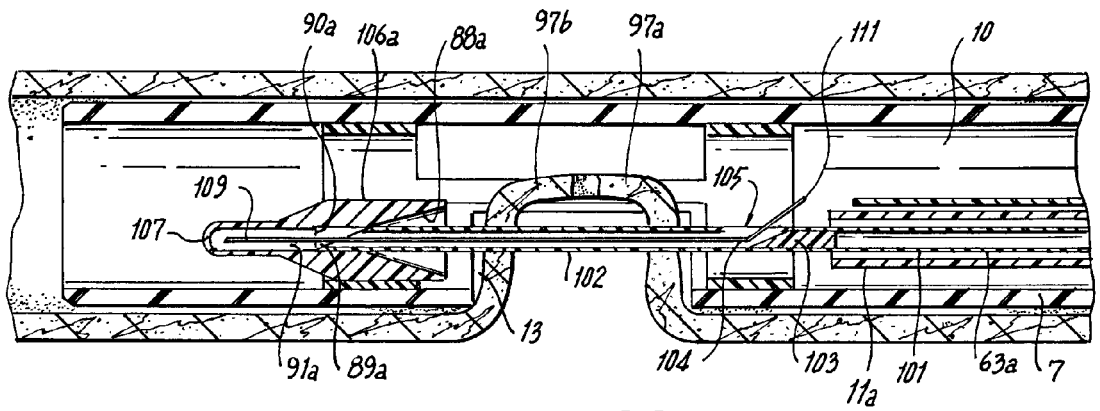
FIGS. 33 and 34 are operational views illustrating receiving the suture by one needle.
Figure 34:
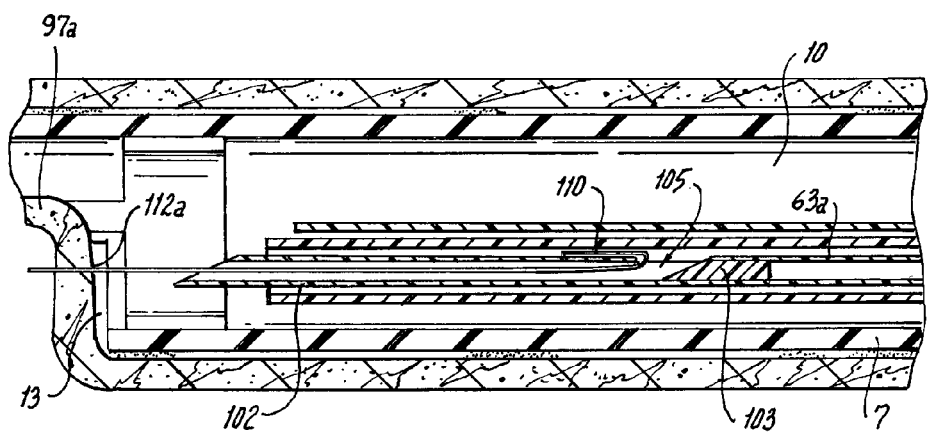
Figure 35:
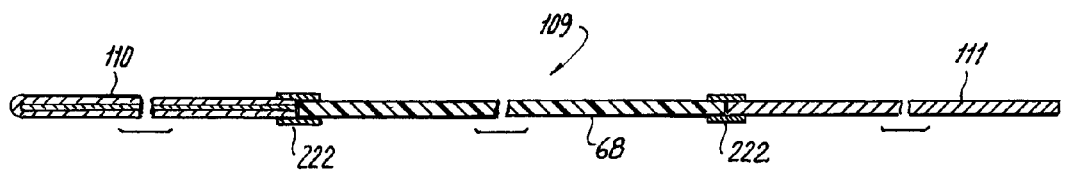
FIG. 35 is a cross-sectional view of the suturing wire of FIG. 33.
Figure 36:
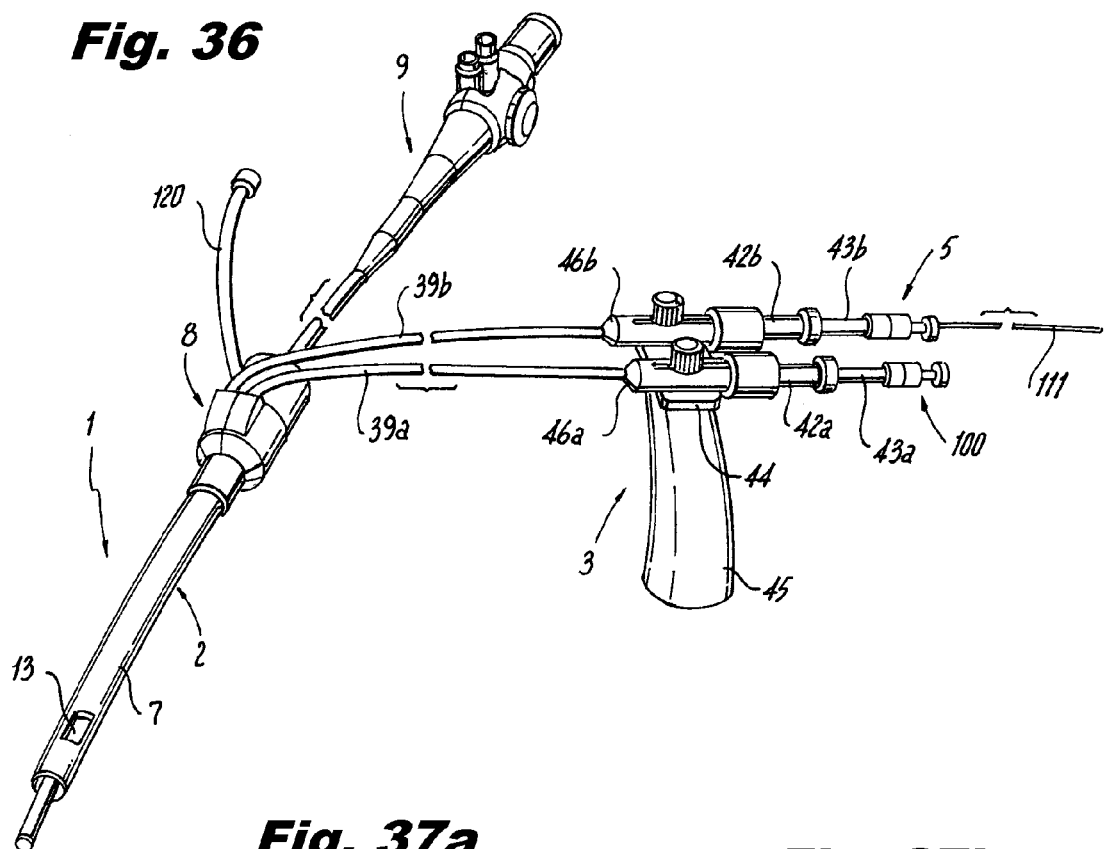
FIG. 36 is an external overview of the tissue puncturing system according to the second embodiment.

A second embodiment of the tissue puncturing system will now be described with reference to FIGS. 30 through 36. FIG. 30 is a partial cross-sectional view of the overtube. FIG. 31 (a) is a vertical cross-sectional view of the front end of the needle at the side for receiving the suture. FIG. 31 (b) is a front view as seen from the side hole of FIG. 31 (a). FIG. 32 is an external overview for showing only the guide member within the needle. FIGS. 33 and 34 are operational views for showing a state of receiving the suture by one needle. FIG. 35 is a cross-sectional view of the suturing wire. FIG. 36 is an external overview of the entire tissue puncturing system. Descriptions will be given only where different from the first embodiment. One of the two needles has the same construction as the needle 5. A suturing wire 109 is pre-inserted in the needle 5. As shown in FIG. 35, the suturing wire 109 comprises a guide wire 110, suture 68, push wire 111, and connecting pipe 222. The guide wire 110 and push wire 111 are connected to the distal and proximal ends of the suture 68 respectively. Such connection to the connecting pipe 222 is made by adhesive or caulking. The suturing wire 109 is set in the needle 5 so that its distal end is positioned proximal to the distal end of the needle body 66. The guide wire 110 comprises a metal core such as a stainless steel wire with less flexibility than the suture 68 with a coating over the metal core of a plastic resin that has a relatively high slidability such as fluorocarbon resin, or with silicone. Preferably, the core diameter is approximately 0.2 mm and the coating thickness is approximately 0.05 mm. The length of the guide wire is approximately 10 cm. The push wire 111 is formed from metal wire such as stainless steel wire with less flexibility than the suture 68, and the outer diameter is preferably the largest size that will allow it to be inserted through the needle 5. The push wire 111 has a length approximately 50 cm longer than the length of the needle 5, and its distal end is positioned in the needle grip 67.

As shown in FIG. 31, the other needle 100 comprises a needle grip 67 (FIG. 3), needle sheath 101, needle distal end 102, and guide member 103. The needle sheath 101 is connected to the distal end of the needle grip 67, and both the needle sheath 101 and needle grip 67 have an internal channel. The guide member 103 is fixed to the distal end of the needle sheath 101. The guide member 103 is a solid cylindrical member having a tapered surface 104 at its distal end as shown in FIG. 32. The guide member 103 has an outer diameter slightly smaller than the inner diameter of the needle sheath 101. The guide member 103 is attached to the internal channel of the needle sheath 101 at the position where the tapered surface 104 on the guide member 103 is exposed toward the distal end of the needle sheath 101. The needle distal end 102 is fixed around the periphery of the guide member 103 so that its proximal end butts up against the distal end of the needle sheath 101. The needle distal end 102 has an internal channel, whose inner diameter is slightly larger than the outer diameter of the guide member 103 and is approximately 0.5 to 1.5 mm.

The needle sheath 101 and needle distal end 102 have the same outer diameter and have a size that gives a clearance with the inner diameter of the tube 63a of the inner sheath 4a that is slightly smaller than the outer diameter of the guide wire 110. The needle sheath 101 and needle distal end 102 are formed from metal pipes made of stainless steel or nitinol which will withstand the pressure from the proximal end during puncturing and have the flexibility to follow the curvature of the connecting sheath 39 and needle lumen 11. The needle distal end 102 has a pointed tip to penetrate tissue in body cavities. A side hole 105 is provided on the side of the needle distal end 102 above the tapered surface 104. The side hole 105 may be rectangular, for example, as shown in FIG. 31 (b) and has a size that allows easy passage of the guide wire 110. The proximal end of the side hole 105 is tapered and flush with the tapered surface 104. The distance between the distal end of the needle distal end 102 and the distal end of the side hole 105 is set as shown in FIG. 33 so that the needle distal end 102 is positioned proximal to the side opening 13 and distal to the distal opening of the needle lumen 11 a when the needle 100 butts up against the needle abutment surface 90a. Needle guides 106a and 106b are provided on the distal annular part 79 of the reinforcing member 78.

The needle guides 106a and 106b substantially have the same construction as the needle guide 83 of the first embodiment except for the bending part 86. The needle guides 106a and 106b have the distal ends connected via the guide tube 107 with an internal channel. The inner diameter of the guide tube 107 is roughly the same as that of the suture channels 91a and 91b on the needle guides 106a and 106b. A guide slit 108 is provided on the side of the proximal end of the guide tube 107 and connected to the guide slits 92a and 92b on the needle guides 106a and 106b to form a single slit. The width of the guide slit 108 is equal to or smaller than the width of the guide slits 92a and 92b and smaller than the outer diameter of the suturing wire 109. The guide tube 107 is formed from a plastic material such as fluorocarbon resin, polyethylene, polyamide, polyimide, polyurethane, or a thermo plastic elastomer. The guide tube 107 may comprises an extruded tube, into which the guide slit 108 is machined after extrusion, or formed with the guide slit 108 by injection molding. A suction tube 120 having an internal channel connected to the endoscope lumen 10 is provide in the endoscope insertion section 8 of the overtube 2 and has a proximal end that can be connected to and detached from a suction source (not shown).

An operation of the second embodiment of the tissue puncturing system will now be described. Only the operation different from the first embodiment will be described. The sutured tissues 97a and 97b are sucked via the side opening 13 by connecting the suction tube 120 to the suction source (not shown) instead of using the suction function of the endoscope 9. As shown in FIG. 33, after the needles 5 and 100 puncture the sutured tissues 97a and 97b, the inner sheath sliders 42a and 42b are completely removed from the slider receivers 46a and 46b, and the distal ends of the inner sheaths 4a and 4b are retracted to the vicinity of the distal opening of the needle lumens 11a and 11b. The push wire 111 of the suturing wire 109 exposed from the needle grip 67 of the needle 5 is then held and advanced. The guide wire 109 protruding from the distal end of the needle 5 then passes through the suture channel 91b in the needle guide 106b, guide tube 107, and suture channel 91a in the needle guide 106a and enters the needle distal end 102 of the needle 100.

As shown in FIG. 34, the guide wire 109 then proceeds along the tapered surface 104 of the guide member 103, passes through the side hole 105, and protrudes from the needle 100. After confirming on the images from the endoscope 9 that the distal end of the guide wire 109 protrudes out of the needle 100, the needles sliders 43a and 43b are completely retracted from the inner sheath sliders 42a and 42b. The needles 5 and 100 are then removed from the sutured tissues 97a and 97b, and the needles 5 and 100 are withdrawn into the tubes 63a and 63b respectively. At this stage, a part of the suturing wire 109 passed between the needles 5 and 100, passes through the guide slit 108 in the guide tube 107 and the guide slits 92a and 92b in the corresponding needle guides 106a and 106b and is removed from the needle guides 106a and 106b.

As shown in FIG. 27 of the first embodiment, said part of the suturing wire 109 extends between exiting points 113a and 113b penetrated by needles 5 and 100 and comes into contact with the sutured tissue 97b. When the needles 5 and 100 are withdrawn into the tubes 63a and 63b, the guide wire 110 protruding from the needle 100 is positioned and held in the clearance between the outer surface of the needle distal end 102 and the inner surface of the tube 63a, since the clearance is smaller than the outer diameter of the guide wire 110. The suturing wire 109 extending from the proximal end of the needle grip 67 is released, and the overtube 2 and endoscope 9 are removed from the patient's body. The needle slider 43a is pushed toward the distal end until the needle distal end 102 protrudes from the distal end of the tube 63a, and the guide wire 110 is removed from the needle distal end 102. The push wire 111 extending out of the patient's body is returned so that the suture 68 penetrates the sutured tissues 97a and 97b. Both ends of the suture 68 are cut where they extend outside the patient's body and the guide wire 110 and push wire 111 are separated.

In addition to the effects of the first embodiment, the effects described below are obtained. Since the suturing wire 109 is held by the needle 100 and the inner sheath 4a, operation of the suture forceps 74 as in the first embodiment is not required, thus improving operability and shortening the treatment time. Since the guide wire 109 coated with a highly slidable resin and comprising a metal core with less flexibility than the suture 68 is provided at the distal end of the suture 68, the suturing wire 109 may be readily inserted through the needle 5, needle guide 106b, guide tube 107, needle guide 106a and needle 100, thus improving operability and shortening the treatment time. Since the push wire 111 with less flexibility than the suture 68 is connected to the proximal side of the suture 68 and exposed at the proximal end of the needle grip 67 of the needle 5, insertion of the suturing wire 109 becomes easier than in the first embodiment in which the suture 68 is advanced, thus improving operability and shortening the treatment time.

Figure 37A:
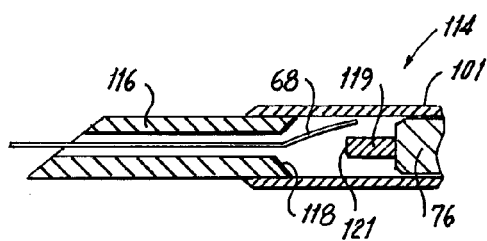
FIGS. 37(a) and 37(b) are operational views illustrating a state of receiving the suture by the needle at the side for receiving the suture according to a third embodiment.
Figure 37B:
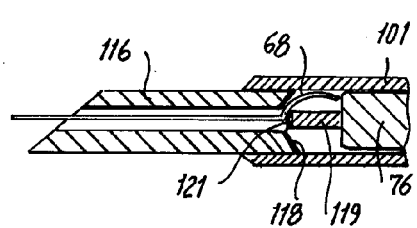
Figure 38:
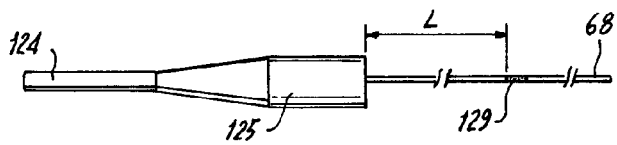
FIG. 38 is an external overview of a portion of the suture extending from a slider of the operation unit of the third embodiment.
Figure 39:
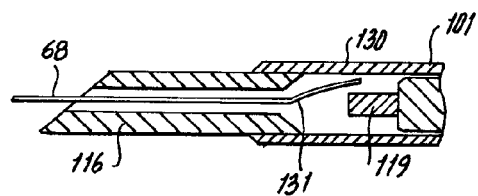
FIG. 39 is a view for showing a modification example of the needlepoint at the side for receiving the suture of the third embodiment.
Figure 40:
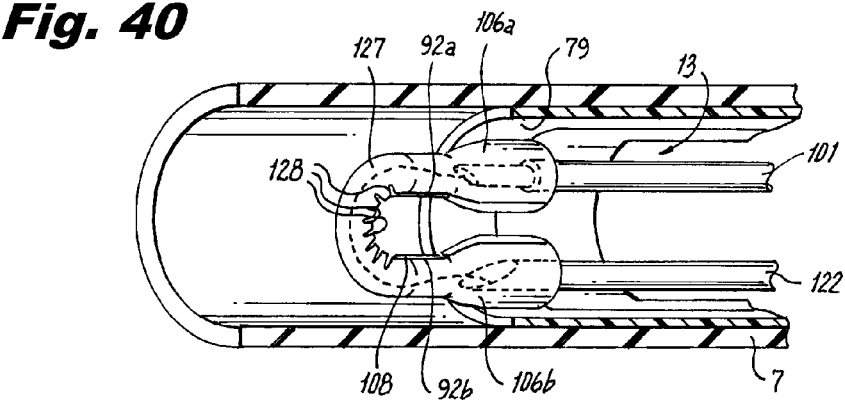
FIG. 40 is a vertical cross-sectional view of the distal end of the overtube of the third embodiment.
Figure 41:
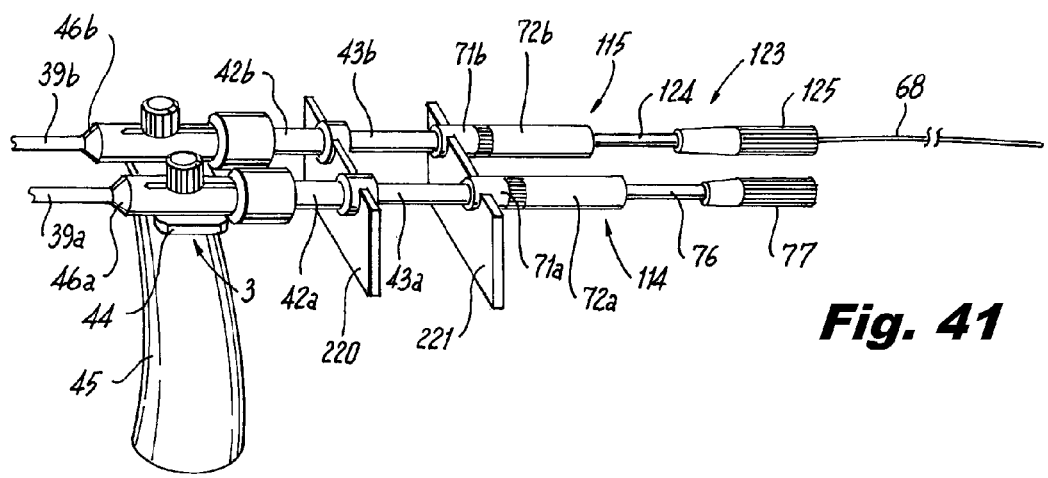
FIG. 41 is an external overview of the operation unit of the third embodiment.
Figure 42:
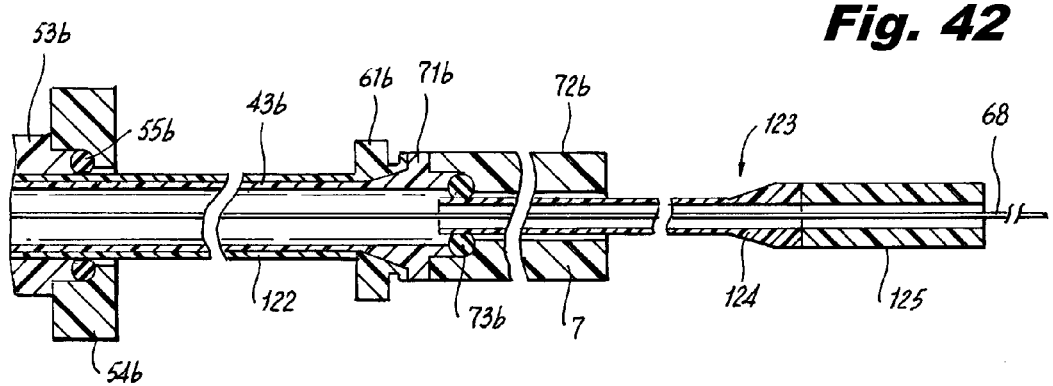
FIG. 42 is a vertical cross- sectional view of the proximal end of the needle of the third embodiment.

A third embodiment of the tissue puncturing system will now be described with reference to FIGS. 37 through 42. FIGS. 37(a) and 37(b) are operational views for showing a state of receiving the suture by the needle at the side for receiving the suture. FIG. 38 is an external overview of a portion of the suture extending from a slider of the operation unit. FIG. 39 is a view for showing the modification example of the needlepoint at the side for receiving the suture. FIG. 40 is a vertical cross-sectional view of the distal end of the overtube. FIG. 41 is an external overview of the operation unit. FIG. 42 is a vertical cross-sectional view of the proximal end of the needle 115. Descriptions will be given only where different from the first and second embodiments. Referring now to FIG. 41, in this embodiment, the needles 5 and 100 are replaced by needles 114 and 115. The needle 114 comprises a needle distal end 116, needle sheath 101, needle grip distal part 71a, needle grip proximal part 72a, O-ring 73a (not shown), and suture fixing device 117. The needle sheath 101 is connected to the distal end of the needle grip distal part 71a. The constructions of the needle grip distal part 71a, needle grip proximal part 72a, and O-ring 73a are same as for needle 6 of the first embodiment. As shown in FIG. 37, the outer diameter of the needle distal end 116 is slightly smaller than the inner diameter of the needle sheath 101, and the proximal side of the needle distal end 116 is fixed in the internal channel at the distal end of the needle sheath 101.

The proximal end surface of the needle distal end 116 has a conical tapered part 118. The suture fixing device 117 is the same as the suture forceps 74 of the first embodiment except that the grasper 75 is replaced by a suture fixing part 119. The suture fixing part 119 is connected to the distal end of the operation member 76. The suture fixing part 119 has an outer diameter smaller than that of the operation member 76. The clearance between the external surface of the suture fixing part 119 and the internal surface of the needle sheath 101 is larger than the outer diameter of the suture 68, which is to be mentioned later. Tapered part 121 tapered at substantially the same angle as the tapered part 118 is provided on the distal end surface of the suture fixing part 119. The needle distal end 116 and the suture fixing part 119 are formed from metal materials difficult to deform such as stainless steel or relatively rigid plastic materials.

The needle 115 comprises a needle body 122, needle grip distal part 71b, needle grip proximal part 72, O-ring 73b, and suture feeder 123. The needle body 122 is connected to the distal end of the needle grip distal part 71b. The constructions of the needle grip distal part 71b, needle grip proximal part 72b, and O-ring 73b are same as the needle 6 of the first embodiment. As shown in FIG. 38, the suture feeder 123 comprises a slider 124 and elastic grip 125. The slider 124 has an internal channel and is formed from a metal material such as stainless steel or a hard plastic material. The slider 124 is slidable in the internal channels of the needle body 122, needle grip. distal part 71b and needle grip proximal part 72b. A larger diameter part 126 with outer diameter larger than the inner diameter of the O-ring 73b is provided at the distal end of the slider 124 and distal to the O-ring 73b.

When the slider 124 is pulled from the needle grip proximal part 72b toward the proximal side, the larger diameter part 126 comes into contact with the O-ring 73b to prevent the slider 124 from being pulled off from the needle grip proximal part 72b. The elastic grip 125 formed from a rubber such as silicone rubber of fluoro-rubber or various thermo plastic elastomers is connected to the proximal side of the slider 124. Both the slider 124 and elastic grip 125 have an internal channel. A suture 68 is pre-set in the needle 115 as in the first embodiment. The slider 124 and elastic grip 125 have an inner diameter to allow the suture 68 to slide through easily. As shown in FIG. 40, multiple vertical slits 128 are provided in the side of the proximal end of the guide tube 127 in addition to the guide slit 108, which is similar to the guide tube 107 in the second embodiment. The vertical slit 128 extends substantially perpendicular to the guide slit 108. The vertical slit 128 has a width smaller than the outer diameter of the suture 68 to prevent the suture 68 passing through. An index 129 is provided on the suture 68 exposed toward the proximal end of the elastic grip 125.

The length L between the proximal end of the elastic grip 125 and the index 129 is equal to the distance formed when the distal end of the suture 68 passes through the needle guide 106a, guide tube 127, and the needle guide 106b and further proceeds several millimeters from the proximal end of the needle distal end 116 toward the proximal side. The inner sheath sliders 42a and 42b are connected via the inner sheath connecting member 220, but remain detachable. Similarly, the needle sliders 43a and 43b are connected via the needle connecting member 221, but remain detachable. As shown in FIG. 39, a transparent sheath section 130 may be provided at the distal end of the needle sheath 101 of the needle 114 instead of the index 129 on the suture 68. The transparent sheath section 130 is formed of a plastic material with a relatively high transparency such as polycarbonate. In this case, an index 131, which can be helical in shape for example, is preferably provided at the distal end of the suture 68.

An operation of the second embodiment of the tissue puncturing system will now be described. Descriptions will be given only where different from the first and second embodiments. When the inner sheaths 4a and 4b protrude from the needle lumens 11a and 11b, one of the inner sheath sliders 42a and 42b is advanced toward the distal end. Then the other inner sheath slider connecting to the first one via the inner sheath connecting member 220 follows to cause the inner sheaths 4a and 4b to protrude simultaneously. The needles 114 and 115 are also caused to protrude by operating one of the needle sliders 43a and 43b via the needle connecting member 221. After the needles 114 and 115 puncture the sutured tissues 97a and 97b, the elastic grip 125 collapses to pinch the suture 68 in the elastic grip 125. In this state, the slider 124 is advanced toward the distal end.

The suture 68 is then also advanced toward the distal end in the needle 114 for the same distance as the movement of the slider 124. The proximal end of the slider 124 is then held and pulled toward the proximal side. At this stage, the suture 68 does not move. The procedure is repeated until the index 129 on the suture 68 reaches the proximal end of the elastic grip 125 and passes the distal end of the suture 68 through the needle guide 106b, guide tube 127, needle guide 106a, and needle distal end 116 into the needle sheath 101. The operation knob 77 on the suture fixing device 117 is pressed toward the distal end to advance the suture fixing part 119 until it butts up against the proximal end surface of the needle distal end 116.

As shown in FIG. 37(b), the suture 68 is held between the tapered parts 118 and 121 and fixed to the needle 114. With the suture 68 fixed in the needle 114, the needles 114 and 115 are removed from the sutured tissues 97a and 97b. A part of the suture 68 passes between the needles 114 and 115 passes through the guide slit 108 of the guide tube 127, vertical slit 128, and guide slits 92a and 92b in the needle guides 106a and 106b and is removed from the needle guides 106a and 106b. As in FIG. 27 of the first embodiment, a part of the suture 68 extends between the exiting points 113a and 113b penetrated by the needles 114 and 115 and comes into contact with the sutured tissue 97b. Then the suture 68 extending from the proximal end of the elastic grip 125 is released and the overtube 2 and endoscope 9 are removed from the patient's body. When the transparent sheath section 130 is provided at the distal end of the needle sheath 101, while observing the images from the endoscope 9 it is confirmed that the suture 68 enters the transparent sheath section 130 and the operation knob 77 on the suture fixing device 117 is pressed. The index 131 provided at the distal end of the suture 68 will facilitate the confirmation of the distal end of the suture 68 under endoscopic observation.

In addition to the effects of the first embodiment, the effects described below are obtained. Since the suture 68 is held by the needle distal end 116 and the suture fixing part 119 formed of a material which is hard to deform and fixed to the needle 114, the fixing is more reliable than in the second embodiment. Since a suture feeder 123 is used instead of holding the flexible suture 68 and inserting it in the needle as in the first embodiment, the suture 68 may be more easily inserted into the needle 115, thus improving operability and shortening the treatment time. The position of the suture 68 may be confirmed with an index provided on the suture 68 or the transparent sheath section 130 on the needle sheath 101, thus improving operability and shortening the treatment time. Since the inner sheath sliders 42a and 42b, and the needle sliders 43a and 43b respectively are connected via the inner sheath connecting member 220 and the needle connecting member 221, operation of only one of the inner sheath sliders or the needle sliders is required, thus improving operability and shortening the treatment time.

Figure 43:
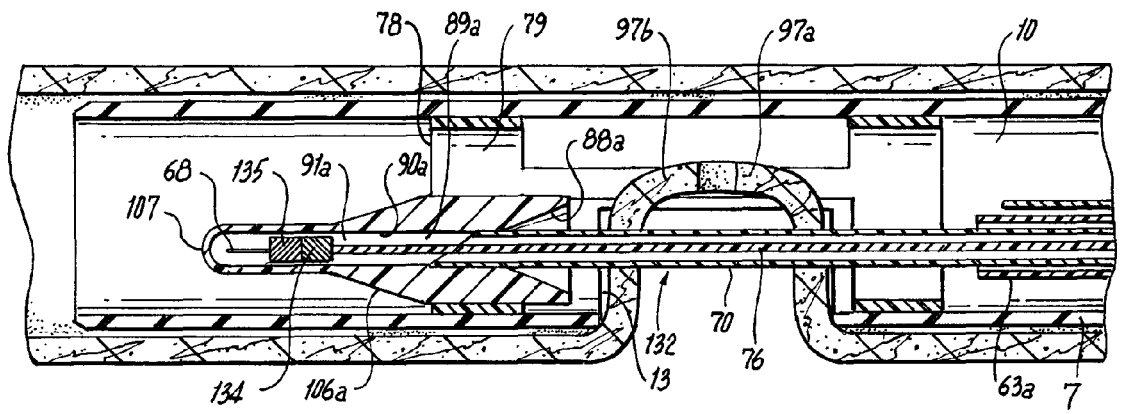
FIG. 43 is a view illustrating receiving the suture by the needle at the side for receiving the suture according to a fourth embodiment.
Figure 44:
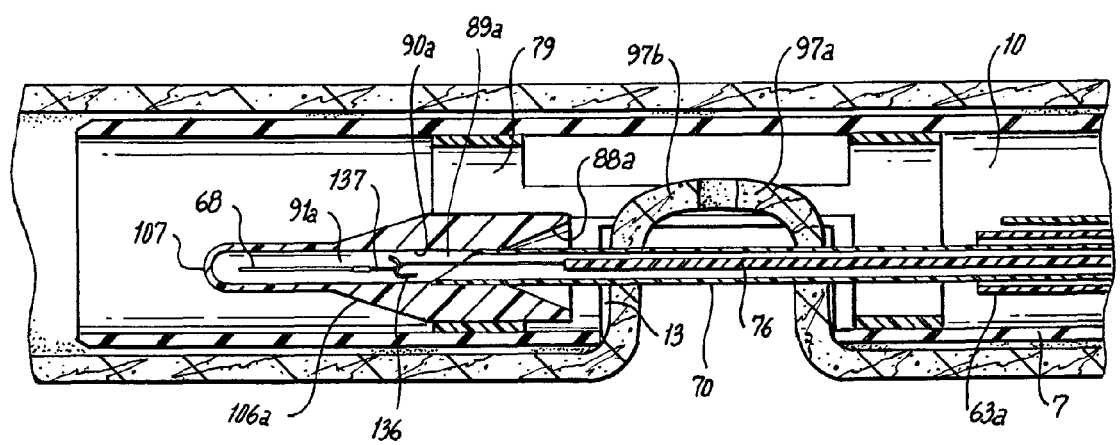
FIG. 44 is a view illustrating modification examples according to the fourth embodiment, and showing a state of receiving the suture.

A fourth embodiment of the tissue puncturing system will now be described with reference to FIGS. 43 through 46. FIG. 43 is a view for showing a state of receiving the suture by the needle at the side for receiving the suture. FIG. 44 is a view for showing one of the modification examples according to the fourth embodiment, and showing a state of receiving the suture. FIG. 45 is a cross-sectional view for showing only the front end of the needlepoint of other modification example according to the fourth embodiment. FIG. 46(a) and FIG. 46(b) are views for showing a state of receiving the suture according to the same modification embodiment as that shown in FIG. 45. Descriptions will be given only where different from the first and second embodiments. Referring now to FIG. 43, needle guides 106a and 106b are provided on the distal annular part 79 of the reinforcing member 78 as in the second embodiment and are connected by the guide tube 107. Two needles comprise a needle 132 and the needle 5 (FIG. 1) shown in the first embodiment. The needle 132 has substantially the same construction as the needle 6 (FIG. 1) of the first embodiment except that the grasper 75 at the distal end of the suture forceps 74 is replaced by a suture holder which has a different structure. The suture 68 with a means of engagement, which is held by the suture holder at the distal end, is pre-set.

One example of the suture holder is shown in FIG. 43 and comprises a permanent magnet 134 formed of barium ferrite or the like and provided at the distal end of the operation member 76. Another permanent magnet 135 is also connected as the means of engagement at the distal end of the suture 68. Another suture holder is a U-shaped hook 136 provided at the distal end of the operation member 76 as shown in FIG. 44. A hook 137 is also provided at the distal end of the suture 68. The hooks 136 and 137 may be formed from a metal such as stainless steel. Yet another suture holder comprises a grasper 138 and is provided at the distal end of the operation member 76 as shown in FIGS. 45, 46(a), and 46(b). The grasper 138 is formed from a tubular member made of a relatively elastic metal material such as stainless steel or nitinol, or a plastic material such as polyethylene, polypropylene, polyamide, or fluorocarbon resin. The grasper 138 has an internal channel and the inner diameter is smaller on the distal side than on the proximal side. Cross-shaped slits 139 longitudinally extend on the grasper 138 up to the portion with the larger inner diameter.

The grasper 138 has its distal end opening circumferentially from the proximal ends of the slits 139 under the no load condition, forming four claws 140. A convex surface 141 is formed at the distal end of each claw 140. The claws 140 are closed by withdrawing the holding part 138 into the needle 132. As shown in FIG. 46(b), a larger diameter member 142 is connected to the distal end of the suture 68 as a means of engagement. The outer diameter of the larger diameter member 142 is smaller than the inner diameter of the proximal side of the grasper 138 and larger than the inner diameter of the distal side. A grasping channel 133 with expanded inner diameter is formed proximal to the suture channel 91a on the needle guide 106a. The inner diameter of the grasping channel 133 is roughly the same as the opening width of the claws 140 under the no load condition.

An operation of the fourth embodiment of the tissue puncturing system will now be described. Descriptions will be given only where different from the first and second embodiments. After the needles 5 and 132 puncture the sutured tissues 97a and 97b, the suture 68 is made to protrude from the needle 5, and it is advanced through the needle guide 106b and guide tube 107. The operation knob 77 on the needle 132 is pressed toward the distal end to cause the suture holder to protrude at the distal end of the operation member 76 from the needle 132. The means of engagement is engaged at the distal end of the suture 68 and the suture holder in guide tube 107 or the needle guide 106a. Then the operation knob 77 is returned to withdraw the means of engagement into the needle 132 and to fix it. The suture holder and means of engagement, being permanent magnets 134 and 135, are engaged by magnetic force. The suture holder and means of engagement, being hooks 136 and 137, are engaged by being hooked to each other. The suture holder and means of engagement, being grasper 138 and the larger diameter member 142, are engaged as described below. When the operation knob 77 is pushed, the grasper 138 protrudes from the needle 132, and the claws 140 open in the grasping channel 133. The suture 68 is advanced such that the larger diameter member 142 is situated proximal to the convex surface 141. The operation knob 77 is returned to close the claws 140 and retract them into the needle 132. The convex surface 141 mates with the larger diameter member 142 to force the latter to be retracted and fixed in the needle 132. The benefits obtained by the tissue puncturing system of the fourth embodiment are the same as for the third embodiment discussed above.

A fifth embodiment of the tissue puncturing system will now be described with reference to FIG. 47. Descriptions will be given only where different from the fourth embodiment. Two needles comprise a needle 143 and the needle 5 (FIG. 1) shown in the first embodiment. The suture 68 is pre-set in the needle 5, and a T bar 144 is attached at the distal end of the suture. The T bar 144 is formed from a bar sheet or pipe made of a metal such as stainless steel or a hard and slidable plastic material such as polyacetal. The T bar 144 has an outer diameter which can pass through the internal channels of the needle guides 106a and 106b, and guide tube 107. The distal end of the suture 68 is located substantially at the center of the T bar 144. The needle 143 is provided with a stopper member 146 in the vicinity of the distal end of the internal channel of the needle body 145; otherwise it has the same construction as the needle 5. The stopper member 146 has an internal channel, which is provided with a conical tapered surface 147 at the distal end and a stopper surface 148 at the proximal end. The inner diameter of the stopper member 146 is slightly larger than the sum of the outer diameters of the T bar 144 and the suture 68.

An operation of the tissue puncturing system of the fifth embodiment will now be described. Descriptions will be given only where different from the fourth embodiment. After the needles 5 and 143 puncture the sutured tissues 97a and 97b the suture 68 is made to protrude from the needle 5, and advance it through the needle guide 106b, guide tube 107, needle guide 106a, and needle body 145. When the suture 68 is further advanced, the T bar 144 passes through the internal channel of the stopper member 146 and reaches the proximal side of the stopper surface 148. The tapered surface 147 facilitates the passage into the proximal aperture of the stopper member 146. The needles 5 and 143 are removed from the sutured tissues 97a and 97b. The end surface of the T bar 144 is then hooked by the stopper surface 148 and connected and fixed with the needle 143 inside. In addition to the effects of the first embodiment, the suture 68 may be fixed to the needle 143 simply by advancing the suture 68, thus improving operability and shortening the treatment time.

Figure 48:
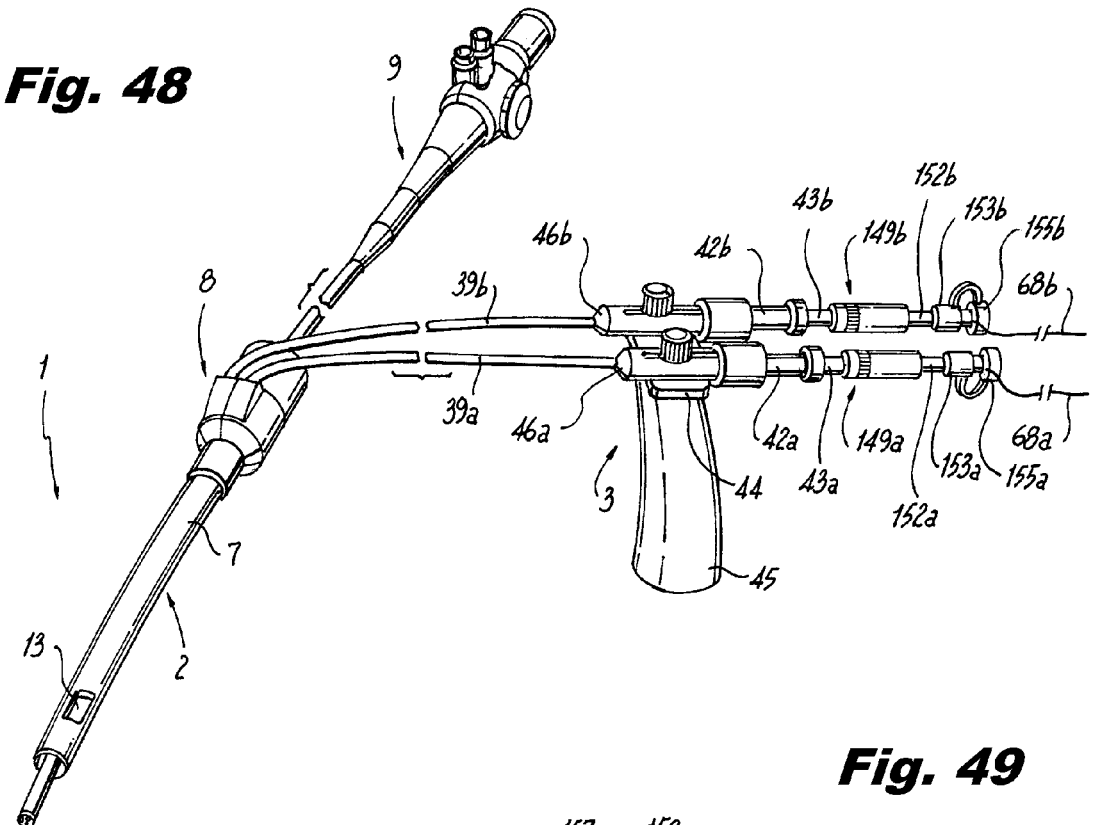
FIG. 48 is an external overview of a tissue puncturing system according to a sixth embodiment.
Figure 49:
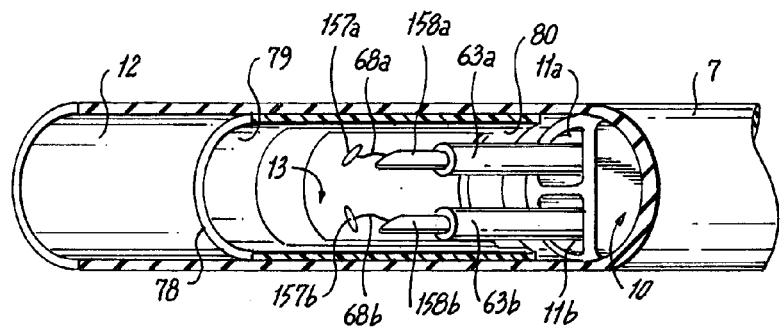
FIG. 49 is a partial cross-sectional view of the overtube of FIG. 48.
Figure 50:
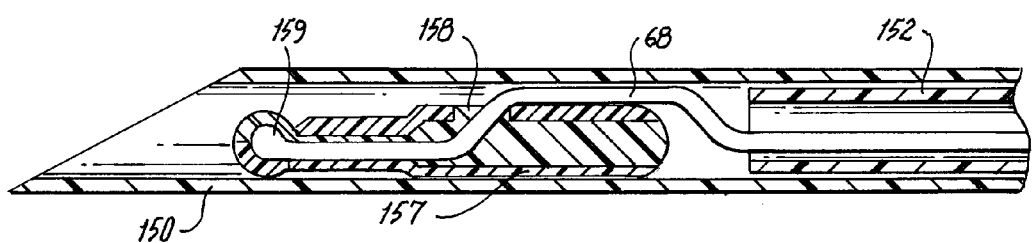
FIG. 50 is a vertical cross-sectional view of the distal end of a needle of FIG. 49.
Figure 51:
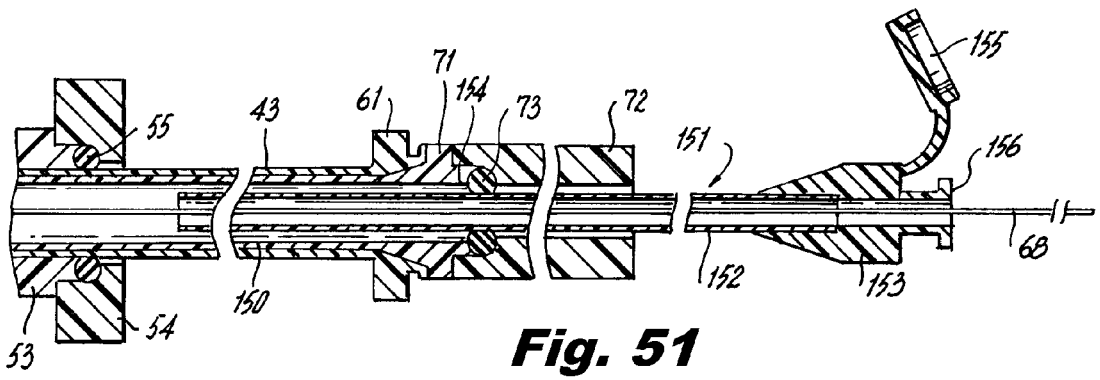
FIG. 51 is a vertical cross-sectional view of the proximal side of the needle of FIG. 50.
Figure 52:
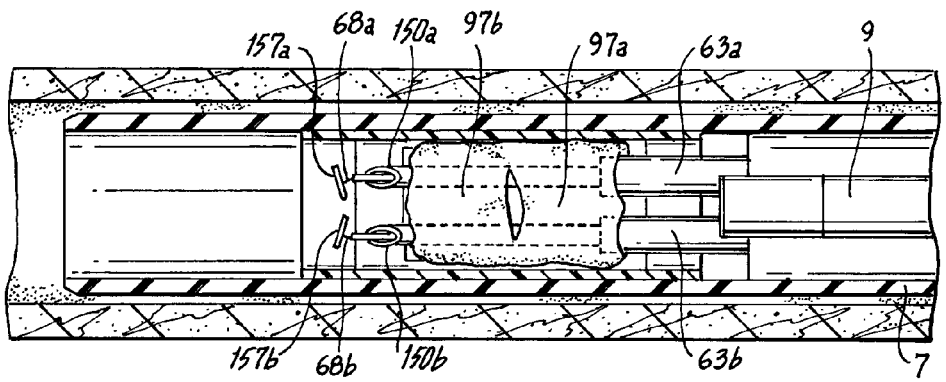
FIGS. 52 to 54 are operational views for illustrating tissue being put in a suture.
Figure 53:
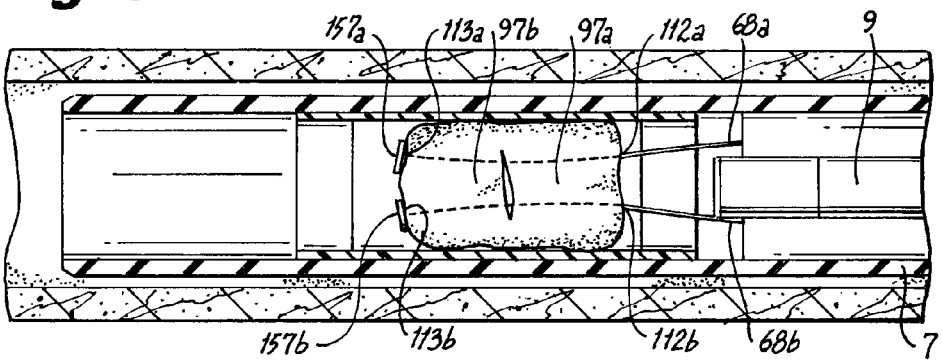
Figure 54:
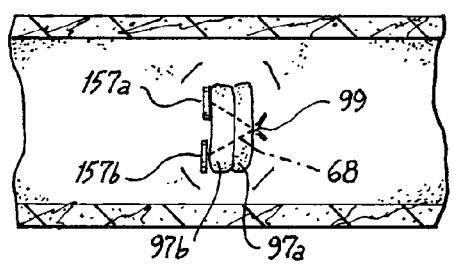

A sixth embodiment of the tissue puncturing system will now be described with reference to FIGS. 48 through 54. FIG. 48 is an external overview of the entire tissue puncturing system. FIG. 49 is a partial cross-sectional view of the overtube. FIG. 50 is a vertical cross-sectional view of the distal end of the needle 149. FIG. 51 is a vertical cross-sectional view of the proximal side of the needle 149. FIG. 52 to FIG. 54 are operational view for showing a state such that the tissue is put in a suture. Descriptions will be given only where different from the first through fifth embodiments.

Two needles comprise needles 149a and 149b having the same structure. The needles 149 respectively comprise a needle body 150, needle grip distal part 71, needle grip proximal part 72, O-ring 73, and pusher tube 151. As shown in FIGS. 50 and 51, the constructions of the needle body 150, needle grip distal part 71, needle grip proximal part 72, and O-ring 73 are the same as the needle 6 of the first embodiment. The pusher tube 151 slides in the needle 149. The suture 68 is pre-set in the needle 149 and pusher tube 151. The pusher tube 151 comprises a sheath 152, grip 153, stopper 154, and cap 155. The sheath 152 is formed from a flexible tubular member made of a metal material such as stainless steel or nitinol, or a plastic material such as polyethylene, fluorocarbon resin, polyamide, or polyimide. The sheath 152 has an inner diameter of approximately 0.3 to 1 mm, which allows the suture 68 to slide easily. Its outer diameter is slightly larger than the inner diameter of the O-ring 73 and preferably approximately 0.4 to 1.4 mm, and air-tightness may be maintained between the O-ring 73 and the sheath 152.

The grip 153 is connected to the proximal end of the sheath 152.

The grip 153 also has an internal channel to enable passage of the suture 68, which is connected to the internal channel in the sheath 152. The grip 153 is formed of a metal material such as stainless steel or aluminum, or a hard plastic material such as polypropylene, ABS polycarbonate, polyacetal, or polysulfone. The stopper 154 is provided on the periphery of the sheath 152 distal to the O-ring 73. The stopper 154 has an outer diameter larger than the inner diameter of the O-ring 73.

When the pusher tube 151 is pulled toward the proximal side until the stopper 154 butts up against the O-ring 73, the distal end of the sheath 152 is located approximately 15 to 20 mm proximal to the distal end of the needle body 150. When the pusher tube 151 is pulled toward the distal side until the grip 153 butts up against the needle grip proximal part 72, the distal end of the sheath 152 is located approximately 5 to 20 mm distal to the distal end of the needle body 150. A suture insertion port 156 is provided at the proximal end of the grip 153. A cap 155 is provided in the vicinity of the proximal end of the grip 153 as in the first embodiment. The cap 155 may be used to cover the suture insertion port 156 and seal it from the outside.

A T bar 157 is connected to the distal end of the suture 68. The T bar 157 is formed from a metal pipe such as stainless steel and has a length greater than the puncture hole created when the needle body 150 penetrates the sutured tissues 97a and 97b. The length is preferably approximately 5 to 10 mm. The inner diameter is approximately 0.3 to 0.5 mm. The outer diameter of the T bar 157, when combined with the outer diameter of the suture 68, is set smaller than the inner diameter of the needle body 150, and the T bar 157 is slidable in the needle body 150. A side hole 158 is provided at the center point or the center of gravity of the T bar 157. The distal end of the suture 68 is inserted via the side hole 158 into the T bar 157 and the end is exposed to form a knot 159. The vicinity of the end of the T bar 157, through which the suture 68 is inserted, is crimped to fix the suture 68. To improve the fixation between the T bar and suture 68, an adhesive agent is injected from the side hole 58 in the T bar 157.

The periphery of the knot 159 is also fixed with an adhesive agent. Both ends of the T bar 157 are rounded to prevent damage to the tissue in body cavities.

The T bar 157 is pre-set distal to the sheath 152 in the internal channel of the needle body 150 with the pusher tube 151 pulled toward the proximal side until the stopper 154 butts up against the O-ring 73. The suture 68 is inserted via the distal end of the sheath 152 into the sheath and extends to the proximal side of the grip 153. The length of the suture 68 exposed toward the proximal side of the grip 153 is approximately 10 cm. With the suture 68 set in the needle 150, the cap 155 covers the suture insertion port 156. Thus the suture 68 is held between the cap 155 and the suture insertion port 156 and connected to the pusher tube 151. At the same time, the suture insertion port 156 may be maintained in an airtight state. No needle guide shown in the first through fifth embodiments is provided on the distal annular part 79 on the reinforcing member 78 of the overtube 2.

An operation of the tissue puncturing system of the sixth embodiment will now be described. Descriptions will be given only where different from the first embodiment. After the needles 149a and 149b puncture the sutured tissues 97a and 97b, the grips 153a and 153b are advanced toward the distal end until the grips 153a and 153b butt up against the needle grip proximal parts 72a and 72b. The sheaths 152a and 152b are also advanced toward the distal end to cause the T bars 157a and 157b to protrude from the distal ends of the needle bodies 150a and 150b and to leave the T bars 157a and 157b in the body cavity distal to the sutured tissue 97b. The caps 155a and 155b are removed from the suture insertion ports 156a and 156b and the suture 68 and pusher tube 151 are released. This frees the sutures 68a and 68b to slide against the needles 149a and 149b and pusher tubes 151a and 151b. The needles 149a and 149b are removed from the sutured tissues 97a and 97b and retracted into the needle lumens 11a and 11b. The inner sheaths 4a and 4b are also retracted into the needle lumens 11a and 11b. At this stage, the T bars 157a and 157b are hooked by the sutured tissue 97b and the sutures 68a and 68b are fixed to the sutured tissues 97a and 97b. The suture 68 extending from the proximal side of the grip 153 is released and the overtube 2 and endoscope 9 are removed from the patient's body. As in the first embodiment, a knot 99 is made on the suture 68 coming out of the patient's body and the knot 99 is pushed into the body using a conventional knot pusher to ligate the part proximal to the sutured tissue 97a as shown in FIG. 54.

In addition to the effects of the first embodiment, the effects described below are obtained. It is not required to transfer the suture 68 between the two needles, thus improving operability and shortening the treatment time. Since the suture 68 is not required to be held by the receiving needle, the suture 68 cannot come off during removal of the overtube 2 from the patient's body. Thus, there is no possibility that one end of the suture 68 cannot be taken out of the patient's body. Since the suture 68 and T bar 157 protrude from the distal end of the needle 149 upon pushing the pusher tube 151, the flexible suture 68 may be more readily inserted than in the case of manual feeding the suture, thus improving operability and shortening the treatment time. No needle guide is required on the overtube 2 as in the first through fifth embodiments, thus facilitating the manufacturing process and reducing the manufacturing costs.

Figure 55:
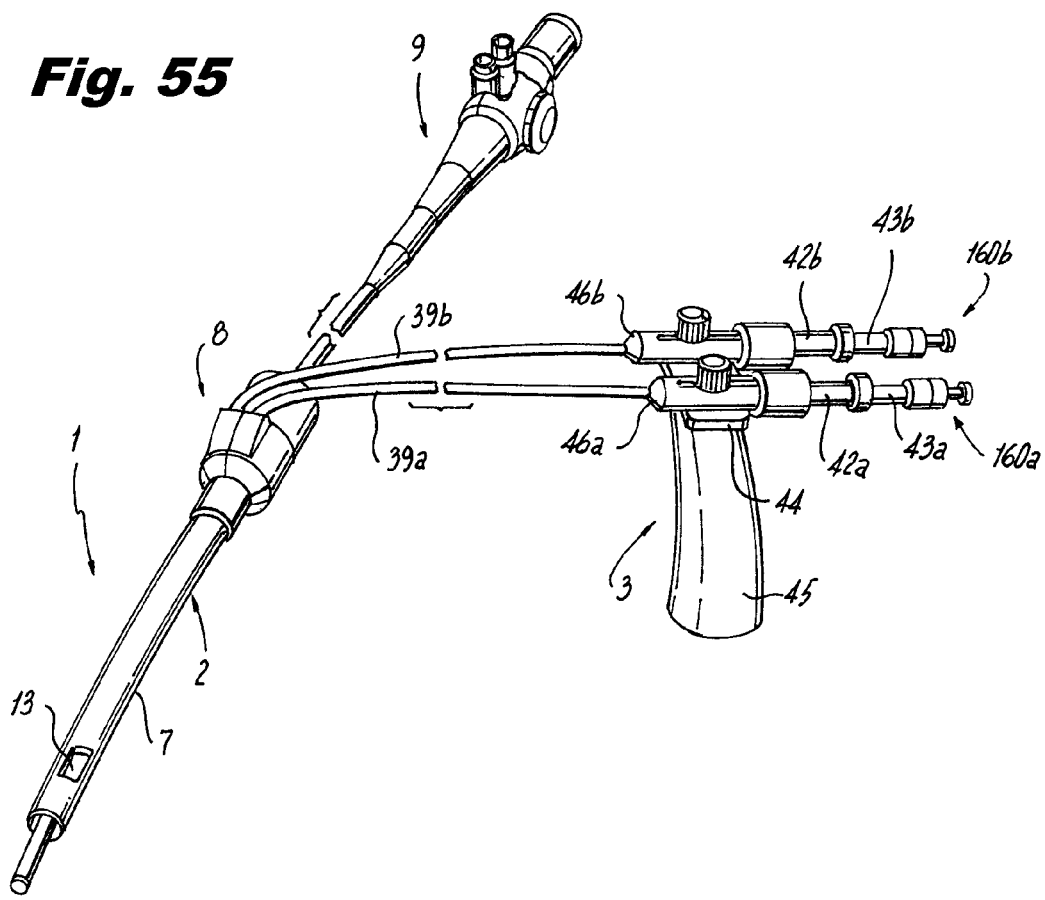
FIG. 55 is an external overview of a tissue puncturing system according to a seventh embodiment.
Figure 56:
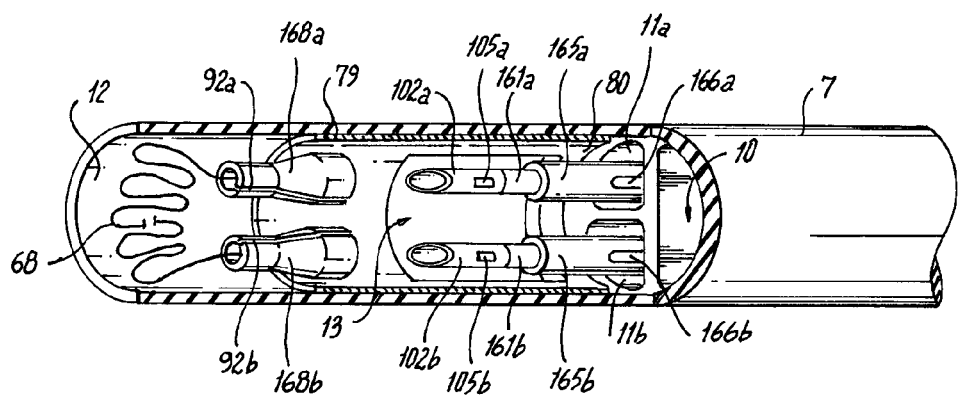
FIG. 56 is a partial cross-sectional view of the overtube of FIG. 55.
Figure 57:
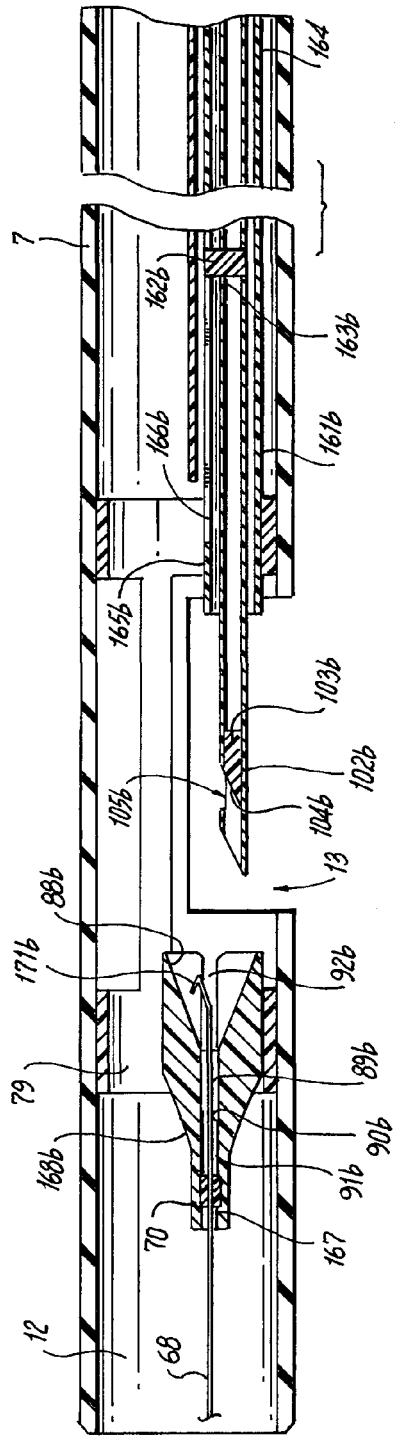
FIG. 57 is a vertical cross-sectional view of the needle guide and the front end of the overtube of FIG. 56, which is sectioned on a centerline of the needle.
Figure 58:
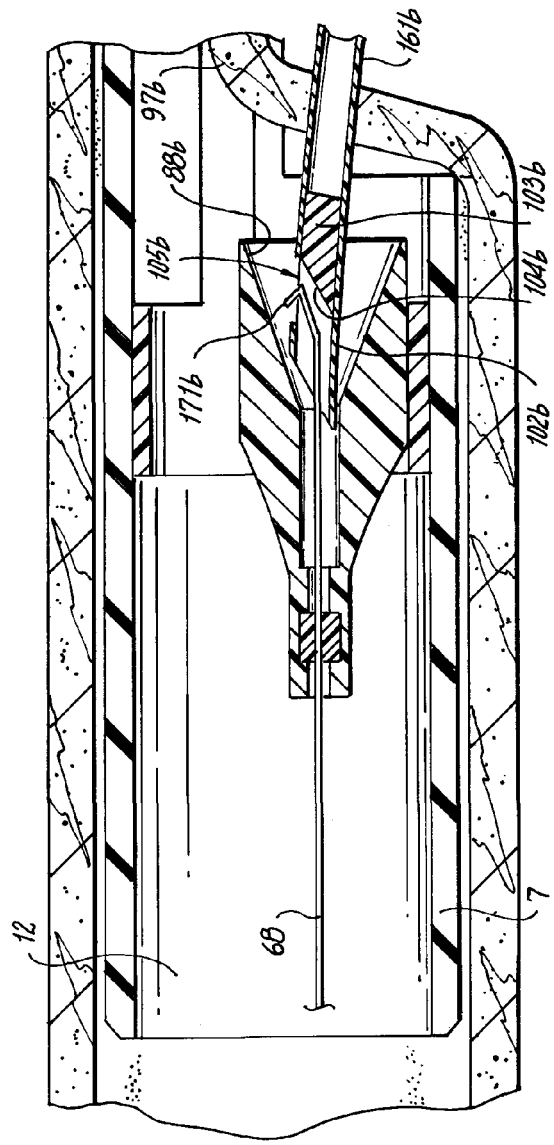
FIG. 58 is a view illustrating a front end of the needle being struck within the needle guide to be engaged with the end of the suture.
Figure 59:
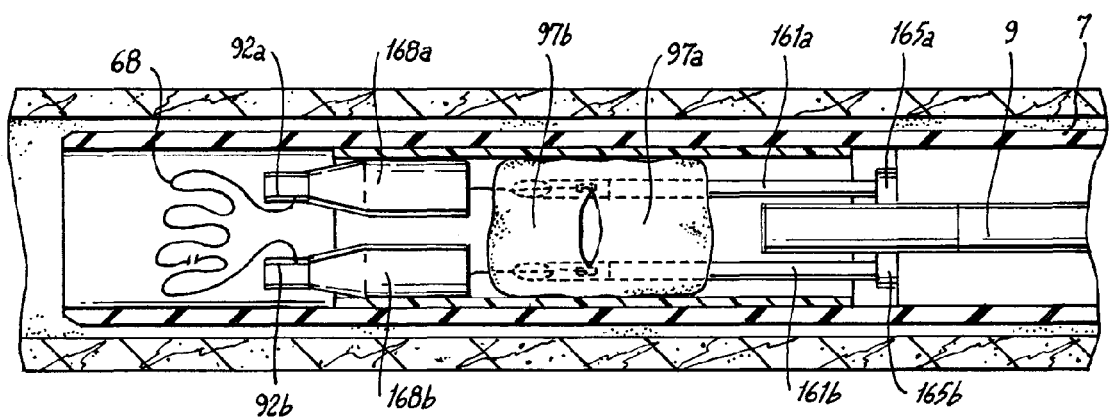
FIGS. 59 and 60 are operational views illustrating the needle being taken out from the tissue to put the suture through the tissue.
Figure 60:
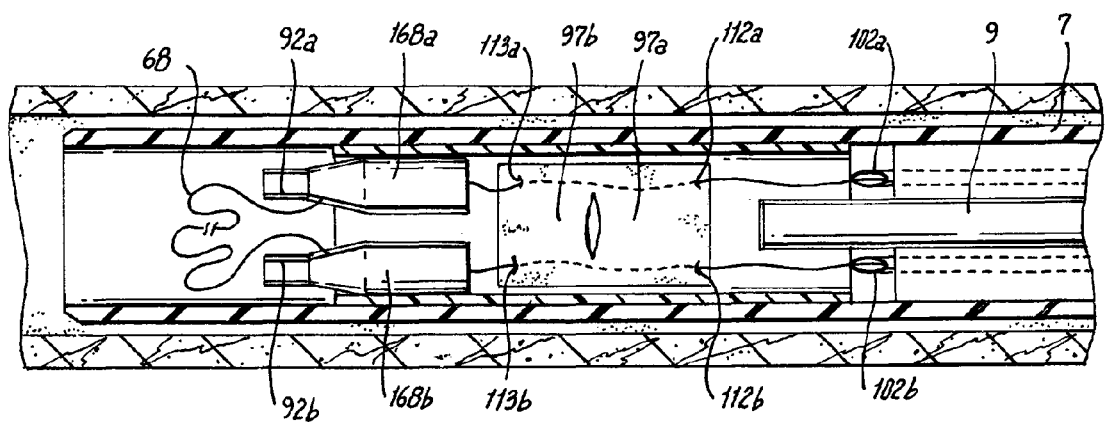
Figure 61:
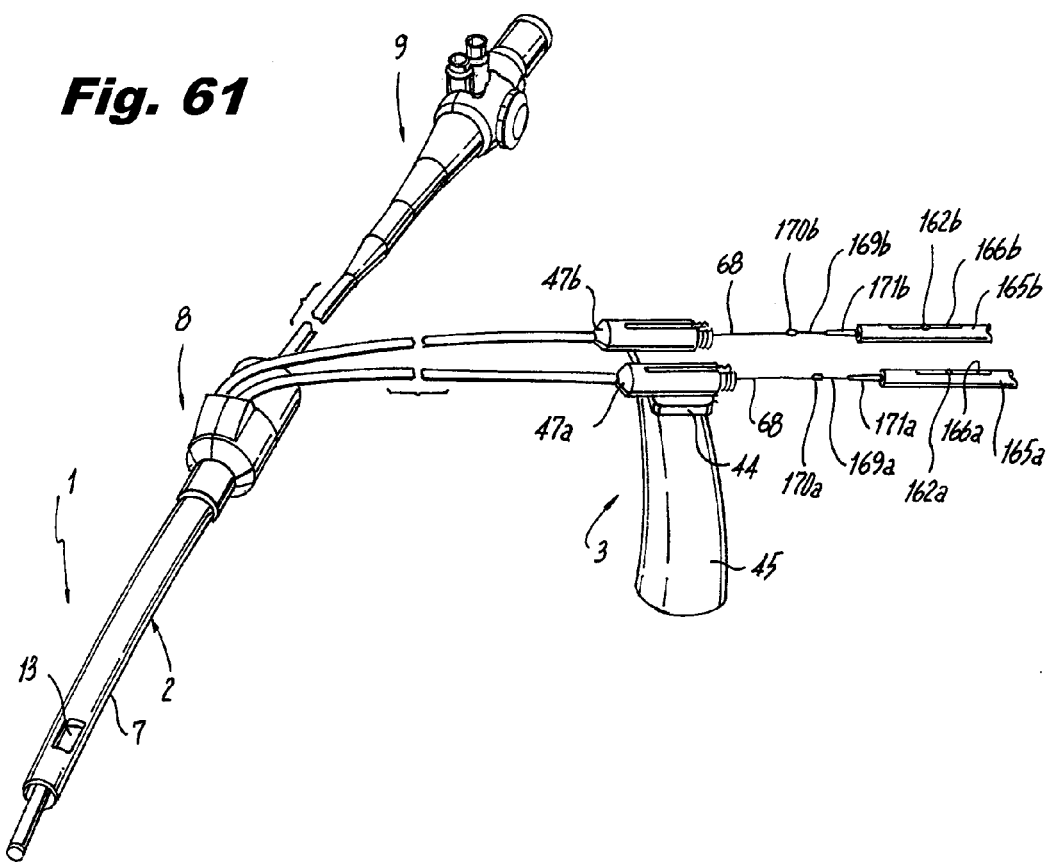
FIG. 61 is a view illustrating the needle being completely taken out from the operation unit.

A seventh embodiment of the tissue puncturing system will now be described with reference to FIGS. 55 through 61. FIG. 55 is an external overview of the entire tissue puncturing system. FIG. 56 is a partial cross-sectional view of the overtube. FIG. 57 is a vertical cross-sectional view of the needle guide and the front end of the overtube, which is sectioned on a centerline of the needle. FIG. 58 is a view for showing a state such that the front end of the needle is struck against within the needle guide to be engaged with the end of the suture. FIG. 59 and FIG. 60 are operational views for showing a state such that the needle is taken out from the tissue to put the suture through the tissue. FIG. 61 is a view for showing a state such that the needle has been completely taken out from the operation unit. Descriptions will be given only where different from the first and second embodiments. The two needles 160a and 160b have the same structure. The needles 160 respectively comprise a needle sheath 161, needle distal end 102, needle grip 67 (FIG. 4), guide member 103, and pin 162. The connection of the needle distal end 102, guide member 103, needle sheath 161, and needle grip 67 has the same construction as the needle 100 (FIG. 36) of the second embodiment. The needle sheath 161 comprises the needle sheath 101 of the second embodiment with a pinhole 163 added. The two inner sheaths 164a and 164b have the same structure. The inner sheaths 164 have the same construction as the inner sheaths 4, except that a pin slit 166 extending longitudinally along the side of the tube 165 is provided. With the needle 160 inserted in the inner sheath 164 in advance, the pin 162 is a press-fit and fixed in the pinhole 163 via the pin slit 166. The pin 162 has an outer diameter smaller than the width of the pin slit 166. A part of the pin 162 protrudes from the outer surface of the needle sheath 161, and the protruding part slides in the pin slit 166 as the needle 160 slides against the inner sheath 164. As shown in FIG. 59, needle guides 168a and 168b are provided on the distal annular part 79 of the reinforcing member 78. As shown in FIG. 57, the distal end of the suture channel 91 in the needle guide 168 has a smaller inner diameter, utilizing the difference in diameters to form a suture fixing surface 167. The width of the guide slit 92, unlike in the first embodiment, is preferably larger than the outer diameter of the suture 68. The construction other than the above is the same as for the needle guide 106 of the second embodiment.

The suture channels 91a and 91b are not connected via the guide tube 107 or the equivalent as in the second embodiment. As shown in FIG. 61, hooks 169a and 169b are attached to both ends of the suture 68 via connecting pipes 170. The hooks 169 are formed from relatively rigid metal wire such as stainless steel and provided with L-shaped bends 171 at their distal ends. The hooks 169 and connecting pipes 170 are pre-set in the suture channels 91. The end surfaces facing the sutures in the connecting pipes 170 come into contact with the suture fixing surface 167. The connecting pipes 170 have an outer diameter slightly larger than the inner diameter of the suture channels 91 and are a gentle fit in the suture channels 91. The fit is such that the connecting pipes 170 may be withdrawn with the force used to remove the needles 160 from the tissues being sutured. The connecting pipes 170 are set with the bends 171 facing in the same direction as the side holes 105 in the needles 160. The bends 171 are positioned in the internal channels of the tapered parts 88. The length of suture 68 is twice or more the length between the side opening 13 and the proximal end of the slider receivers 46 and is folded in the treatment lumen 12.

An operation of the tissue puncturing system of the seventh embodiment will now be described. Descriptions will be given only where different from the first embodiment. The needles 160a and 160b penetrating the sutured tissues 97a and 97b enter the needle guides 168a and 168b and butt up against the needle abutment surfaces 90a and 90b. The hooks 169a and 169b are inserted in the internal channels of the needle distal ends 102a and 102b. The bends 171a and 171b proceed along the tapered surfaces 104a and 104b of the guide members 103 and protrude out of the needle distal ends 102a and 102b through the side holes 105a and 105b. The rings 48a and 48b on the slider receivers 46a and 46b and the fixing screws 57a and 57b on the inner sheath sliders 42a and 42b are loosened. The needle sliders 43a and 43b are removed from the housings 47a and 47b with the inner sheath sliders 42a and 42b and the needles 160a and 160b remaining connected. When the needles 160a and 160b are withdrawn from the needle guides 168a and 168b, the bends 171a and 171b are hooked by the side holes 105a and 105b and are connected to the needles.

When removing the needles 160a and 160b, both ends of the suture 68 penetrate the sutured tissues 97a and 97b and are removed from the body (FIG. 61). When the needles are further withdrawn, the suture 68 passes through the guide slits 92a and 92b and becomes released from the needle guides 168a and 168b, and a part of the suture 68 ultimately comes into contact with the sutured tissue 97b between the exiting points 113a and 113b. After both ends of the suture 68 are removed from the housings 47a and 47b, the hooks 169a and 169b are removed from the needle distal ends 102a and 102b, and the suture 68 is cut to separate the hooks 169a and 169b and the connecting pipes 170 from the suture 68. The suture 68 extending from the proximal sides of the housings 47a and 47b is released and the overtube 2 and endoscope 9 are removed from the patient's body. In addition-to the effects of the first embodiment, the transfer of the suture 68 between two needles is not required, thus improving operability and shortening the treatment time.

Figure 62:
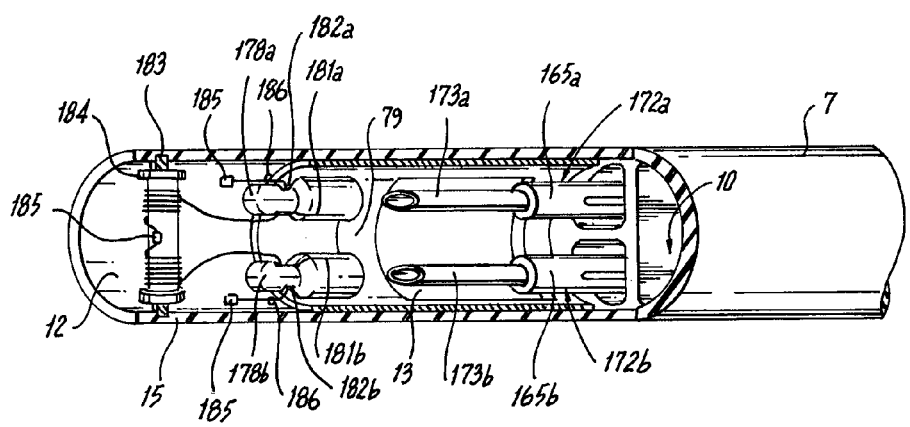
FIG. 62 is a partial cross-sectional view of the overtube of FIG. 61.
Figure 63:
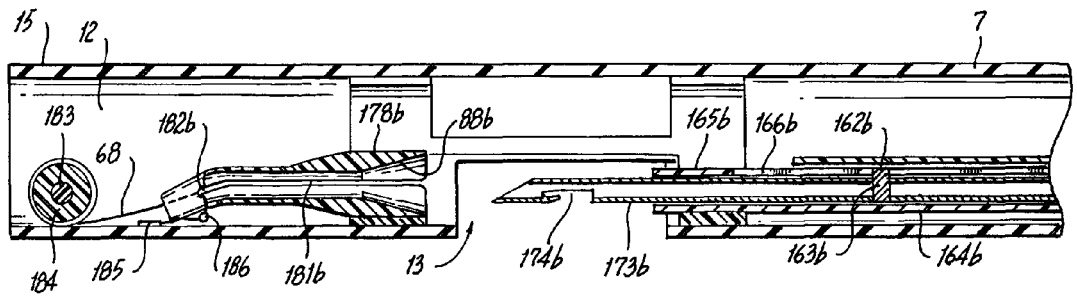
FIG. 63 is a vertical cross-sectional view of the needle guide and the front end of the overtube of FIG. 62, which is sectioned on a centerline of the needle.
Figure 64A:
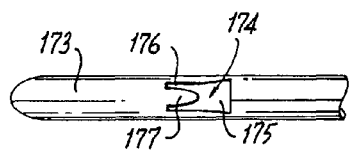
FIGS. 64(a) and 64(b) are a front view and a side view of a cutout at the front end of the needle, respectively.
Figure 64B:
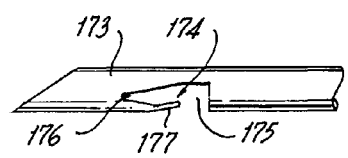
Figure 65:
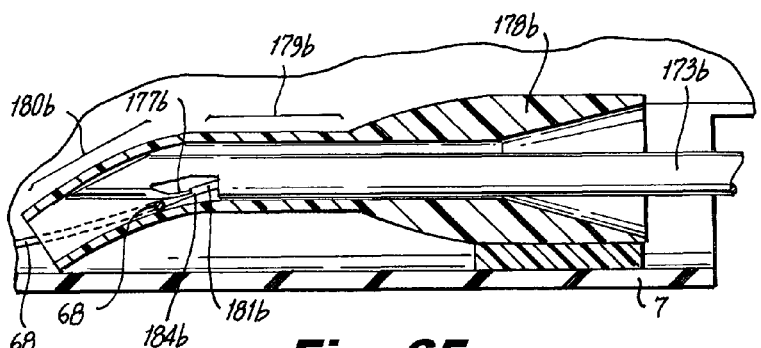
FIGS. 65 to 67 are vertical cross-sectional views of the needle guide and operational views illustrating the suture being engaged with the needle.
Figure 66:
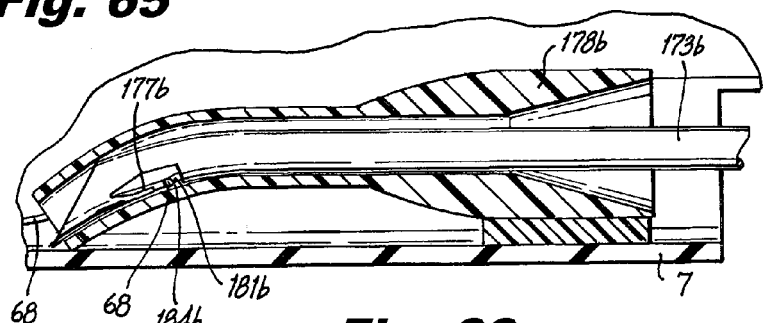
Figure 67:
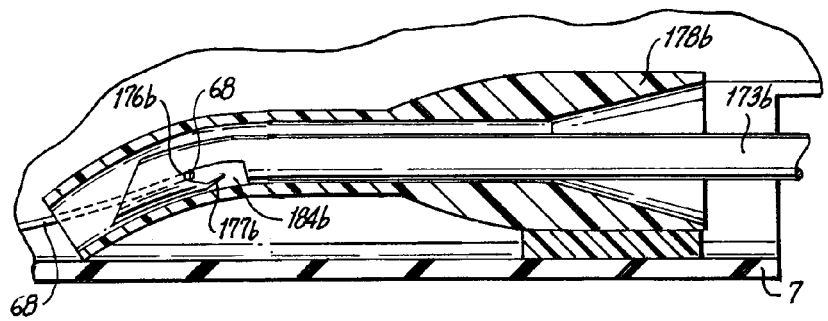
Figure 68:
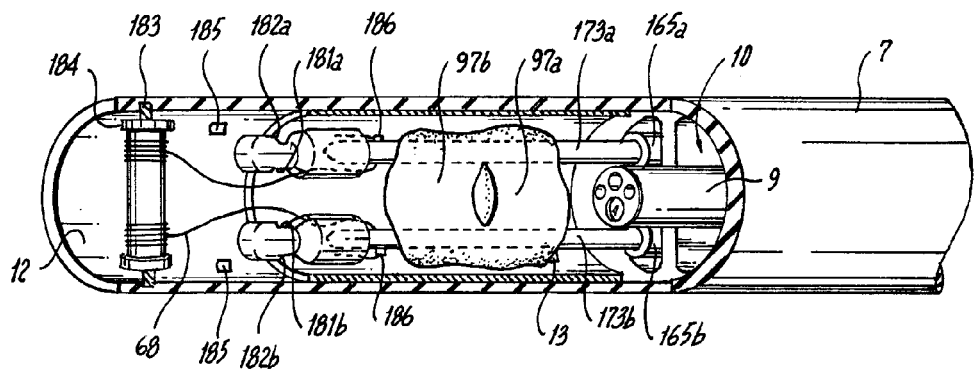
FIGS. 68 and 69 are operational views illustrating the needle being taken out from the tissue to put the suture through the tissue.
Figure 69:
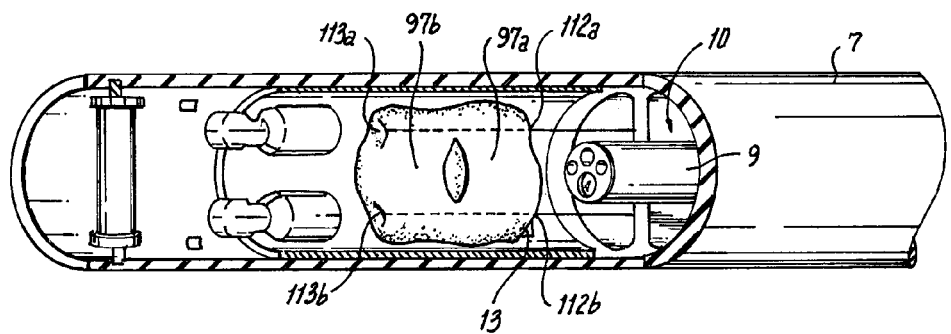
Figure 70:
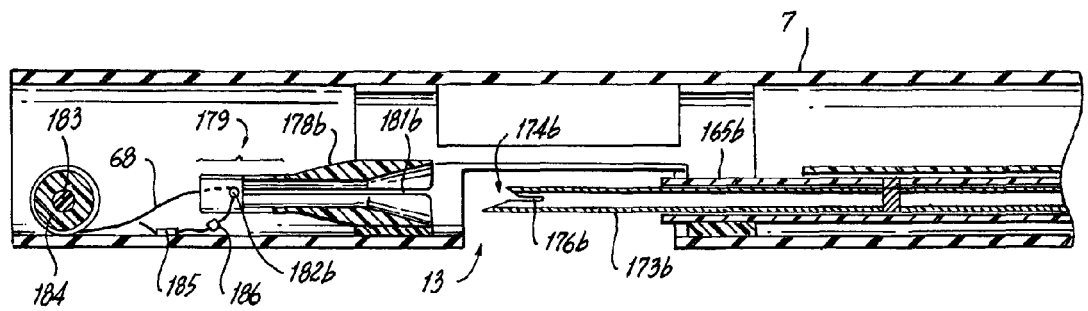
FIG. 70 is a vertical cross-sectional view illustrating a modification example according to the eighth embodiment.

An eighth embodiment. of the tissue puncturing system will now be described with reference to FIGS. 62 through 70. FIG. 62 is a partial cross-sectional view of the overtube. FIG. 63 is a vertical cross-sectional view of the needle guide and the front end of the overtube, which is sectioned on a centerline of the needle. FIG. 64(a) and FIG. 64(b) are a front view and a side view of a cutout at the front end of the needle, respectively. FIG. 65 to FIG. 67 are vertical cross-sectional views of the needle guide and operational views for showing a state such that the suture is engaged with the needle. FIG. 68 and FIG. 69 are operational views for showing a state such that the needle is taken out from the tissue to put the suture through the tissue. FIG. 70 is a vertical cross-sectional view for showing the modification example according to the eighth embodiment. Descriptions will be given only where different from the first and seventh embodiments. The two needles 172a and 172b have the same structure. The needles 172a and 172b each comprise a needle body 173, needle grip 67 (FIG. 4), and pin 162. The needle grip 67 is connected to proximal end of the needle body 173. A cutout 174 is provided in the vicinity of the distal end of the needle body 173. The cutout 174 is shaped as shown in FIG. 64 and comprises a guide port 175, fixing groove 176, and a hook 177. The fixing groove 176 is formed distal to the guide port 175 and has a width slightly smaller than the suture 68. The hook 177 is also formed distal to the guide port 175 and has its end facing the proximal side of the guide port 175.

The inner sheaths comprise- inner sheaths 164a and 164b as in the seventh embodiment. The needle body 173 is provided with a pinhole 163 and is connected to and can slide against the inner sheath 164 via the pin 162 as in the seventh embodiment. As shown in FIG. 65, needle guides 178a and 178b are provided on the distal annular part 79 of the reinforcing member 78. The distal end of the needle guide 178 has a straight part 179 and curved part 180. The direction of the curved part 180 is identical to the direction of the cutout 174 on the needle 172. A guide slit 181 is provided on the needle guide 178, and its distal end is positioned slightly toward the curved part 180 from the boundary between the straight part 179 and curved part 180 and slightly below the center axis of the internal channel in the curved part 180. The needle guide 178 has a side hole 182 on the opposite side of the distal end of the guide slit 181. The width of the guide slit 181 and the size of the side hole 182 are set to allow the suture 68 to pass through easily. The internal channel in the needle guide 178, unlike in the seventh embodiment, is not provided with a needle abutment surface 90 and a suture channel 91. The construction other than the above is the same as for the needle guide 106 of the second embodiment.

A shaft 183 is attached to move between the two outer walls 15 at the distal end of the treatment lumen 12. The shaft 183 extends perpendicular to the direction of the opening of the side opening 13. A drum 184 having flanges at both ends is attached to and can rotate around the periphery of the shaft 183. Both ends of the suture 68 pass through the guide slits 181 and side holes 182 in the corresponding needle guides 178 and are lightly fixed to the inner surfaces of the outer wall 15 with temporary fixing members 185. A knot 186 is formed in the vicinity of the both ends of the suture 68 and is smaller than the width of the guide slit 181 and the inner diameter of the side hole 182, and larger than the width of the fixing groove 176. The suture 68 extending via the guide slit 181 into the treatment lumen 12 is wound around the drum 184 and lightly fixed by the temporary fixing member 185. The length of the suture 68 is the same as in the seventh embodiment.

Those skilled in the art will appreciate that variations in the eighth embodiment of the tissue puncturing system can be made. The needle guide 178 may not be provided with the curved part 180 as shown in FIG. 70. In this construction, a cutout 174 and a fixing groove 176 is formed at the distal end of the needle body 173.

An operation of the eighth embodiment of the tissue puncturing system will now be described. Descriptions will be given only where different from the seventh embodiment. The needles 172a and 172b penetrating the sutured tissues 97a and 97b enter the needle guides 178a and 178b. After the needle tip comes into contact with the curved part 180 as shown in FIG. 65, the needle 172 flexes as shown in FIG. 66, enters the internal channel in the curved part 180, and stops. The rings 48a and 48b on the slider receivers 46a and 46b and the fixing screws 57a and 57b on the inner sheath sliders 42a and 42b are loosened. The needle sliders 43a and 43b are removed from the housings 47a and 47b with the inner sheath sliders 42a and 42b and the needles 172a and 172b remaining connected. When the needles 172 start to be withdrawn from the needle guides 178, the hooks 177 catch the suture 68 crossing between the guide slit 181 and side hole 182. When the needles are further withdrawn, the suture 68 enters the fixing groove 176 and is fixed to the needle 172. The knot 186 serves as a stopper to prevent the suture 68 from coming out of the fixing groove 172. At the same time both ends of the suture 68 are released from the temporary fixing member 185. When the needles 172 are further removed, the suture 68 passes through the guide slit 181 and side hole 182 and is removed from the needle guide 178. When both ends of the suture 68 are retracted, the drum rotates to feed out the suture 68. Both ends of the suture 68 pass through the sutured tissues 97a and 97b and come out of the patient's body. Ultimately, the suture 68 is released by the temporary fixing member 185 from the drum 184, and a part of the suture 68 comes into contact with the sutured tissue 97b between the exiting points 113a and 113b.

In addition to the effects of the seventh embodiment, the effects described below are obtained. Since no hooks 169 or the like are provided at both ends of the suture 68, the ends are not required to be cut before the overtube 2 is removed from the patient's body. As a result, operability may be improved and the treatment time may be shortened. Since the suture 68 is wound around the drum 184, the suture 68 may be smoothly and reliably removed.

Figure 71:
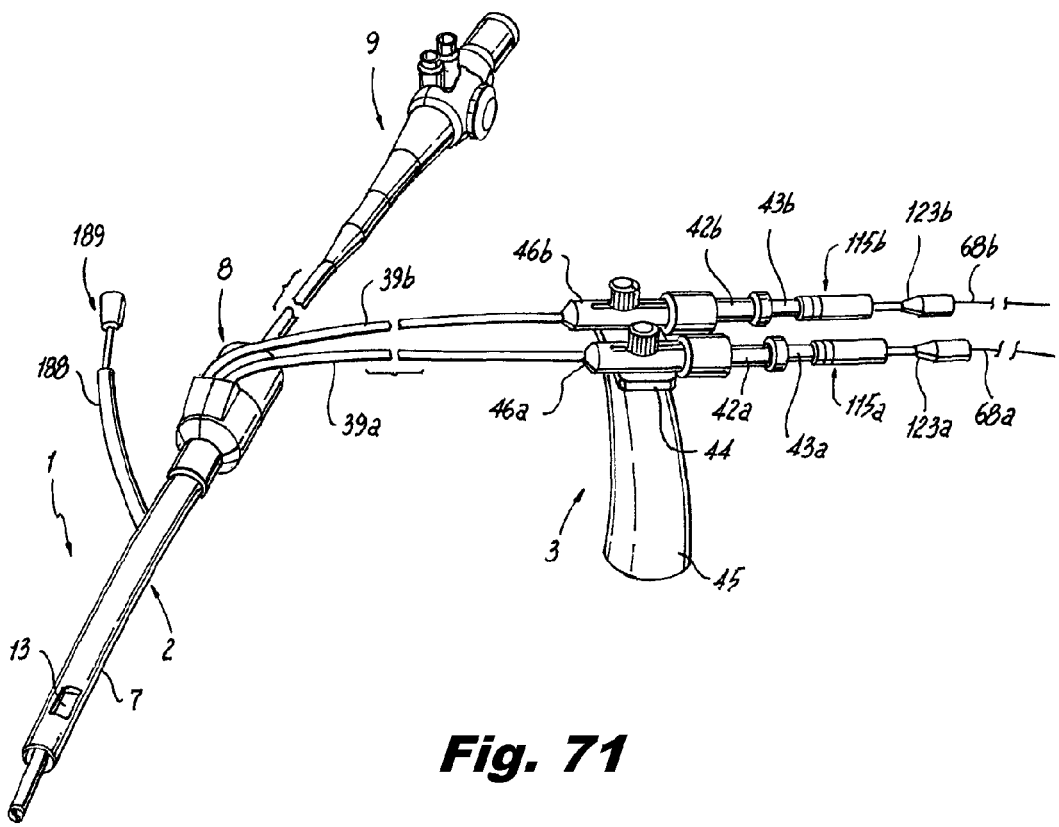
FIG. 71 is an external overview of a tissue puncturing system according to a ninth embodiment.
Figure 72:
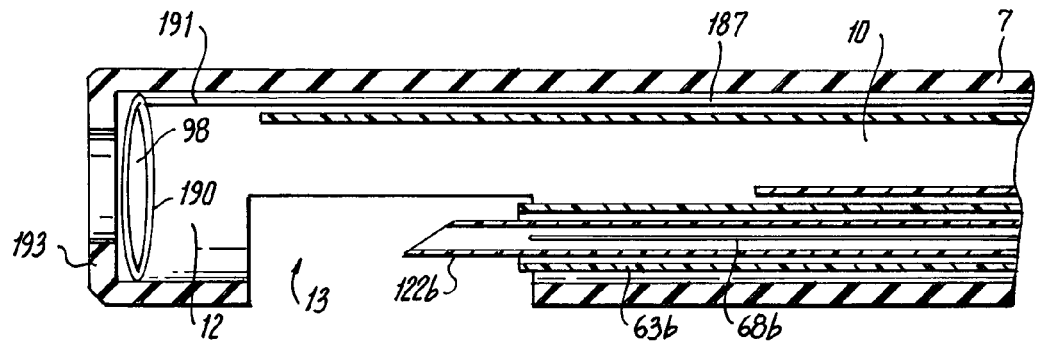
FIG. 72 is a vertical cross-sectional view of the front end of the overtube of FIG. 71, which is sectioned on a centerline of the needle.
Figure 73:
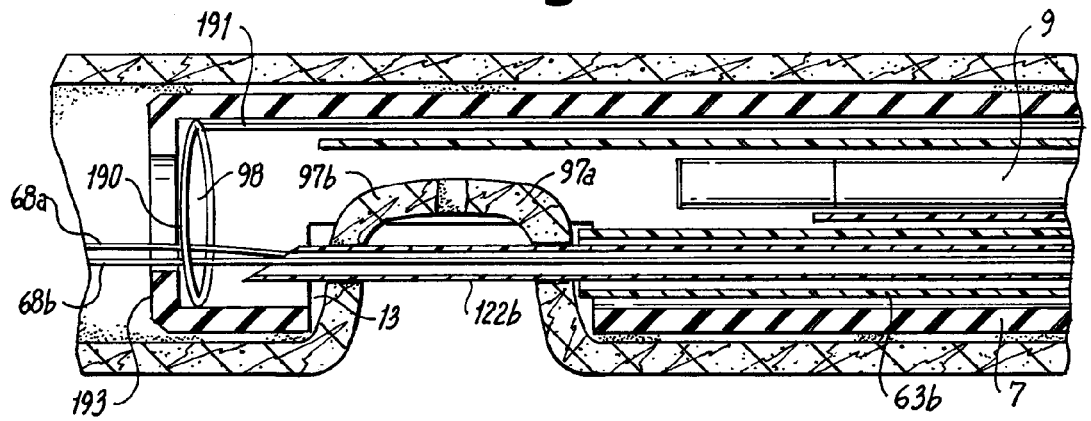
FIG. 73 is an operational view illustrating the tissue being punctured by the needle and the suture being pushed forward within the grip of the grasper.
Figure 74:
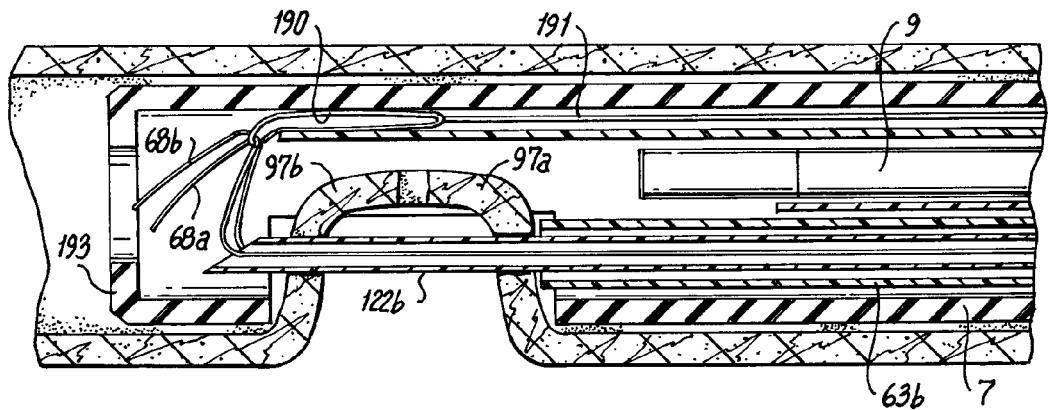
FIG. 74 is an operational view illustrating the suture being grasped by the grasper.
Figure 75:
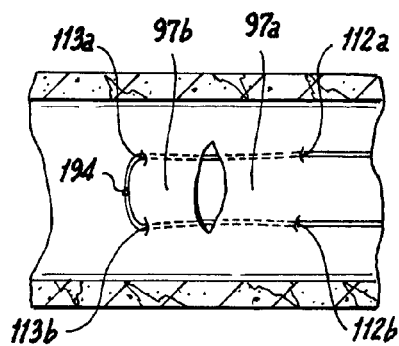
FIG. 75 is an operational view illustrating one end of the suture being knotted to be fed into the human body.
Figure 76:
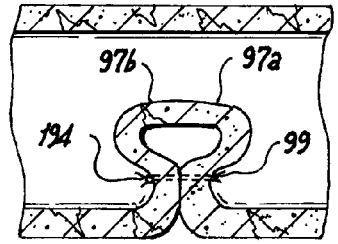
FIG. 76 is a view illustrating the tissue being put in a suture.
Figure 77:
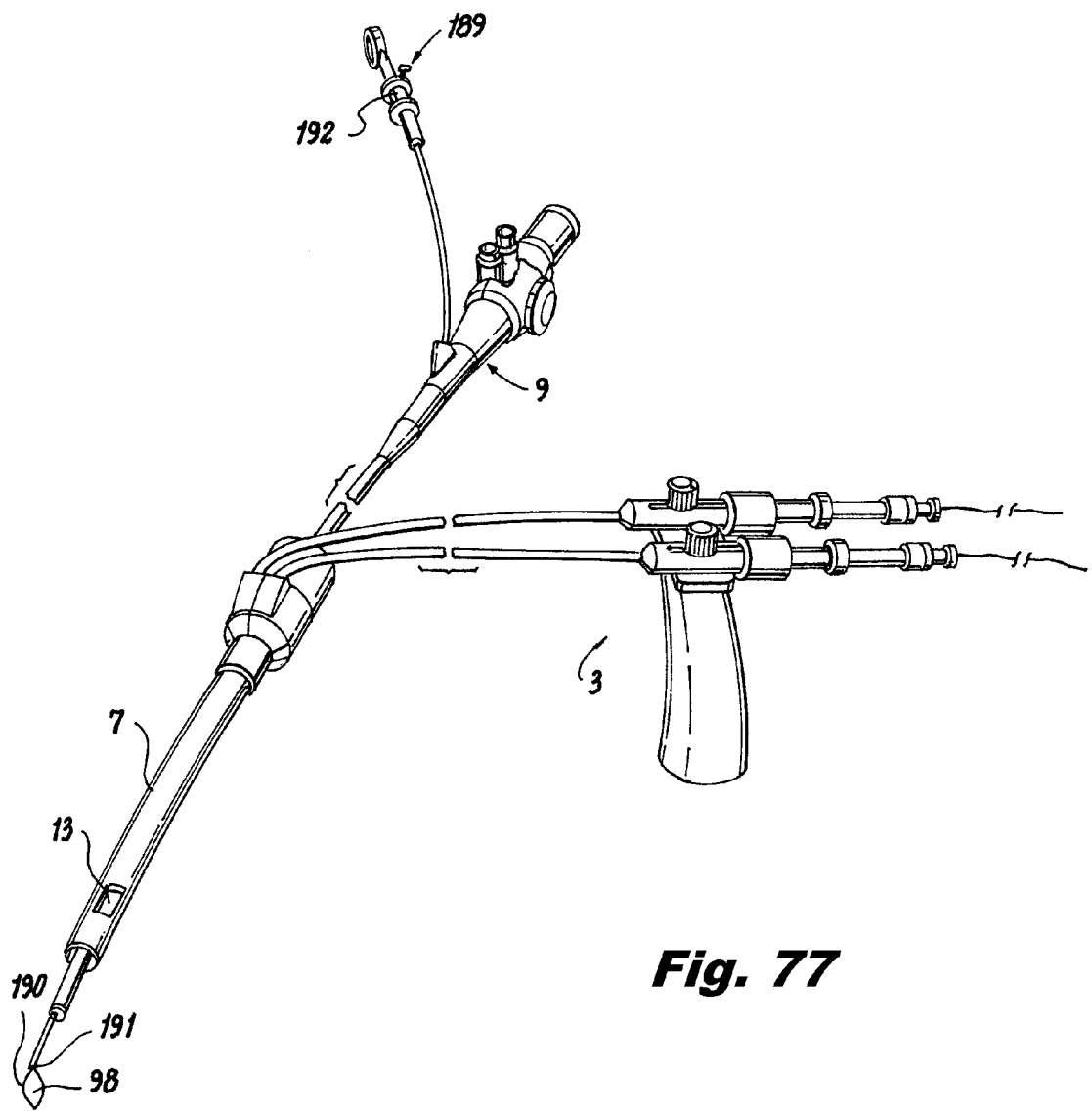
FIG. 77 is an external overview of the tissue puncturing system for showing a modification example according to the ninth embodiment.

A ninth embodiment of the tissue puncturing system will now be described with reference to FIGS. 71 through 77. FIG. 71 is an external overview of the entire tissue puncturing system. Descriptions will be given only where different from the first embodiment. FIG. 72 is a vertical cross-sectional view of the front end of the overtube, which is sectioned on a centerline of the needle. FIG. 73 is an operational view for showing a state such that the tissue is punctured by the needle and the suture is pushed forward within the grip of the grasper. FIG. 74 is an operational view for showing a state such that the suture is grasped by the grasper. FIG. 75 is an operational view for showing a state such that one end of the suture is knotted to be fed into the human body. FIG. 76 is a view for showing a state such that the tissue is put in a suture. FIG. 77 is an external overview of the entire tissue puncturing system for showing the modification example according to the ninth embodiment. As shown in FIGS. 72-74, an inwardly protruding convex surface 193 is provided all around on the internal channel of the treatment lumen 12 of the overtube 2 at its distal end. The convex surface 193 may be monolithically formed with the sheath section 7 or separately formed. A lumen 187 is provided in the internal channel of the sheath section 7. The distal end of the lumen 187 is positioned distal to the side opening 13. The proximal side opens over the outer wall 15 in the vicinity of the endoscope insertion section 8. A guide 188 having an internal channel is connected to the opening on the proximal side (FIG. 71). The internal channels in the lumen 187 and guide 188 are connected to each other. Suture forceps 189 are pre-inserted into the lumen 187 and guide 188 (FIG. 71). The suture forceps 189 comprise a grasper 190 connected to the distal end of the operation member 191 and an operation knob 192 connected to the proximal end of the operation member 191. The grasper 190 protrudes from the distal aperture of the lumen 187 and opens by pressing the operation knob 192 which retracts into the lumen 187 by pulling the operation knob 192 toward the proximal side.

The opened grasper 190 forms the loop opening 98, whose diameter is roughly the same as the inner diameter of the treatment lumen 12. The grasper 190 is bent substantially perpendicular to the longitudinal direction of the operation member 191, and opens along the proximal end surface of the convex surface 193. The construction of the grasper 190 and operation member 191 other than the above is the same as for the suture forceps 74 (FIG. 5) of the first embodiment. Although a needle guide is not provided on the distal annular part 79 of the reinforcing member 78 in the figure, a needle guide may be attached. When a needle guide is employed, the needle guide 82 (FIG. 2) of the first embodiment is provided. The two needles comprise the needles 115a and 115b shown in the third embodiment.

Those skilled in the art will appreciate that variations in the ninth embodiment of the tissue puncturing system are possible. Suture forceps 189 may be inserted in the forceps channel (not shown) in the endoscope 9 instead of providing the lumen 187 in the sheath section 7 to allow the passage of the suture forceps 189 as shown in FIG. 77.

An operation of the ninth embodiment of the tissue puncturing system will now be described. Descriptions will be given only where different from the first embodiment. The needles 115a and 115b are pushed to penetrate into the sutured tissues 97a and 97b and the operation knob 192 is pressed toward the distal end until the grasper 190 protrudes from the lumen 187. The grasper 190 opens along the proximal end surface of the convex surface 193 and inner surface of the treatment lumen 12 as shown in FIG. 72. The sutures 68a and 68b are advanced toward the distal end by using the suture feeders 123a and 123b in the needles 115a and 115b until they protrude from the needle tips. The sutures 68a and 68b are further advanced to pass through the loop opening 98 formed by the grasper 190. The operation knob 192 is then pulled toward the proximal side to retain the sutures 68a and 68b in the lumen 187. In this state, the needles 115a and 115b and the inner sheaths 4a and 4b are pulled into the needle lumen 11a and 11b. The suture 68 extending from the proximal side of the elastic grip 125 is released and the overtube 2 and endoscope 9 are removed from the patient's body. As a result, both the distal and proximal ends of the sutures 68a and 68b are exposed outside the patient's body. The grasper 190 is opened again to remove the distal ends of the sutures 68a and 68b and the distal ends are tied to form a knot 194. The proximal sides of the sutures 68a and 68b removed from the tissue puncturing system 1 are pulled to force the suture in the vicinity of the knot 195 against the sutured tissue 97b between the exiting points 113a and 113b. As shown in FIG. 76, finally, the sutures 68 exposed outside the patient's body are tied to form a knot 99 as in the first embodiment and the knot 99 is pushed into the body using a conventional knot pusher to ligate the proximal sides of the sutured tissue 97a. In addition to the effects of the first embodiment, no needle guide is required to be provided on the overtube 2, thus facilitating the manufacturing process and reducing the manufacturing costs.

Figure 78:
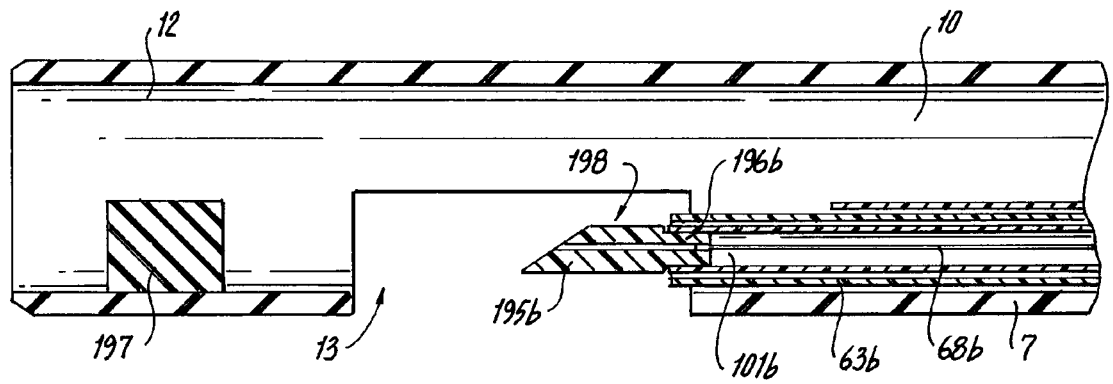
FIG. 78 is a vertical cross-sectional view of the front end of the overtube according to a tenth embodiment, which is sectioned on the centerline of the needle.
Figure 79:
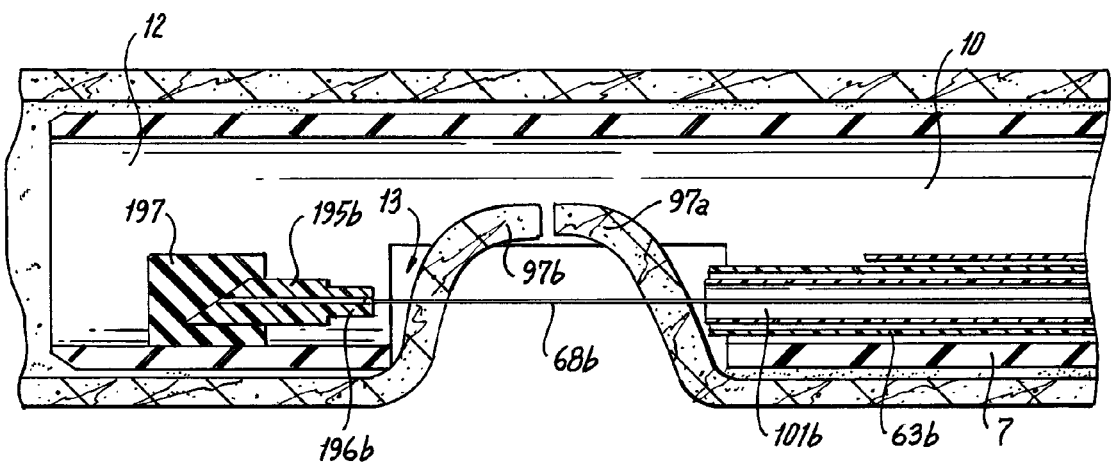
FIG. 79 is an operational view illustrating the suture being put through the tissue.

A tenth embodiment of the tissue puncturing system will now be described with reference to FIGS. 78 and 79. FIG. 78 is a vertical cross-sectional view of the front end of the overtube, which is sectioned on the centerline of the needle. FIG. 79 is an operational view for showing a state such that the suture is put through the tissue. Only those different from the first and ninth embodiments are described. Referring now to FIG. 78, two needles 198a and 198b have the same structure. Both needles 198a and 198b comprise a needle distal end 195, needle sheath 101 and needle grip 67. The needle grip 67 is connected to the proximal end of the needle sheath 101. The needle distal end 195 has a smaller diameter part 196 with a smaller outer diameter formed on the proximal side. The outer diameter of the smaller diameter part 196 is slightly larger than the inner diameter of the needle sheath 101, and the smaller diameter part 196 is a loose fit in the distal internal channel in the needle sheath 101. The length of the needle distal end 195 is set shorter than the length of protrusion from the distal end of the side opening 13 toward the distal side when the needle 198 is completely pushed out. The distal end of the suture 68 is fixed to the proximal end of the needle distal end 195 by an adhesive or the equivalent. The suture 68 extends to the proximal side of the needle grip 67. It is preferable that the cap 155 (FIG. 51) shown in the sixth embodiment is attached to the proximal end of the needle grip 67 to cover the proximal aperture of the needle grip 67 and fix the suture 68 to the needle grip 67.

A needle rest 197 is fixed on the distal side of the side opening 13 of the treatment lumen 12. The needle rest 197 is formed from a rubber such as silicone rubber fluoro-rubber, or a thermoplastic elastomer with a hardness that will allow easy puncturing by the needle distal end 195. The proximal end surface of the needle rest 197 is positioned so that the needle distal end 195 may puncture it for a depth of approximately 10 mm when the needle 198 is completely protruded. The force required to pull the needle distal end 195 from the needle rest 197 is set larger than the force required to pull the needle distal end 195 from the needle sheath 101. It is preferable that a proximally facing small barb (not shown) is provided on the periphery of the needle distal end 195. Although the reinforcing member 78 and needle guide are shown in the treatment lumen 12 in the figure, both members may be provided. In this case, they are preferably provided so that the distal end of the needle guide is positioned proximal to the proximal end of the needle distal end 195 puncturing the needle rest 197. The internal channel in the needle guide shall have an inner diameter that allows the needle distal end 195 to pass through. No convex surface 193 is provided on the sheath section 7.

An operation of the tenth embodiment of the tissue puncturing system will now be described. Descriptions will be given only where different from the first and ninth embodiments. As shown in FIG. 79, the needles 198a and 198b penetrating the sutured tissues 97a and 97b puncture the needle rest 197. The needle sliders 43a and 43b are returned to remove the needles 198a and 198b. When the suture 68 is fixed to the needle grip 67 with the cap 155, the cap 155 is removed from the needle grip 67 before removing the needles. Then the needle distal end 195 is released from the needle sheath 101, leaving the needle distal end 195 alone connected to the needle rest 197. A barb, if provided around the needle distal end 195, may prevent the needle distal end 195 from coming off from the needle rest 197. The suture 68 extending from the proximal side of the needle grip 67 is released and the overtube 2 and endoscope 9 are removed from the patient's body. As a result, both the distal and proximal ends of the sutures 68a and 68b are exposed outside the patient's body.

In addition to the effects of the first embodiment, the effects described below are obtained. It is not required to transfer the suture 68 between two needles or feed the suture 68, thus improving operability and shortening the treatment time. The needle guide is not required on the overtube 2, thus facilitating the manufacturing process and reducing the manufacturing costs.

Figure 83:
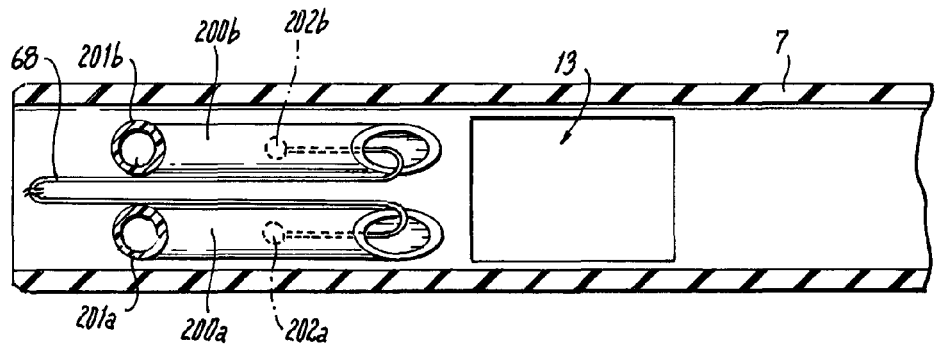
FIG. 83 is a vertical cross-sectional view of the overtube that is orthogonal to the view illustrated in FIG. 81.
Figure 84:
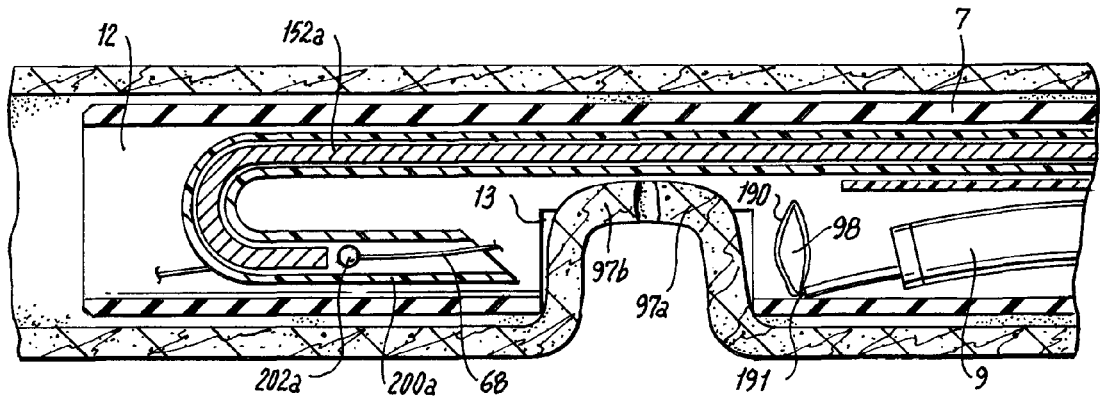
FIG. 84 is a view illustrating the endoscope and the grasper being inserted within the overtube where the tissue has not yet been punctured by the needle.
Figure 85:
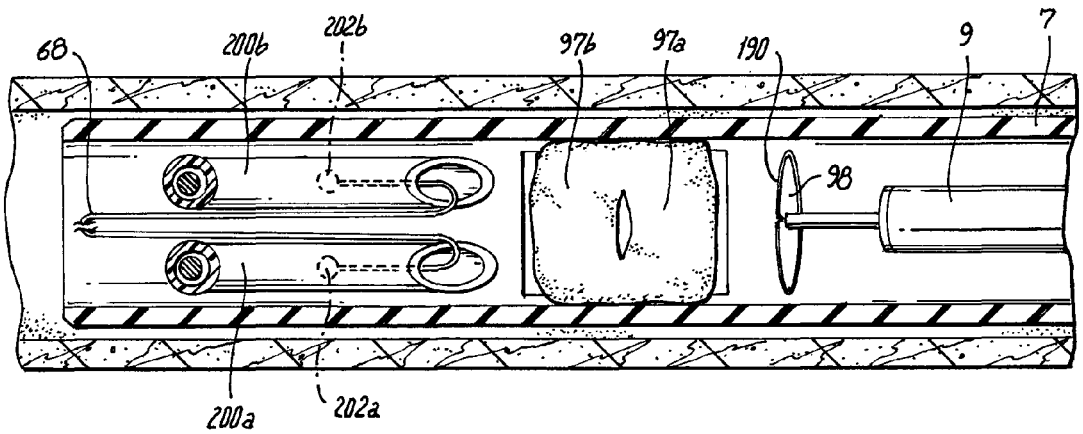
FIG. 85 is a vertical cross-sectional view that is orthogonal to the view illustrated in FIG. 84.
Figure 86:
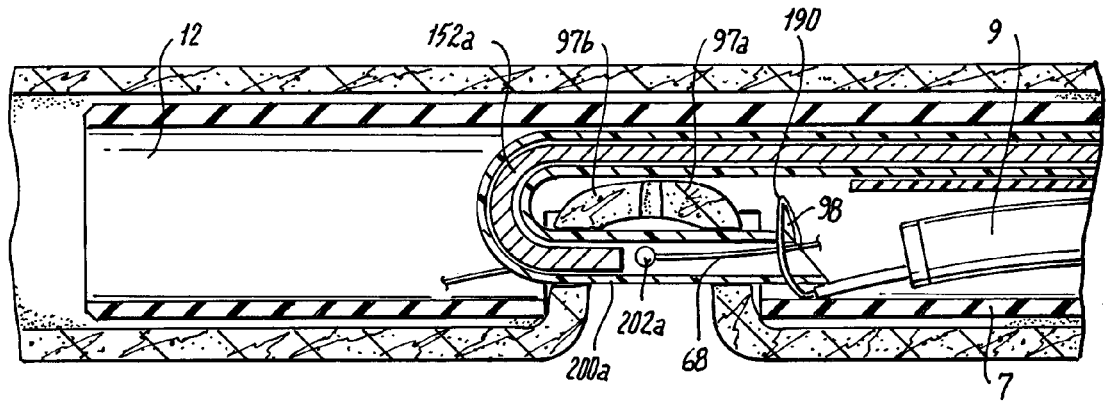
FIGS. 86 to 89 are operational views illustrating putting the suture through the tissue by puncturing the tissue by the needle.
Figure 87:
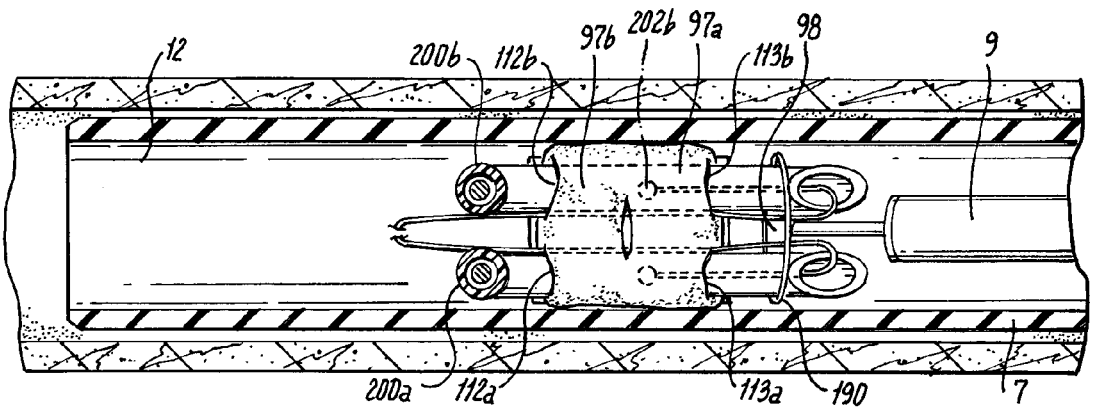
Figure 88:
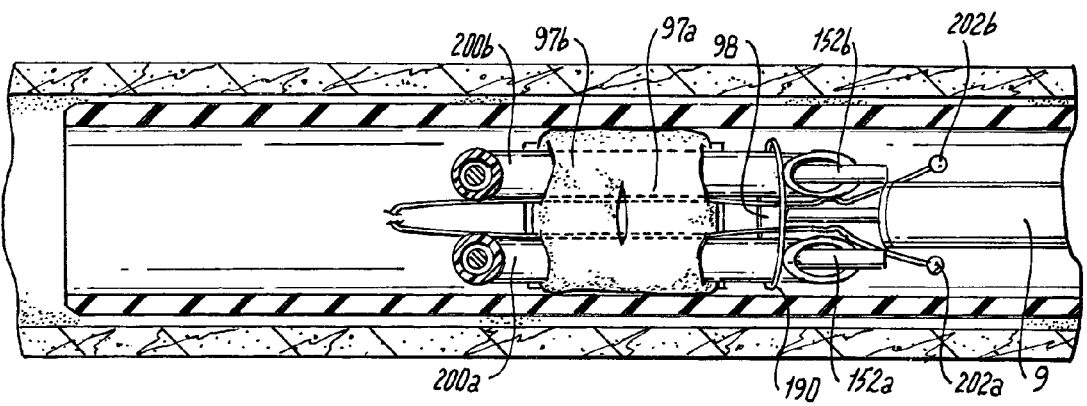
Figure 89:
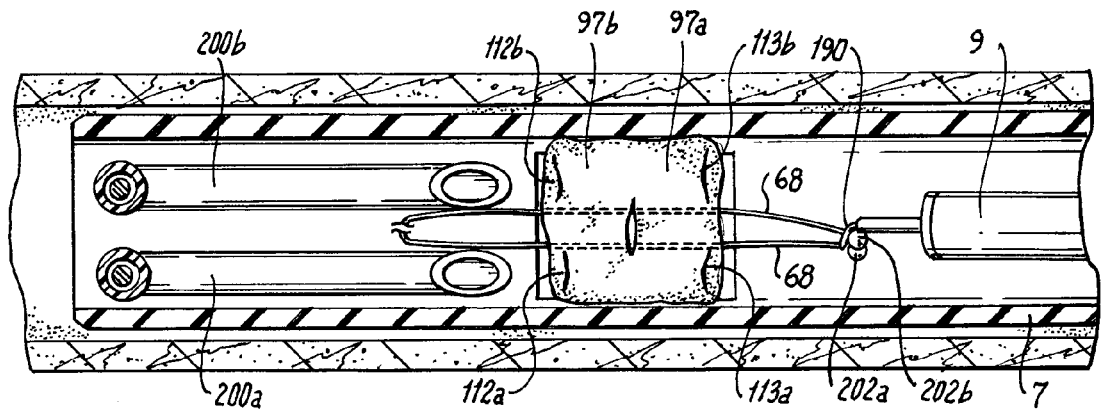
Figure 90A:
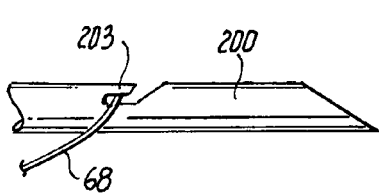
FIGS. 90(a) and 90(b) are a side view and a front view, respectively, of the front end of the needle in a modification example according to the eleventh embodiment.
Figure 90B:
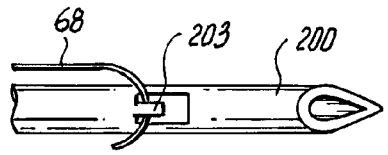

An eleventh embodiment of the tissue puncturing system will now be described with reference to FIGS. 80 through 90. FIG. 80 is an external overview of the entire tissue puncturing system. FIG. 81 is a vertical cross-sectional view of the front end of the overtube, which is sectioned on the centerline of the needle. FIG. 82 is a horizontal cross sectional view taken along the line E-E in FIG. 81. FIG. 83 is a vertical cross-sectional view that is orthogonal to FIG. 81. FIG. 84 is a view for showing a state such that the endoscope and the grasper are inserted within the overtube and the tissue has not been punctured by the needle yet. FIG. 85 is a vertical cross-sectional view that is orthogonal to FIG. 84. FIG. 86 to FIG. 89 are operational views for showing a state of putting the suture through the tissue by puncturing the tissue by the needle. FIG. 90(a) and FIG. 90(b) are a side view and a front view of the front end of the needle in the modification example according to the eleventh embodiment, respectively. Descriptions will be given only where different from the first embodiment. The side opening 13, unlike in the first embodiment, is positioned on the outer wall 15b. opposite to the needle lumens 11a and 11b. The two needles 199a and 199b have the same structure. Both needles 199a and 199b comprise a needle body 200, needle grip distal part 71 (FIG. 5), needle grip proximal part 72 (FIG. 5), O-ring 73 (FIG. 42), and pusher tube 151 (FIG. 51). Although the constructions of the needle grip distal part 71, needle grip proximal part 72, O-ring 73, and pusher tube 151 are the same as those of the needle 149 of the sixth embodiment, the cap 155 does not need to be provided on the pusher tube 151. As shown in FIG. 81, a bend 201 with its tip end facing the proximal end is provided in the distal end of the needle body 200. The bend 201 is moderately curved so that the sheath 152 of the pusher tube 151 will slide in it.

The diameter of the bend 201 is slightly smaller than the inner diameter of the treatment lumen 12 so that the distal end of the needle body 200 moves immediately above the side opening 13. The needle body 200 with the inner sheath sliders 42a and 42b and needle sliders 43a and 43b mounted on the slider receivers 46a and 46b slides in the needle lumens 11a and 11b, and its proximal end is connected to the needle grip distal parts 71a and 71b.

The distal end of the needle body 200 is set to a length so that it is positioned distal to the side opening 13 when the needle slider 43 is completely advanced and proximal to the side opening 13 when the needle slider 43 is completely retracted. The distal ends of the needle bodies 200a and 200b are each set with both ends of the suture 68 approximately 15 mm in length. Larger diameter members 202 are attached to both ends of the suture 68 and may protrude from the distal ends of the needle bodies 200 when the pusher tubes 51 are advanced. Parts exposed from the needle bodies 200 remain in the treatment lumen 12. Although no inner sheath is provided in the figure, inner sheaths may be provided. In that case, the inner sheaths shall have bends as the needle 199. Although the reinforcing member 78 and needle guide are not provided, they may be provided. In that case, the needle guide 82 is attached at the proximal end of the side opening 13 so that the tapered part 88 faces the distal side. Suture forceps having a loop-shaped grasper 190 such as ordinary snare forceps are inserted through the forceps channel (not shown) of the endoscope 9.

Those skilled in the art will appreciate that variations in the eleventh embodiment of the tissue puncturing system are possible. As shown in FIG. 90, hooks 203 may be provided on the periphery of each of the needles' distal ends to accept. both ends of the suture 68 instead of setting both ends of the suture 68 in the distal internal channels of the needle bodies 200. In that case, no pusher tube 151 is required.

An operation of the eleventh embodiment of the tissue puncturing system will now be described. With the needle sliders 43a and 43b completely advanced toward the distal end, position the side opening 13 above the sutured tissues 97a and 97b and apply suction from the endoscope 9. The suture forceps 189 are extended from the forceps channel of the endoscope,9 the operation knob 192 is pressed forward to open the grasper 190, and a loop opening 98 is formed in the vicinity of the sucked sutured tissue 97a. The needle sliders 43a and 43b are retracted toward the proximal side, and the needle bodies 200 are pulled to puncture the sutured tissues 97a and 97b. The suture 68 is inserted along the needle bodies 200 via the entering point 112 at the sutured tissue 97b and comes out of the exiting point 113 at the sutured tissue 97a. The distal end of the needle protruding from the sutured tissue 97a passes through the loop opening 98. The grip 153 on the pusher tube 151 is pressed to advance the larger diameter member 202 and both ends of the suture 68 from the distal end of the needle. The operation knob 192 is retracted toward the proximal side to close the grasper 190 and grasp both ends of the suture 68. At this stage, the larger diameter member 202 serves as a stopper to prevent the suture 68 from slipping off the grasper 190. The needle sliders 43a and 43b are advanced to the distal ends again to remove the needle bodies 200 from the sutured tissues 97a and 97b. When both ends of the suture 68 are engaged with the hooks 203, both ends of the suture 68 separate from the needle bodies on removal of the needle bodies 200. The endoscope 9 alone is removed from the patient. Both ends of the suture 68 are pulled out of the patient's body, and a part of the suture 68 comes into contact with the sutured tissue 97b between the entering points 112a and 112b. Then the overtube 2 is removed from the patient's body.

In addition to the effects of the first embodiment, the effects described below are obtained. In the first embodiment, the pushing force applied from the proximal side may not be sufficiently transferred to the distal end since the needles may flex in the inner sheaths when the needles are advanced at the time of puncture. Since the puncture is attained by pulling the needles, the needles do not flex, and the pulling force applied from the proximal side is directly transferred to the distal end of the needle, thus improving the efficiency of the puncture against the target tissue. No needle guide is required on the overtube 2, thus facilitating the manufacturing process and reducing the manufacturing costs.

Figure 91:
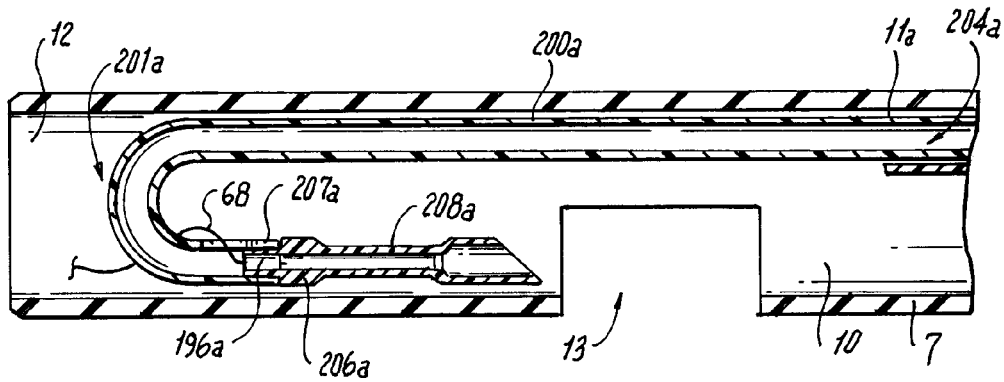
FIG. 91 is a vertical cross-sectional view of the front end of the overtube according to a twelfth embodiment, which is sectioned on the centerline of the needle.
Figure 92:
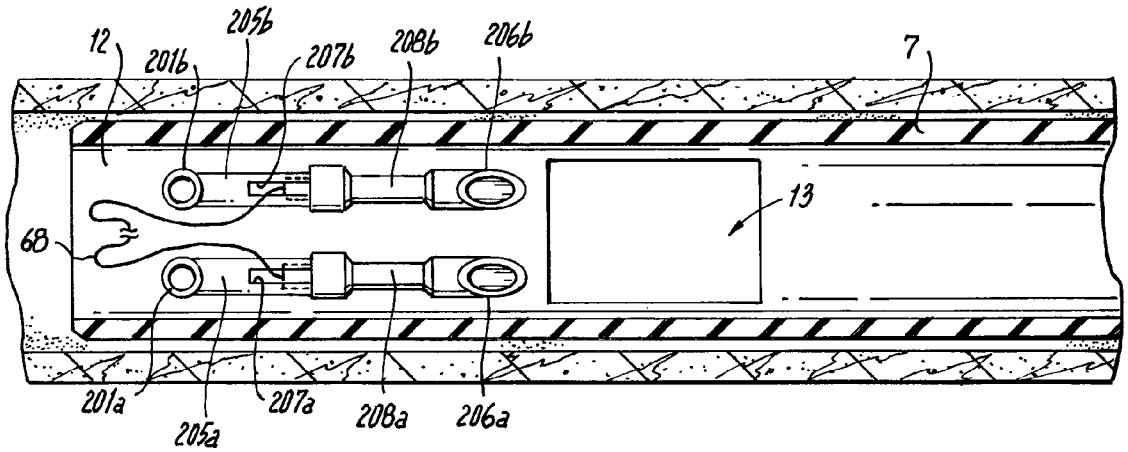
FIG. 92 is a vertical cross-sectional view of the overtube that is orthogonal to the view illustrated in FIG. 91.
Figure 93:
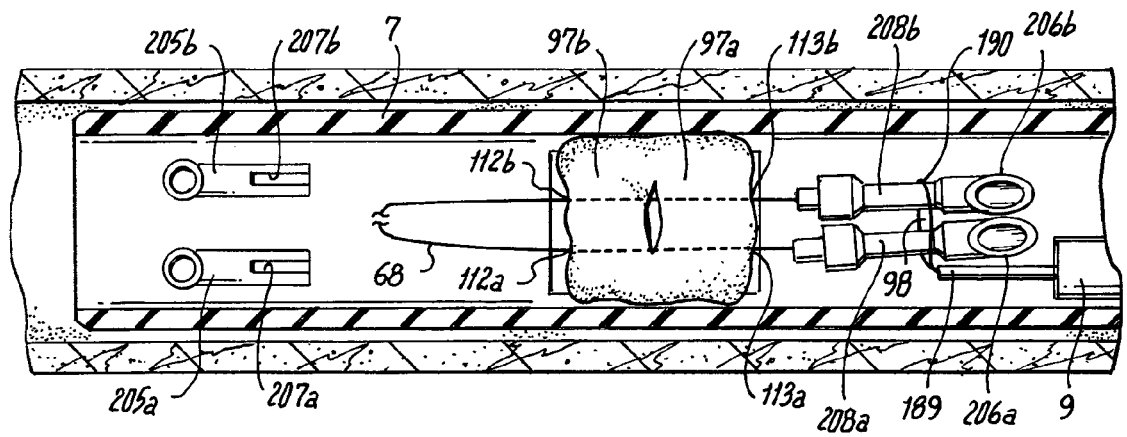
FIG. 93 is an operational view illustrating the suture being put through the tissue.
Figure 94:
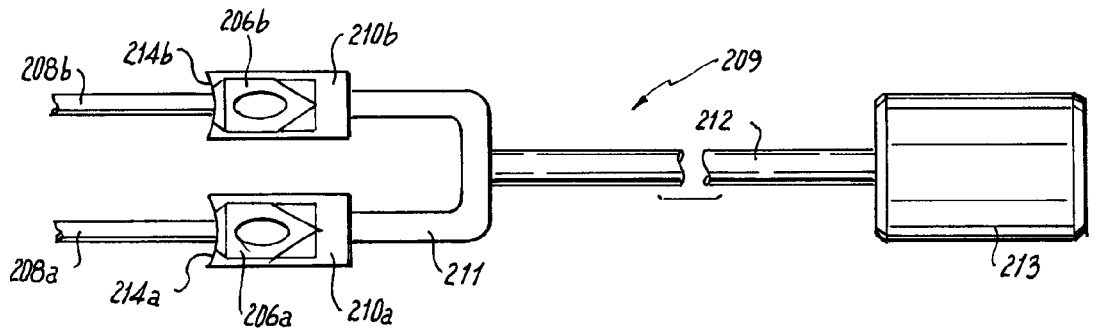
FIG. 94 is a view illustrating the front end of the needle being grasped by the grasper in the modification example according to the twelfth embodiment.

A twelfth embodiment of the tissue puncturing system will now be described with reference to FIGS. 91 through 94. FIG. 91 is a vertical cross-sectional view of the front end of the overtube, which is sectioned on the centerline of the needle. FIG. 92 is a vertical cross-sectional view that is orthogonal to FIG. 91. FIG. 93 is an operational view for showing a state such that the suture is put through the tissue. FIG. 94 is a view for showing a state such that the front end of the needle is grasped by the grasper in the modification example according to the twelfth embodiment. Descriptions will be given only where different from the eleventh embodiment. Two needles 204a and 204b have the same structure. The needles 204 respectively comprise a needle sheath 205, needle distal end 206, and needle grip 67. A bend 201 is provided in the needle sheath 205 to match the needle body 200 of the eleventh embodiment. The needle grip 67 is connected to the proximal side of the needle sheath 205. A slit 207 with a width that allows passage of the suture 68 is provided at the distal end of the needle sheath 205. An annular groove 208 is provided all around the needle distal end 206 at its center. A smaller diameter part 196 is provided at the distal side (distal side of the sheath section 7) of the needle distal end 206 as in the tenth embodiment, which is a light fit in the distal inner channel of the needle sheath 205. The distal end of the needle distal end 206 is positioned distal to the side opening 13 when the needle slider 43 is completely pulled out.

One end of the suture 68 is fixed to the distal side of the needle distal end 206 as in the tenth embodiment, and the suture 68 passes through the slit 207 and extends out of the needle. A suture grasper 209 may be inserted through the forceps channel of the endoscope 9 instead of the suture forceps 189 of the eleventh embodiment. The suture grasper 209 comprises two grasping parts 210, connecting part 211, operation member 212, and operation knob 213. The operation knob 213 is attached to the proximal end of the operation member 212. The connecting part 211 is fixed to the distal end of the operation member 212. The operation member 212 is formed from a flexible metal coil so that it can slide in the forceps channel of the endoscope 9. The two grasping parts 210a and 210b are provided at the both ends of the connecting part 211 and are substantially parallel to each other at a constant distance. The distance is substantially the same as the distance between the needles 204a and 204b. The grasping parts 210 are made from tubular members formed from plastic material such as polypropylene or ABS. A. convex part 214 is formed all around the internal circumference of the distal end of each grasping part 210. The height of the convex part 214 is substantially equal to the depth of the annular groove 208 in the needle distal end 206.

An operation of the twelfth embodiment of the tissue puncturing system will now be described. Descriptions will be given only where different from the eleventh embodiment. The annular grooves 208a and 208b in the needle distal ends 206a and 206b are held, penetrating the sutured tissues 97a and 97b using the grasping parts 190 of the suture forceps 189, and the endoscope 9 is removed. The needle distal end 206 separates from the distal end of the needle sheath 205. The endoscope 9 is then further removed, the needle distal end 206 and suture 68 penetrate the entering point 112 and the exiting point 113. Ultimately, both ends of the suture 68 are pulled out of the patient's body, and a part of the suture 68 comes into contact with the sutured tissue 97b between the entering points 112a and 112b. When the suture grasper 209 is used, press the operation knob 213 toward the distal side to insert the needle distal end 206 into the internal channel of the grasping part 210. As a result, the convex part 214 and the annular groove 208 in the needle distal end 206 are engaged to hold the needle distal end 206.

In addition to the effects of the eleventh embodiment, the effects described below are obtained. Since the needle distal end 206 is removed from the sutured tissues 97a and 97b by removing the endoscope 9, removal by the needle slider is not required, thus improving the operability and reducing the treatment time. Since the needle distal end 206 may be held with the suture grasper 209, when used, simply by pressing the suture grasper 209 against the needle distal end 206, it is not necessary to open and close a loop grasper, thus improving the operability and reducing the treatment time.

In the constitutions described above, those skilled in the art will appreciate that the following advantages are gained.

The flexible sheath is provided with the lumen for accepting the endoscope and this allows the endoscope to be inserted into the space into which the sutured tissues are sucked. In this construction, the sutured tissues are sucked into the internal channel of the lumen located at a position substantially coaxial with and in front of the endoscope. Therefore, the means of puncturing may satisfactorily puncture the target puncture site of the tissue and a satisfactory puncture may be readily and reliably confirmed before actually puncturing. In addition, the distal end of the endoscope may be moved back and forth against the side opening or curved for adjustment to obtain the optimum state for observation of the sucked tissues. Thus, the puncture site may be minutely controlled to attain reliable suturing. The treatment operation is simplified, and the treatment time is significantly shortened.

Since the means of puncturing are positioned at a uniform interval and in parallel, the puncture points (entering points and exiting point) made in the sutured tissues are at a uniform interval. Thus a uniform stitch interval is ensured and may be reliably controlled, thus simplifying the treatment procedure and drastically reducing the treatment time.

Even when multiple stitches are required, the distance between stitches may be controlled so as to achieve reliable suturing with the least number of stitches. Since the endoscope lies substantially coaxial with the space into which the sutured tissues are sucked, a large space may be used to suck in the tissues without increasing the outer diameter of the flexible sheath, thus minimizing any pain experienced by the patient during insertion of the flexible sheath. Since the endoscope can slide in the flexible sheath, the endoscope and the flexible sheath may be inserted into body cavity of the patient with a bending section of the endoscope protruding from the distal aperture of the flexible sheath, thus improving the insert ability of the endoscope and the flexible sheath, and minimizing any pain experienced by the patient during insertion.

Since two means of puncturing are available, they may be used to puncture the tissue immediately after the tissues are sucked in through the side opening, thus simplifying the treatment procedure and drastically reducing the treatment time. Since the tissue is punctured after the inner sheaths butt up against the target puncture site, the target puncture site and positioning may be readily confirmed, thus giving reliable suturing, simplifying the treatment procedure and drastically reducing the treatment time.

Since at least a part of the flexible sheath in the vicinity of the side opening is transparent, the outside of the flexible sheath may be observed with the endoscope making it easier to position the side opening, thus improving operability and reducing the treatment time.

Since the distal end of the flexible sheath is independent, the components other than the distal end unit may be used in common when the tissue puncturing system is manufactured with side openings of different sizes, thus reducing the manufacturing costs.

Since the system is constructed to be airtight to the outside except for the distal aperture and the side opening in the flexible sheath, suction can be maintained efficiently on the sutured tissues via the side opening.

What is clamed is:

1. A tissue puncturing system used to suture tissues in a body cavity comprising:
    an endoscope;
    a flexible sheath having a distal portion provided with at least a side opening, and a lumen through which the endoscope may pass;
    at least one puncturing member disposed in the flexible sheath, and having a pointed end, which end is movable from a first position to a second position, the at least one puncturing member having a suture lumen, a suture disposed in the suture lumen;
    an operating puncture member for moving the puncturing member between the first and second positions;
    a suction system for creating a negative pressure on an interior of the flexible sheath to suck a living tissue from the side opening to the interior of the flexible sheath; and
    at least one member for receiving the puncturing member provided inside of the flexible sheath at a position more distal than the side opening, the at least one member having a through hole for passage of the puncturing member and further having a slit in communication with the through hole along an entire length of the through hole;
    wherein the at least one member comprises first and second members which are provided substantially parallel and maintained at a fixed distance with each other in the flexible sheath, the art least one puncturing member comprises first and second puncturing members which are provided substantially parallel and maintained at a fixed distance with each other in the flexible sheath, the first member receiving the first puncturing member having the suture and the second member receiving a second puncturing member;
    wherein the at least one puncturing member is advanced distally through the through hole to puncture the living tissue in the interior of the flexible sheath, the suture is advanced distally of the pointed end of the puncturing member and the suture is withdrawn proximally through the slit when the puncturing member is moved proximally; and
    wherein the other of the two puncturing members is provided with a holding suture member for receiving and holding the suture.

2. A tissue puncturing system according to claim 1, wherein the suction system comprises a suction channel connected to a proximal end of the flexible sheath and a suction source connected to a proximal end of the suction channel.

3. A tissue puncturing system according to claim 1, wherein at least a portion of the flexible sheath is transparent in the vicinity of the side opening.

4. A tissue puncturing system according to claim 1, wherein the distal portion of the flexible sheath is detachable.

5. A tissue puncturing system according to claim 1, wherein the first position is located proximal to the side opening and the second position is distal to the side opening.

6. A tissue puncturing system according to claim 1, wherein the first position is located distal to the side opening and the second position is proximal to the side opening.

7. A tissue puncturing system used to suture tissues in a body cavity comprising:
    an endoscope;
    a flexible sheath comprises:
        a distal portion having a side opening for sucking a living tissue;
        a lumen for movably accommodating the endoscope along the lumen so that the endoscope can be located at a position more proximal than the side opening;
    at least one puncturing member disposed in the flexible sheath, and having a pointed end, which end is movable from a first position to a second position, the at least one puncturing member having a suture lumen, a suture disposed in the suture lumen;
    at least one member for receiving the at least one puncturing member used for suturing the tissue provided inside of the flexible sheath at a position more distal than the side opening;
    the at least one member having a through hole for passage of the the at least one puncturing member and the suture and further having a slit in communication with the through hole along an entire length of the through hole;
    wherein the the at least one puncturing member is advanced distally through the through hole to puncture living tissue in an interior of the flexible sheath, the suture is advanced distally of a distal end of the needle and the suture is withdrawn proximally through the slit when the needle is moved proximally;
    wherein the at least one member comprises first and second members, the at least one puncturing member comprises first and second puncturing members, the first member receiving the first puncturing member having the suture and the second member receiving a second puncturing member also being movable between the first and second positions by operation of an operating member;
    wherein the second puncturing member includes a holding suture member for receiving and holding the suture, the holding suture member being movable distally and proximally relative to the second puncturing member;
    wherein the first and second members are configured such that when the suture is advanced distally, the first puncturing member is advanced to project distally from the first member and the holding suture member is advanced to project distally from the second member so as to hold the suture; and
    wherein the slit is a first slit and the second member has a second slit opposing the first slit, and when the first puncturing member and the holding suture member are moved proximally with the suture held by the holding suture member, the suture is released from the first and second members through the first and second slits.

* * * * *